(12) United States Patent
Yasuma et al.

(10) Patent No.: US 7,517,910 B2
(45) Date of Patent: *Apr. 14, 2009

(54) ALKOXYPHENYLPROPANOIC ACID DERIVATIVES

(75) Inventors: Tsuneo Yasuma, Osaka (JP); Shuji Kitamura, Osaka (JP); Nozomu Sakai, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 37 days.

This patent is subject to a terminal disclaimer.

(21) Appl. No.: 10/594,996

(22) PCT Filed: Mar. 28, 2005

(86) PCT No.: PCT/JP2005/006522

§ 371 (c)(1),
(2), (4) Date: Sep. 29, 2006

(87) PCT Pub. No.: WO2005/095338

PCT Pub. Date: Oct. 13, 2005

(65) Prior Publication Data

US 2007/0213364 A1 Sep. 13, 2007

(30) Foreign Application Priority Data

Mar. 30, 2004 (JP) .............................. 2004-101149

(51) Int. Cl.
*A61K 31/192* (2006.01)
*C07C 61/12* (2006.01)
(52) U.S. Cl. ....................................... 514/569; 562/499
(58) Field of Classification Search ................. 514/569; 562/499
See application file for complete search history.

(56) References Cited

U.S. PATENT DOCUMENTS 5,360,815 A 11/1994 Fortin et al.
2006/0004012 A1* 1/2006 Akerman et al. ............ 514/249

FOREIGN PATENT DOCUMENTS

| JP | 2-288862 | 11/1990 |
|---|---|---|
| JP | 5-221927 | 8/1993 |
| WO | 02/053547 | 7/2002 |
| WO | 03/016254 | 2/2003 |
| WO | 03/066574 | 8/2003 |
| WO | 03/068959 | 8/2003 |
| WO | 2004/041266 | 5/2004 |
| WO | 2005/063725 | 7/2005 |
| WO | 2005-063729 | 7/2005 |

OTHER PUBLICATIONS

Supplementary European Search Report issued *Sep. 28, 2007* in the corresponding European Application.

* cited by examiner

*Primary Examiner*—Taofiq A Solola
(74) *Attorney, Agent, or Firm*—Wenderoth, Lind & Ponack, L.L.P.

(57) ABSTRACT

The present invention aims at provision of a novel compound having a GPR40 receptor function modulating action, which is useful as an insulin secretagogue, an agent for the prophylaxis or treatment of diabetes and the like. The compound represented by the formula:

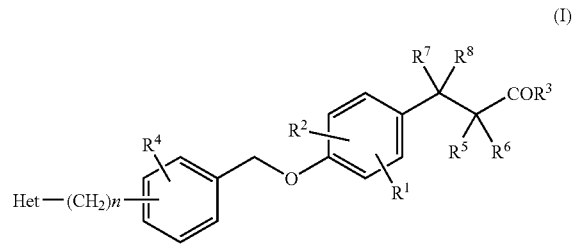

(I)

wherein each symbol is as defined in the description, a salt thereof, and a prodrug thereof of the present invention unexpectedly have a superior GPR40 receptor agonistic activity and superior properties as pharmaceutical products such as stability and the like, and can be safe and useful pharmaceutical agents as agents for the prophylaxis or treatment of GPR40 receptor-related pathology or diseases in mammals.

12 Claims, No Drawings

ALKOXYPHENYLPROPANOIC ACID DERIVATIVES

This application is a U.S. national stage of International Application No. PCT/JP2005/006522 filed Mar. 28, 2005.

TECHNICAL FIELD

The present invention relates to a novel compound having a GPR40 receptor function modulating action, which is useful as an agent for the prophylaxis or treatment of diabetes.

BACKGROUND ART

It has been reported in recent years that a ligand of GPR40, which is one of the G Protein-Coupled Receptors (GPCR), is fatty acid and GPR40 in pancreatic β cell is deeply involved in insulin secretion action (see Nature, 2003, vol. 422, pages 173-176). Thus, a GPR40 agonist promotes insulin secretion, a GPR40 antagonist inhibits insulin secretion, and the agonist and the antagonist are useful as a therapeutic agent for type 2 diabetes, obesity, impaired glucose tolerance, insulin resistance, neurodegenerative diseases (e.g., Alzheimer's disease) and the like (see WO02/057783).

There are many compounds reported to be useful as therapeutic agents for diabetes.

For example, WO03/066574 discloses that aromatic amino acid derivatives represented by the formula:

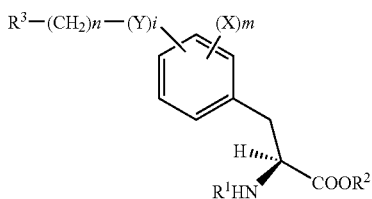

[X: halogen atom etc.; Y: O etc.; i: 1 etc.; m: 0, 1, 2; n: 1 etc.; $R^1$: H etc.; $R^2$: H etc.; $R^3$: phenyl group substituted by pyridyl etc., and the like]
are expected to have an action to suppress hyperglycemia.

WO02/053547 discloses that a compound represented by the formula:

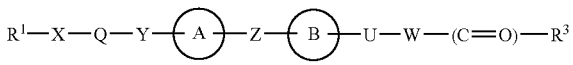

[$R^1$: optionally substituted 5-membered aromatic heterocyclic group; X: bond etc.; Q: $C_{1-20}$ divalent hydrocarbon group; Y: bond etc.; ring A: optionally substituted aromatic ring; Z: —$(CH_2)n$-$Z^1$-(n=1-8, $Z^1$=O etc.); ring B: optionally substituted pyridine, benzene etc.; U: bond etc.; W: $C_{1-20}$ divalent hydrocarbon group; $R^3$: —$OR^8$ ($R^8$=H etc.) etc.] is useful as an agent for the prophylaxis or treatment of diabetes, hyperlipidemia, impaired glucose tolerance and the like.

However, it has not been disclosed at all that these known therapeutic drugs for diabetes have a GPR40 receptor function modulating action, and additionally there is no report on a compound having a GPR40 receptor function modulating action (compound useful as a GPR40 agonist or GPR40 antagonist). Under the circumstances, development of a compound having a GPR40 receptor function modulating action has been desired.

DISCLOSURE OF THE INVENTION

The present invention aims at providing a novel compound having a GPR40 receptor function modulating action, which is useful as an insulin secretagogue or an agent for the prophylaxis or treatment of diabetes and the like.

The present inventors have intensively conducted various studies and found that the compounds represented by the following formula (I) unexpectedly have a superior GPR40 receptor agonist activity, show superior properties as pharmaceutical products such as stability and the like, and can be safe and useful pharmaceutical agents for the prophylaxis or treatment of GPR40 receptor related disease state or diseases in mammals, and completed the present invention.

Accordingly, the present invention provides the following.

[1] A compound represented by the formula:

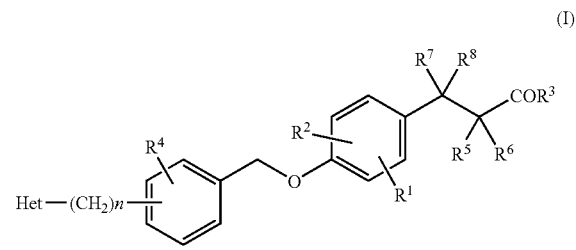

wherein Het is an optionally substituted heterocyclic group,
N is 0 or 1,
$R^1$ and $R^2$ are the same or different and each is a hydrogen atom, a $C_{1-6}$ alkyl group or a halogen atom,
$R^3$ is an optionally substituted hydroxy group or an optionally substituted amino group,
$R^4$ is a hydrogen atom, an optionally substituted hydrocarbon group, an optionally substituted hydroxy group or an optionally substituted amino group,
$R^5$ and $R^6$ are the same or different and each is a hydrogen atom, a $C_{1-6}$ alkyl group or a halogen atom, and
$R^7$ and $R^8$ are the same or different and each is a hydrogen atom, a $C_{1-6}$ alkyl group, a halogen atom or an optionally substituted hydroxy group,
or a salt thereof (except
4-[[3-(2-pyrazinyl)phenyl]methoxy]benzenepropanoic acid,
methyl 4-[[3-(2-pyrazinyl)phenyl]methoxy]benzenepropanoate,
methyl 4-[[3-[5-(trifluoromethyl)-2-pyridinyl]phenyl]methoxy]benzenepropanoate,
4-[[3-[5-(trifluoromethyl)-2-pyridinyl]phenyl]methoxy] benzenepropanoic acid,
4-[[3-(2-thiazolyl)phenyl]methoxy]benzenepropanoic acid,
methyl 4-[[3-(2-thiazolyl)phenyl]methoxy]benzenepropanoate,
4-[[3-(1H-pyrrol-1-yl)phenyl]methoxy]benzenepropanoic acid,
30 methyl 4-[[3-(1H-pyrrol-1-yl)phenyl]methoxy]benzenepropanoate,
4-[[3-(3-furyl)phenyl]methoxy]benzenepropanoic acid,
methyl 4-[[3-(3-furyl)phenyl]methoxy]benzenepropanoate,
4-[[3-(5-pyrimidinyl)phenyl]methoxy]benzenepropanoic acid,
4-[[3-(2-pyridinyl)phenyl]methoxy]benzenepropanoic acid,
methyl 4-[[3-(2-pyridinyl)phenyl]methoxy]benzenepropanoate,
4-[[3-(2-pyrimidinyl)phenyl]methoxy]benzenepropanoic acid, methyl 4-[[3-(2-pyrimidinyl)phenyl]methoxy]benzenepropanoate,
4-[[3-(2-thienyl)phenyl]methoxy]benzenepropanoic acid,
methyl 4-[[3-(2-thienyl)phenyl]methoxy]benzenepropanoate,
4-[[3-(2-thienyl)phenyl]methoxy]benzenepropanoic acid and methyl 4-[[3-(2-thienyl)phenyl]methoxy]benzenepropanoate) (hereinafter sometimes to be abbreviated as compound (I)).

[2] A prodrug of compound (I).
[3] Compound (I) wherein the heterocyclic group represented by Het is a heterocyclic group containing at least one nitrogen atom as a ring-constituting atom and the nitrogen atom is bonded to a group represented by the following formula:

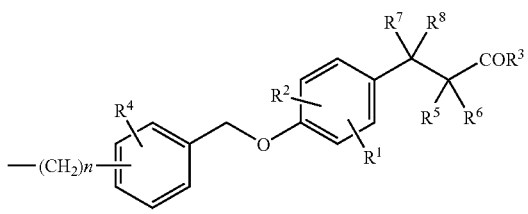

wherein each symbol is as defined in the above-mentioned [1].

[4] Compound (I) wherein $R^3$ is a hydroxy group.
[5] Compound (I) wherein n is 1.
[6] Compound (I) wherein $R^1$ and $R^2$ are the same or different and each is a hydrogen atom or a halogen atom.
[7] Compound (I) wherein $R^4$ is a hydrogen atom or a $C_{1-6}$ alkoxy group.
[8] Compound (I) wherein $R^5$ and $R^6$ are hydrogen atoms.
[9] Compound (I) wherein $R^7$ and $R^8$ are hydrogen atoms.
[10] Compound (I) which is 3-(4-{[3-(1-benzothiophen-3-yl)benzyl]oxy}phenyl)propanoic acid;
3-(4-{[3-(2-methyl-3,4-dihydroquinolin-1 (2H)-yl)benzyl]oxy}phenyl)propanoic acid;
3-[4-({4-[(2-phenyl-1H-indol-1-yl)methyl]benzyl}oxy)phenyl]propanoic acid;
3-[2-fluoro-4-({4-[(2-phenyl-1H-indol-1-yl)methyl]benzyl}oxy)phenyl]propanoic acid;
3-[4-({4-[(2,5-diphenyl-1H-pyrrol-1-yl)methyl]benzyl}oxy)phenyl]propanoic acid;
3-(4-{[4-({5-(2-phenylethyl)-3-[4-(trifluoromethyl)phenyl]-1H-pyrazol-1-yl}methyl)benzyl]oxy}phenyl)propanoic acid;
3-[4-({4-[(3,5-diphenyl-1H-pyrazol-1-yl)methyl]benzyl}oxy)phenyl]propanoic acid;
3-{4-[(4-{[3-tert-butyl-5-(phenoxymethyl)-1H-pyrazol-1-yl]methyl}benzyl)oxy]-2-fluorophenyl}propanoic acid;
3-{4-[(4-{[5-(benzyloxy)-3-tert-butyl-1H-pyrazol-1-yl]methyl}benzyl)oxy]-2-fluorophenyl}propanoic acid;
3-(4-{[4-({3-tert-butyl-5-[(6-methylpyridin-2-yl)methoxy]-1H-pyrazol-1-yl}methyl)benzyl]oxy}-2-fluorophenyl)propanoic acid or a salt thereof.

[11] A GPR40 receptor function modulator comprising compound (I) or a prodrug thereof.
[12] An insulin secretagogue comprising compound (I) or a prodrug thereof.
[13] A pharmaceutical agent comprising compound (I) or a prodrug thereof.
[14] A pharmaceutical agent of the above-mentioned [13], which is an agent for the prophylaxis or treatment of diabetes.
[15] Use of compound (I) or a prodrug thereof for the production of a GPR40 receptor function modulator.
[16] Use of compound (I) or a prodrug thereof for the production of an insulin secretagogue.
[17] Use of compound (I) or a prodrug thereof for the production of an agent for the prophylaxis or treatment of diabetes.
[18] A method of modulating a GPR40 receptor function in a mammal, which comprises administering an effective amount of compound (I) or a prodrug thereof to the mammal.
[19] A method of promoting insulin secretion in a mammal, which comprises administering an effective amount of compound (I) or a prodrug thereof to the mammal.
[20] A method for the prophylaxis or treatment of diabetes in a mammal, which comprises administering an effective amount of compound (I) or a prodrug thereof to the mammal.

DETAILED DESCRIPTION OF THE INVENTION

The compound of the present invention has a superior GPR40 receptor function modulating action and can be used as an agent for the prophylaxis or treatment of diabetes and the like, or as an insulin secretagogue.

BEST MODE FOR EMBODYING THE INVENTION

Unless otherwise specified, as the "halogen atom" in the present specification, a fluorine atom, a chlorine atom, a bromine atom and an iodine atom can be mentioned.

Unless otherwise specified, as the "optionally substituted hydrocarbon group" in the present specification, for example, an "optionally substituted $C_{1-6}$ alkyl group", an "optionally substituted $C_{2-6}$ alkenyl group", an "optionally substituted $C_{2-6}$ alkynyl group", an "optionally substituted $C_{3-8}$ cycloalkyl group", an "optionally substituted $C_{6-14}$ aryl group", an "optionally substituted $C_{7-16}$ aralkyl group" and the like can be mentioned.

Unless otherwise specified, as the "$C_{1-6}$ alkyl group" in the present specification, for example, methyl, ethyl, propyl, isopropyl, butyl, isobutyl, sec-butyl, tert-butyl, pentyl, isopentyl, neopentyl, hexyl and the like can be mentioned.

Unless otherwise specified, as the "$C_{2-6}$ alkenyl group" in the present specification, for example, vinyl, propenyl, isopropenyl, 2-buten-1-yl, 4-penten-1-yl, 5-hexen-1-yl and the like can be mentioned.

Unless otherwise specified, as the "$C_{2-6}$ alkynyl group" in the present specification, for example, 2-butyn-1-yl, 4-pentyn-1-yl, 5-hexyn-1-yl and the like can be mentioned.

Unless otherwise specified, as the "$C_{3-8}$ cycloalkyl group" in the present specification, for example, cyclopropyl, cyclobutyl, cyclopentyl, cyclohexyl and the like can be mentioned.

Unless otherwise specified, as the "$C_{6-14}$ aryl group" in the present specification, for example, phenyl, 1-naphthyl, 2-naphthyl, 2-biphenylyl, 3-biphenylyl, 4-biphenylyl, 2-anthryl and the like can be mentioned. The $C_{6-14}$ aryl may be saturated partially, and as the partially saturated $C_{6-14}$ aryl, for example, tetrahydronaphthyl and the like can be mentioned.

Unless otherwise specified, as the "$C_{7-16}$ aralkyl group" in the present specification, for example, benzyl, phenethyl, diphenylmethyl, 1-naphthylmethyl, 2-naphthylmethyl, 2,2- diphenylethyl, 3-phenylpropyl, 4-phenylbutyl, 5-phenylpentyl, 2-biphenylylmethyl, 3-biphenylylmethyl, 4-biphenylylmethyl and the like can be mentioned.

Unless otherwise specified, as the "optionally substituted-hydroxy group" in the present specification, for example, a "hydroxy group", an "optionally substituted $C_{1-10}$ alkoxy group", an "optionally substituted heterocyclyloxy group", an "optionally substituted $C_{6-14}$ aryloxy group", an "optionally substituted $C_{7-16}$ aralkyloxy group" and the like can be mentioned.

Unless otherwise specified, as the "$C_{1-6}$ alkoxy group" in the present specification, for example, methoxy, ethoxy, propoxy, isopropoxy, butoxy, isobutoxy, tert-butoxy, pentyloxy, hexyloxy and the like can be mentioned.

As the "$C_{1-10}$ alkoxy group" in the present specification, heptyloxy, octyloxy, nonyloxy, decyloxy and the like can be mentioned besides the above-mentioned $C_{1-6}$ alkoxy group.

Unless otherwise specified, as the "$C_{1-6}$ alkoxy-$C_{1-6}$ alkoxy group" in the present specification, for example, methoxymethoxy, methoxyethoxy, ethoxymethoxy, ethoxyethoxy and the like can be mentioned.

Unless otherwise specified, as the "$C_{1-6}$ alkylsulfonyl-$C_{1-6}$ alkoxy group" in the present specification, for example, methylsulfonylmethoxy, methylsulfonylethoxy, ethylsulfonylmethoxy, ethylsulfonylethoxy and the like can be mentioned.

As the "heterocyclyloxy group" in the present specification, a hydroxy group substituted by a "heterocyclic group" below can be mentioned. As preferable examples of the heterocyclyloxy group, tetrahydropyranyloxy, thiazolyloxy, pyridyloxy, pyrazolyloxy, oxazolyloxy, thienyloxy, furyloxy and the like can be mentioned.

Unless otherwise specified, as the "$C_{6-14}$ aryloxy group" in the present specification, for example, phenoxy, 1-naphthyloxy, 2-naphthyloxy and the like can be mentioned.

Unless otherwise specified, as the "$C_{7-16}$ aralkyloxy group" in the present specification, for example, benzyloxy, phenethyloxy and the like can be mentioned.

Unless otherwise specified, as the "optionally substituted mercapto group" in the present specification, for example, a "mercapto group", an "optionally substituted $C_{1-10}$ alkylthio group", an "optionally substituted heterocyclylthio group", an "optionally substituted $C_{6-14}$ arylthio group", an "optionally substituted $C_{7-16}$ aralkylthio group" and the like can be mentioned.

Unless otherwise specified, as the "$C_{1-6}$ alkylthio group" in the present specification, for example, methylthio, ethylthio, propylthio, isopropylthio, butylthio, sec-butylthio, tert-butylthio and the like can be mentioned.

As the "$C_{1-10}$ alkylthio group" in the present specification, heptylthio, octylthio, nonylthio, decylthio and the like can be mentioned besides the above-mentioned $C_{1-6}$ alkylthio group.

As the "heterocyclylthio group" in the present specification, a mercapto group substituted by a "heterocyclic group" below can be mentioned. As preferable examples of the heterocyclylthio group, tetrahydropyranylthio, thiazolylthio, pyridylthio, pyrazolylthio, oxazolylthio, thienylthio, furylthio and the like can be mentioned.

Unless otherwise specified, as the "$C_{6-14}$ arylthio group" in the present specification, for example, phenylthio, 1-naphthylthio, 2-naphthylthio and the like can be mentioned.

Unless otherwise specified, as the "$C_{7-16}$ aralkylthio group" in the present specification, for example, benzylthio, phenethylthio and the like can be mentioned.

Unless otherwise specified, as the "heterocyclic group" in the present specification, for example, a 5- to 14-membered (monocyclic, bicyclic or tricyclic) heterocyclic group containing, as a ring-constituting atom besides carbon atoms, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 14-membered non-aromatic heterocyclic group and the like can be mentioned. Of these, a 5- or 6-membered aromatic heterocyclic group is preferable.

Specifically, aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), quinolyl (e.g., 1-quinolyl, 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl (e.g., 2-pyrazinyl), pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl, 5-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl, 4-benzo[b]thienyl, 5-benzo[b]thienyl), benzo[b]furanyl (e.g., 2-benzo[b]furanyl, 3-benzo[b]furanyl, 5-benzo[b]furanyl), imidazo[1,2-a]pyridyl (e.g., imidazo[1,2-a]pyridin-2-yl) and the like;

non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), tetrahydropyranyl, tetrahydroquinolyl (e.g., 3,4-dihydro-1 (2H)-quinolinyl), tetrahydroisoquinolyl (e.g., 3,4-dihydro-2 (1H)-isoquinolinyl), 2,3-dihydro-1H-indolyl (e.g., 2,3-dihydro-1H-indol-1-yl), dihydroquinolyl (e.g., 1,2-dihydroquinolyl), 5,6,7,8-tetrahydro-4H-[1,3]thiazolo[5,4-b]azepinyl (e.g., 5,6,7,8-tetrahydro-4H-[1,3]thiazolo[5,4-b]azepin-4-yl), 3,4-dihydro-2H-1,5-benzothiazepinyl (e.g., 3,4-dihydro-1,5-benzothiazepin-5 (2H)-yl), 2,3,4,5-tetrahydro-1H-1-benzazepinyl (e.g., 2,3,4,5-tetrahydro-1H-1-benzazepin-1-yl) and the like, and the like can be mentioned.

Unless otherwise specified, as the "$C_{1-6}$ alkylsulfonyl group" in the present specification, for example, methylsulfonyl, ethylsulfonyl and the like can be mentioned.

Unless otherwise specified, as the "$C_{1-6}$ alkylsulfinyl group" in the present specification, for example, methylsulfinyl, ethylsulfinyl and the like can be mentioned.

Unless otherwise specified, as the "$C_{6-14}$ arylsulfonyl group" in the present specification, for example, phenylsulfonyl, 1-naphthylsulfonyl, 2-naphthylsulfonyl and the like can be mentioned.

Unless otherwise specified, as the "$C_{6-14}$ arylsulfinyl group" in the present specification, for example, phenylsulfinyl, 1-naphthylsulfinyl, 2-naphthylsulfinyl and the like can be mentioned.

Unless otherwise specified, as the "optionally esterified carboxyl group" in the present specification, for example, a carboxyl, a $C_{1-6}$ alkoxy-carbonyl group (e.g., methoxycarbonyl, ethoxycarbonyl, propoxycarbonyl, tert-butoxycarbonyl etc.), a $C_{6-14}$ aryloxy-carbonyl group (e.g., phenoxycarbonyl etc.), a $C_{7-16}$ aralkyloxy-carbonyl group (e.g., benzyloxycarbonyl, phenethyloxycarbonyl etc.) and the like can be mentioned.

Unless otherwise specified, as the "optionally halogenated $C_{1-6}$ alkyl group" in the present specification, the above-mentioned "$C_{1-6}$ alkyl group" optionally substituted by 1 to 5 above-mentioned "halogen atoms" can be mentioned. For example, methyl, ethyl, propyl, isopropyl, butyl, tert-butyl, isobutyl, trifluoromethyl and the like can be mentioned.

Unless otherwise specified, as the "optionally halogenated $C_{1-6}$ alkoxy group" in the present specification, the above-mentioned "$C_{1-6}$ alkoxy group" optionally substituted by 1 to 5 above-mentioned "halogen atoms" can be mentioned. For example, methoxy, ethoxy, isopropoxy, tert-butoxy, trifluoromethoxy and the like can be mentioned.

Unless otherwise specified, as the "mono- or di-$C_{1-6}$ alkyl-amino group" in the present specification, an amino group mono- or di-substituted by the above-mentioned "$C_{1-6}$ alkyl group(s)" can be mentioned. For example, methylamino, ethylamino, propylamino, dimethylamino, diethylamino and the like can be mentioned.

Unless otherwise specified, as the "mono- or di-$C_{6-14}$ aryl-amino group" in the present specification, an amino group mono- or di-substituted by the above-mentioned "$C_{6-14}$ aryl group(s)" can be mentioned. For example, phenylamino, diphenylamino, 1-naphthylamino, 2-naphthylamino and the like can be mentioned.

Unless otherwise specified, as the "mono- or di-$C_{7-16}$ aralkyl-amino group" in the present specification, an amino group mono- or di-substituted by the above-mentioned "$C_{7-16}$ aralkyl group(s)" can be mentioned. For example, benzylamino, phenethylamino and the like can be mentioned.

Unless otherwise specified, as the "N—$C_{1-6}$ alkyl-N—$C_{6-14}$ aryl-amino group" in the present specification, an amino group substituted by the above-mentioned "$C_{1-6}$ alkyl group" and the above-mentioned "$C_{6-14}$ aryl group" can be mentioned. For example, N-methyl-N-phenylamino, N-ethyl-N-phenylamino and the like can be mentioned.

Unless otherwise specified, as the "N—$C_{1-6}$ alkyl-N—$C_{7-16}$ aralkyl-amino group" in the present specification, an amino group substituted by the above-mentioned "$C_{1-6}$ alkyl group" and the above-mentioned "$C_{7-16}$ aralkyl group" can be mentioned. For example, N-methyl-N-benzylamino, N-ethyl-N-benzylamino, N-methyl-N-phenethylamino, N-ethyl-N-phenethylamino and the like can be mentioned.

Unless otherwise specified, as the "mono- or di-$C_{1-6}$ alkyl-carbamoyl group" in the present specification, a carbamoyl group mono- or di-substituted by the above-mentioned "$C_{1-6}$ alkyl group(s)" can be mentioned. For example, methylcarbamoyl, ethylcarbamoyl, dimethylcarbamoyl, diethylcarbamoyl, ethylmethylcarbamoyl and the like can be mentioned.

Unless otherwise specified, as the "mono- or di-$C_{6-14}$ aryl-carbamoyl group" in the present specification, a carbamoyl group mono- or di-substituted by the above-mentioned "$C_{6-14}$ aryl group(s)" can be mentioned. For example, phenylcarbamoyl, 1-naphthylcarbamoyl, 2-naphthylcarbamoyl and the like can be mentioned.

Unless otherwise specified, as the "mono- or di-5- to 7-membered heterocyclyl-carbamoyl group" in the present specification, a carbamoyl group mono- or di-substituted by 5- to 7-membered heterocyclic group(s) can be mentioned. As the 5- to 7-membered heterocyclic group, a 5- to 7-membered heterocyclic group containing, as a ring-constituting atom besides carbon atoms, one or two kinds of 1 to 4 hetero atoms selected from a nitrogen atom, a sulfur atom and an oxygen atom can be mentioned. As preferable examples of the "mono- or di-5 to 7-membered heterocyclyl-carbamoyl group", 2-pyridylcarbamoyl, 3-pyridylcarbamoyl, 4-pyridylcarbamoyl, 2-thienylcarbamoyl, 3-thienylcarbamoyl and the like can be mentioned.

Unless otherwise specified, as the "mono- or di-$C_{1-6}$ alkyl-sulfamoyl group" in the present specification, a sulfamoyl group mono- or di-substituted by the above-mentioned "$C_{1-6}$ alkyl group(s)" can be used. For example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, a sulfamoyl group mono- or di-substituted by the above-mentioned "$C_{6-14}$ aryl group(s)" can be used. For example, phenylsulfamoyl, diphenylsulfamoyl, 1-naphthylsulfamoyl, 2-naphthylsulfamoyl and the like can be mentioned.

As the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (containing optionally substituted $C_{1-6}$ alkoxy group)" and "optionally substituted $C_{1-10}$ alkylthio group (containing optionally substituted $C_{1-6}$ alkylthio group)" in the present specification, for example, a "$C_{1-6}$ alkyl group", a "$C_{2-6}$ alkenyl group", a "$C_{2-6}$ alkynyl group", a "$C_{1-10}$ alkoxy group (containing $C_{1-6}$ alkoxy group)" and a "$C_{1-10}$ alkylthio group (containing $C_{1-6}$ alkylthio group)", each of which optionally has 1 to 5 substituents at substitutable position(s) selected from (1) a halogen atom;
(2) a hydroxy group;
(3) an amino group;
(4) a nitro group;
(5) a cyano group;
(6) a heterocyclic group (preferably furyl, pyridyl, thienyl, pyrazolyl, thiazolyl, oxazolyl, pyrazinyl, benzimidazolyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;
(7) a mono- or di-$C_{1-6}$ alkyl-amino group;
(8) a mono- or di-$C_{6-14}$ aryl-amino group;
(9) a mono- or di-$C_{7-16}$ aralkyl-amino group;
(10) an N—$C_{1-6}$ alkyl-N—$C_{6-14}$ aryl-amino group;
(11) an N—$C_{1-6}$ alkyl-N—$C_{7-16}$ aralkyl-amino group;
(12) a $C_{3-8}$ cycloalkyl group;
(13) an optionally halogenated $C_{1-6}$ alkoxy group;
(14) a $C_{1-6}$ alkylthio group;
(15) a $C_{1-6}$ alkylsulfinyl group;
(16) a $C_{1-6}$ alkylsulfonyl group;
(17) an optionally esterified carboxyl group;
(18) a carbamoyl group;
(19) a thiocarbamoyl group;
(20) a mono- or di-$C_{1-6}$ alkyl-carbamoyl group;
(21) a mono- or di-$C_{6-14}$ aryl-carbamoyl group;
(22) a mono- or di-5- to 7-membered heterocyclyl-carbamoyl group;

(23) a $C_{1-6}$ alkyl-carbonylamino group (e.g., acetylamino, propionylamino) optionally substituted by carboxyl group(s);

(24) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(25) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(26) a heterocyclyloxy group;

(27) a sulfamoyl group;

(28) a mono- or di-$C_{1-6}$ alkyl-sulfamoyl group;

(29) a mono- or di-$C_{6-14}$ aryl-sulfamoyl group;

(30) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(31) a $C_{6-14}$ arylsulfonyl group; and the like, can be mentioned.

As the "optionally substituted $C_{3-8}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylthio group", "optionally substituted $C_{6-14}$ arylthio group" and "optionally substituted $C_{7-16}$ aralkylthio group" in the present specification, for example, a "$C_{3-8}$ cycloalkyl group", a "$C_{6-14}$ aryl group", a "$C_{7-16}$ aralkyl group", a "heterocyclic group", a "heterocyclyloxy group", a "$C_{6-14}$ aryloxy group", a "$C_{7-16}$ aralkyloxy group", a "heterocyclylthio group", a "$C_{6-14}$ arylthio group" and a "$C_{7-16}$ aralkylthio group", each of which optionally has 1 to 5 substituents at substitutable position(s) selected from (1) a halogen atom;

(2) a hydroxy group;

(3) an amino group;

(4) a nitro group;

(5) a cyano group;

(6) an optionally substituted $C_{1-6}$ alkyl group;

(7) an optionally substituted $C_{2-6}$ alkenyl group;

(8) an optionally substituted $C_{2-6}$ alkynyl group;

(9) a $C_{6-14}$ aryl group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(10) a $C_{6-14}$ aryloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(11) a $C_{7-16}$ aralkyloxy group optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(12) a heterocyclic group (preferably furyl, pyridyl, thienyl, pyrazolyl, thiazolyl, oxazolyl, pyrazinyl, benzimidazolyl) optionally substituted by 1 to 3 substituents selected from a halogen atom, a hydroxy group, an amino group, a nitro group, a cyano group, an optionally halogenated $C_{1-6}$ alkyl group, a mono- or di-$C_{1-6}$ alkyl-amino group, a $C_{6-14}$ aryl group, a mono- or di-$C_{6-14}$ aryl-amino group, a $C_{3-8}$ cycloalkyl group, a $C_{1-6}$ alkoxy group, a $C_{1-6}$ alkoxy-$C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylsulfonyl-$C_{1-6}$ alkoxy group, an optionally esterified carboxyl group, a carbamoyl group, a thiocarbamoyl group, a mono- or di-$C_{1-6}$ alkyl-carbamoyl group, a mono- or di-$C_{6-14}$ aryl-carbamoyl group, a sulfamoyl group, a mono- or di-$C_{1-6}$ alkyl-sulfamoyl group and a mono- or di-$C_{6-14}$ aryl-sulfamoyl group;

(13) a mono- or di-$C_{1-6}$ alkyl-amino group;
(14) a mono- or di-$C_{6-14}$ aryl-amino group;
(15) a mono- or di-$C_{7-16}$ aralkyl-amino group;
(16) an N—$C_{1-6}$ alkyl-N—$C_{6-14}$ aryl-amino group;
(17) an N—$C_{1-6}$ alkyl-N—$C_{7-16}$ aralkyl-amino group;
(18) a $C_{3-8}$ cycloalkyl group;
(19) an optionally substituted $C_{1-6}$ alkoxy group;
(20) a $C_{1-6}$ alkylthio group;
(21) a $C_{1-6}$ alkylsulfinyl group;
(22) a $C_{1-6}$ alkylsulfonyl group;
(23) an optionally esterified carboxyl group;
(24) a carbamoyl group;
(25) a thiocarbamoyl group;
(26) a mono- or di-$C_{1-6}$ alkyl-carbamoyl group;
(27) a mono- or di-$C_{6-14}$ aryl-carbamoyl group;
(28) a mono- or di-5- to 7-membered heterocyclyl-carbamoyl group;
(29) a sulfamoyl group;
(30) a mono- or di-$C_{1-6}$ alkyl-sulfamoyl group;
(31) a mono- or di-$C_{6-14}$ aryl-sulfamoyl group;
(32) a $C_{6-14}$ arylsulfonyl group; and the like, can be mentioned.

Unless otherwise specified, as the "optionally substituted amino group" in the present specification, an amino group optionally substituted by 1 or 2 substituents selected from
(1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-8}$ cycloalkyl group;
(5) an optionally substituted $C_{6-14}$ aryl group;
(6) an optionally substituted $C_{1-6}$ alkoxy group;
(7) an optionally substituted acyl group;
(8) an optionally substituted heterocyclic group (preferably furyl, pyridyl, thienyl, pyrazolyl, thiazolyl, oxazolyl); and the like, can be mentioned. When the "optionally substituted amino group" is an amino group substituted by 2 substituents, these substituents may form a nitrogen-containing heterocycle together with the adjacent nitrogen atom. As the "nitrogen-containing heterocycle", for example, a 5- to 7-membered nitrogen-containing heterocycle containing, as a ring-constituting atom besides carbon atoms, at least one nitrogen atom and optionally further containing 1 or 2 hetero atoms selected from an oxygen atom, a sulfur atom and a nitrogen atom can be mentioned. As preferable examples of the nitrogen-containing heterocycle, pyrrolidine, imidazolidine, pyrazolidine, piperidine, piperazine, morpholine, thiomorpholine, thiazolidine, oxazolidine and the like can be mentioned.

Unless otherwise specified, as the "optionally substituted acyl group" in the present specification, groups represented by the formulas: —$COR^9$, —CO—$OR^9$, —$SO_2R^9$, —$SOR^9$, —PO($OR^9$)($OR^{10}$), —$CONR^{9a}R^{10a}$, —CS—$NR^{9a}R^{10a}$ and $SO_2$—$NR^{9a}R^{10a}$ wherein $R^{9a}$ and $R^{10}$ are the same or different and each is a hydrogen atom, an optionally substituted hydrocarbon group or an optionally substituted heterocyclic group, and $R^{9a}$ and $R^{10a}$ are the same or different and each is a hydrogen atom, an optionally substituted hydrocarbon group or an optionally substituted heterocyclic group, or $R^{9a}$ and $R^{10a}$ may form an optionally substituted nitrogen-containing heterocycle together with the adjacent nitrogen atom, and the like can be mentioned.

As the "nitrogen-containing heterocycle" of the "optionally substituted nitrogen-containing heterocycle" which $R^{9a}$ and $R^{10a}$ form together with the adjacent nitrogen atom, for example, a 5- to 7-membered nitrogen-containing heterocycle containing, as a ring-constituting atom besides carbon atoms, at least one nitrogen atom and optionally further containing 1 to 2 hetero atoms selected from an oxygen atom, a sulfur atom and a nitrogen atom can be mentioned. As preferable examples of the "nitrogen-containing heterocycle", pyrrolidine, imidazolidine, pyrazolidine, piperidine, piperazine, morpholine, thiomorpholine, thiazolidine, oxazolidine and the like can be mentioned.

The nitrogen-containing heterocycle optionally has 1 to 2 substituents at substitutable position (s). As these substituents, a hydroxy group, an optionally halogenated $C_{1-6}$ alkyl group, a $C_{6-14}$ aryl group, a $C_{7-16}$ aralkyl group and the like can be mentioned.

As preferable examples of the "optionally substituted acyl group",
a formyl group;
a carboxyl group;
a carbamoyl group;
a $C_{1-6}$ alkyl-carbonyl group (e.g., acetyl, isobutanoyl, isopentanoyl);
a $C_{1-6}$ alkoxy-carbonyl group (e.g., methoxycarbonyl, ethoxycarbonyl, propoxycarbonyl, tert-butoxycarbonyl);
a $C_{3-8}$ cycloalkyl-carbonyl group (e.g., cyclopentylcarbonyl, cyclohexylcarbonyl);
a $C_{6-14}$ aryl-carbonyl group (e.g., benzoyl, 1-naphthoyl, 2-naphthoyl);
a $C_{7-16}$ aralkyl-carbonyl group (e.g., phenylacetyl, 2-phenylpropanoyl);
a $C_{6-14}$ aryloxy-carbonyl group (e.g., phenyloxycarbonyl, naphthyloxycarbonyl);
a $C_{7-16}$ aralkyloxy-carbonyl group (e.g., benzyloxycarbonyl, phenethyloxycarbonyl);
a mono- or di-$C_{1-6}$ alkylcarbamoyl group;
a mono- or di-$C_{6-14}$ aryl-carbamoyl group;
a mono- or di-$C_{3-8}$ cycloalkyl-carbamoyl group (e.g., cyclopropylcarbamoyl);
a mono- or di-$C_{7-16}$ aralkyl-carbamoyl group (e.g., benzylcarbamoyl);
$C_{1-6}$ alkylsulfonyl group;
$C_{6-14}$ arylsulfonyl group (e.g., phenylsulfonyl) optionally substituted by nitro group(s);
a heterocycle (preferably nitrogen-containing heterocycle)-carbonyl group (e.g., pyrrolidinylcarbonyl, piperidinocarbonyl);
a $C_{1-6}$ alkylsulfinyl group;
a $C_{6-14}$ arylsulfinyl group;
a thiocarbamoyl group;
a sulfamoyl group;
a mono- or di-$C_{1-6}$ alkyl-sulfamoyl group;
a mono- or di-$C_{6-14}$ aryl-sulfamoyl group;
a mono- or di-$C_{7-16}$ aralkyl-sulfamoyl group (e.g., benzylsulfamoyl)
and the like can be mentioned.

The definition of each symbol in the formula (I) is described in detail in the following.

Het is an optionally substituted heterocyclic group. When the heterocyclic group represented by Het is a heterocyclic group containing at least one nitrogen atom as a ring-constituting atom, the nitrogen atom is preferably bonded to a group represented by the following formula:

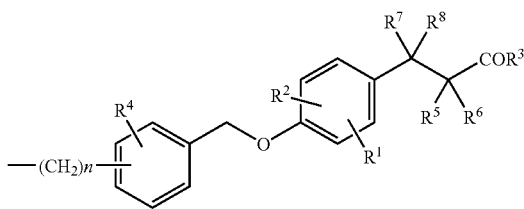

wherein each symbol is as defined above.

As the "heterocyclic group" for Het, thienyl, furyl, pyrrolyl, imidazolyl, pyrazolyl, indolyl, benzimidazolyl, benzo[b]thienyl, pyrrolidinyl, piperidinyl, piperazinyl, morpholinyl, tetrahydroquinolyl, tetrahydroisoquinolyl, 2,3-dihydro-1H-indolyl, 1,2-dihydroquinolyl, 5,6,7,8-tetrahydro-4H-[1,3]thiazolo[5,4-b]azepinyl, 3,4-dihydro-2H-1,5-benzothiazepinyl, 2,3,4,5-tetrahydro-1H-1-benzazepinyl and the like are preferable. Of these, pyrrolyl, pyrazolyl, indolyl, benzo[b]thienyl, tetrahydroquinolyl (e.g., 3,4-dihydro-1 (2H)-quinolinyl) and the like are preferable.

As the above-mentioned "heterocyclic group containing at least one nitrogen atom as a ring-constituting atom", pyrrolyl, imidazolyl, pyrazolyl, indolyl, benzimidazolyl, pyrrolidinyl, piperidinyl, piperazinyl, morpholinyl, tetrahydroquinolyl, tetrahydroisoquinolyl, 2,3-dihydro-1H-indolyl, 1,2-dihydroquinolyl, 5,6,7,8-tetrahydro-4H-[1,3]thiazolo[5,4-b]azepinyl, 3,4-dihydro-2H-1,5-benzothiazepinyl, 2,3,4,5-tetrahydro-1H-1-benzazepinyl and the like are preferable. Of these, pyrrolyl, pyrazolyl, indolyl, tetrahydroquinolyl (e.g., 3,4-dihydro-1 (2H)-quinolinyl) and the like are preferable.

As preferable substituents of the "heterocyclic group",
(1) a halogen atom;
(2) an optionally substituted $C_{1-6}$ alkyl group [preferably, a $C_{1-6}$ alkyl group optionally substituted by 1 to 3 substituents selected from a halogen atom; a cyano group; a heterocyclic group (preferably, pyridyl); an optionally halogenated $C_{1-6}$ alkoxy group; a $C_{6-14}$ aryloxy group optionally substituted by optionally halogenated $C_{1-6}$ alkyl group(s); a $C_{6-14}$ aryl group optionally substituted by 1 to 3 halogen atoms; and a $C_{6-14}$ arylsulfonyl group];
(3) an optionally substituted $C_{2-6}$ alkenyl group (preferably, a $C_{2-6}$ alkenyl group optionally substituted by $C_{6-14}$ aryl group(s));
(4) a $C_{6-14}$ aryl group optionally substituted by 1 to 3 substituents selected from a cyano group, a halogen atom and an optionally halogenated $C_{1-6}$ alkyl group;
(5) a $C_{6-14}$ aryloxy group optionally substituted by 1 to 3 substituents selected from a halogen atom and an optionally halogenated $C_{1-6}$ alkyl group;
(6) a heterocyclic group (preferably, pyrazinyl, benzimidazolyl);
(7) a $C_{3-8}$ cycloalkyl group;
(8) a hydroxy group;
(9) an optionally substituted $C_{1-6}$ alkoxy group [preferably, a $C_{1-6}$ alkoxy group optionally substituted by 1 to 3 substituents selected from a $C_{1-6}$ alkoxy group, a $C_{1-6}$ alkylsulfonyl group, a $C_{6-14}$ aryl group and a heterocyclic group optionally substituted by $C_{1-6}$ alkyl group(s) (preferably, 6-methyl-pyridin-2-yl)];
(10) an optionally esterified carboxyl group (preferably, a $C_{1-6}$ alkoxy-carbonyl group);
(11) a $C_{6-14}$ arylsulfonyl group and the like can be mentioned.

The number of these substituents is preferably 1 to 3.

In compound (I), the position of Het-$(CH_2)n$- on the benzene ring is preferably the 2-position, the 3-position or the 4-position, more preferably the 3-position or the 4-position, and particularly preferably the 4-position.

n is 0 or 1.

$R^1$ and $R^2$ are the same or different and each is a hydrogen atom, a $C_{1-6}$ alkyl group or a halogen atom. Of these, a hydrogen atom and a halogen atom (preferably a fluorine atom) are preferable.

In compound (I), the position of $R^1$ and $R^2$ on the benzene ring is preferably adjacent to a group represented by the formula:

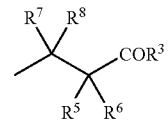

wherein each symbol is as defined above.

$R^3$ is an optionally substituted hydroxy group or an optionally substituted amino group. $R^3$ is preferably a hydroxy group; a $C_{1-6}$ alkoxy group; an amino group; a mono- or di-$C_{1-6}$ alkyl-amino group optionally substituted by cyano group(s); and the like. Of these, a hydroxy group is preferable.

$R^4$ is a hydrogen atom, an optionally substituted hydrocarbon group, an optionally substituted hydroxy group or an optionally substituted amino group. Of these, a hydrogen atom and a $C_{1-6}$ alkoxy group are preferable.

In compound (I), the position of $R^4$ on the benzene ring is not particularly limited.

$R^5$ and $R^6$ are the same or different and each is a hydrogen atom, a $C_{1-6}$ alkyl group or a halogen atom. Of these, a hydrogen atom is preferable.

$R^7$ and $R^8$ are the same or different and each is a hydrogen atom, a $C_{1-6}$ alkyl group, a halogen atom or an optionally substituted hydroxy group. Of these, a hydrogen atom is preferable.

However, compound (I) does not include
4-[[3-(2-pyrazinyl)phenyl]methoxy]benzenepropanoic acid,
methyl 4-[[3-(2-pyrazinyl)phenyl]methoxy]benzenepropanoate,
methyl 4-[[3-[5-(trifluoromethyl)-2-pyridinyl]phenyl]methoxy]benzenepropanoate,
4-[[3-[5-(trifluoromethyl)-2-pyridinyl]phenyl]methoxy]benzenepropanoic acid,
4-[[3-(2-thiazolyl)phenyl]methoxy]benzenepropanoic acid,
methyl 4-[[3-(2-thiazolyl)phenyl]methoxy]benzenepropanoate,
4-[[3-(1H-pyrrol-1-yl)phenyl]methoxy]benzenepropanoic acid,
methyl 4-[[3-(1H-pyrrol-1-yl)phenyl]methoxy]benzenepropanoate,
4-[[3-(3-furyl)phenyl]methoxy]benzenepropanoic acid,
methyl 4-[[3-(3-furyl)phenyl]methoxy]benzenepropanoate,
4-[[3-(5-pyrimidinyl)phenyl]methoxy]benzenepropanoic acid,
4-[[3-(2-pyridinyl)phenyl]methoxy]benzenepropanoic acid,
methyl 4-[[3-(2-pyridinyl)phenyl]methoxy]benzenepropanoate,
4-[[3-(2-pyrimidinyl)phenyl]methoxy]benzenepropanoic acid,
methyl 4-[[3-(2-pyrimidinyl)phenyl]methoxy]benzenepropanoate,
4-[[3-(2-thienyl)phenyl]methoxy]benzenepropanoic acid,
methyl 4-[[3-(2-thienyl)phenyl]methoxy]benzenepropanoate, 4-[[3-(2-thienyl)phenyl]methoxy]benzenepropanoic acid and methyl 4-[[3-(2-thienyl)phenyl]methoxy]benzenepropanoate.

As preferable examples of a compound represented by the formula (I), the following compounds can be mentioned.

[Compound A]

A compound wherein Het is thienyl, furyl, pyrrolyl, imidazolyl, pyrazolyl, indolyl, benzimidazolyl, benzo[b]thienyl, pyrrolidinyl, piperidinyl, piperazinyl, morpholinyl, tetrahydroquinolyl, tetrahydroisoquinolyl, 2,3-dihydro-1H-indolyl, 1,2-dihydroquinolyl, 5,6,7,8-tetrahydro-4H-[1,3]thiazolo[5,4-b]azepinyl, 3,4-dihydro-2H-1,5-benzothiazepinyl or 2,3,4,5-tetrahydro-1H-1-benzazepinyl, each optionally substituted by 1 to 3 substituents selected from (1) a halogen atom; (2) an optionally substituted $C_{1-6}$ alkyl group [preferably, a $C_{1-6}$ alkyl group optionally substituted by 1 to 3 substituents selected from a halogen atom; a cyano group; a heterocyclic group (preferably, pyridyl); an optionally halogenated $C_{1-6}$ alkoxy group; a $C_{6-14}$ aryloxy group optionally substituted by optionally halogenated $C_{1-6}$ alkyl group(s); a $C_{6-14}$ aryl group optionally substituted by 1 to 3 halogen atoms; and a $C_{6-14}$ arylsulfonyl group]; (3) an optionally substituted $C_{2-6}$ alkenyl group (preferably, a $C_{2-6}$ alkenyl group optionally substituted by $C_{6-14}$ aryl group(s)); (4) a $C_{6-14}$ aryl group optionally substituted by 1 to 3 substituents selected from a cyano group, a halogen atom and an optionally halogenated $C_{1-6}$ alkyl group; (5) a $C_{6-14}$ aryloxy group optionally substituted by 1 to 3 substituents selected from a halogen atom and an optionally halogenated $C_{1-6}$ alkyl group; (6) a heterocyclic group (preferably, pyrazinyl, benzimidazolyl); (7) a $C_{3-8}$ cycloalkyl group; (8) a hydroxy group; (9) an optionally substituted $C_{1-6}$ alkoxy group [preferably, a $C_{1-6}$ alkoxy group optionally substituted by 1 to 3 substituents selected from a $C_{1-6}$ alkoxy group, a $C_{1-6}$ alkylsulfonyl group, a $C_{6-14}$ aryl group and a heterocyclic group optionally substituted by $C_{1-6}$ alkyl group(s) (preferably, 6-methyl-pyridin-2-yl)]; (10) an optionally esterified carboxyl group (preferably, a $C_{1-6}$ alkoxy-carbonyl group); and (11) a $C_{6-14}$ arylsulfonyl group;

n is 0 or 1;

$R^1$ and $R^2$ are the same or different and each is a hydrogen atom or a halogen atom (preferably a fluorine atom);

$R^3$ is a hydroxy group or a $C_{1-6}$ alkoxy group (preferably a hydroxy group);

$R^4$ is a hydrogen atom or a $C_{1-6}$ alkoxy group; and $R^5$, $R^6$, $R^7$ and $R^8$ are hydrogen atoms.

[Compound B]

3-(4-{[3-(1-benzothiophen-3-yl)benzyl]oxy}phenyl)propanoic acid (Example 6);

3-(4-{[3-(2-methyl-3,4-dihydroquinolin-1 (2H)-yl)benzyl]oxy}phenyl)propanoic acid (Example 40);

3-[4-({4-[(2-phenyl-1H-indol-1-yl)methyl]benzyl}oxy)phenyl]propanoic acid (Example 45);

3-[2-fluoro-4-([4-[(2-phenyl-1H-indol-1-yl)methyl]benzyl)oxy)phenyl]propanoic acid (Example 46);

3-[4-({4-[(2,5-diphenyl-1H-pyrrol-1-yl)methyl]benzyl}oxy)phenyl]propanoic acid (Example 62);

3-(4-{[4-({5-(2-phenylethyl)-3-[4-(trifluoromethyl)phenyl]-1H-pyrazol-1-yl}methyl)benzyl]oxy}phenyl)propanoic acid (Example 65);

3-[4-({4-[(3,5-diphenyl-1H-pyrazol-1-yl)methyl]benzyl}oxy)phenyl]propanoic acid (Example 69);

3-{4-[(4-{[3-tert-butyl-5-(phenoxymethyl)-1H-pyrazol-1-yl]methyl}benzyl)oxy]-2-fluorophenyl}propanoic acid calcium salt (Example 131);

3-(4-[(4-({5-(benzyloxy)-3-tert-butyl-1H-pyrazol-1-yl]methyl}benzyl)oxy]-2-fluorophenyl)propanoic acid calcium salt (Example 133); and 3-(4-{[4-({3-tert-butyl-5-[(6-methylpyridin-2-yl)methoxy]-1H-pyrazol-1-yl}methyl)benzyl]oxy}-2-fluorophenyl)propanoic acid calcium salt (Example 137).

As a salt of compound (I) of the present invention, for example, metal salts, an ammonium salt, salts with organic bases, salts with inorganic acids, salts with organic acids, salts with basic or acidic amino acids and the like.

Here, preferable examples of the metal salt include alkali metal salts such as sodium salt, potassium salt and the like; alkaline earth metal salts such as calcium salt, magnesium salt, barium salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like. Preferable examples of the salt with acidic amino acid include a salt with aspartic acid, glutamic acid and the like.

Of these, a pharmacologically acceptable salt is preferable. For example, when compound (I) has an acidic functional group, metal salts such as alkali metal salts, alkaline earth metal salts and the like; an ammonium salt and the like are preferable, and when compound (I) has a basic functional group, salts with inorganic acid and salts with organic acid are preferable.

A prodrug of compound (I) is a compound that converts to compound (I) due to the reaction by enzyme, gastric acid and the like under the physiological conditions in the body; that is, a compound that converts to compound (I) by enzymatic oxidation, reduction, hydrolysis and the like, and a compound that converts to compound (I) by hydrolysis and the like by gastric acid and the like.

Examples of the prodrug of compound (I) include a compound wherein an amino group of compound (I) is acylated, alkylated or phosphorylated (e.g., compound where an amino group of compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated, and the like); a compound wherein a hydroxy group of compound (I) is acylated, alkylated, phosphorylated or borated (e.g., a compound where a hydroxy group of compound (I) is acetylated, palmitoylated, propanoylated, pivaloylated, succinylated, fumarylated, alanylated or dimethylaminomethylcarbonylated, and the like); a compound wherein a carboxy group of compound (I) is esterified or amidated (e.g., a compound where a carboxy group of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated, and the like) and the like. Of these, a compound wherein a carboxy group of compound (I) is esterified by $C_{1-6}$ alkyl group such as methyl, ethyl, tert-butyl and the like is preferable. These compounds can be produced from compound (I) by a method known per se.

A prodrug of compound (I) may be a compound that converts to compound (I) under physiological conditions as described in *Development of Pharmaceutical Products*, vol. 7, Molecule Design, pp. 163-198, Hirokawa Shoten (1990).

Hereinafter the production methods of compound (I) are explained.

Each symbol in the following schemes is as defined above unless particularly described. Each compound described in the schemes may form a salt as long as it does not inhibit the reaction, and as such salt, those similar to the salts of compound (I) can be mentioned.

The compound obtained in each of the following steps can also be used as a crude product in the form of a reaction mixture in the next reaction, or can be isolated from the reaction mixture according to a conventional method, and further purified easily by a separation method such as recrystallization, distillation, chromatography and the like.

Compound (I) can be produced, for example, by the methods in the following Schemes 1-4.

Compound (I) (e.g., compounds represented by the following formulas (Ia), (Ib) and (Ic) (to be abbreviated as compound (Ia), compound (Ib), and compound (Ic), respectively)) can be produced, for example, according to the method shown in the following Scheme 1 or a method analogous thereto.

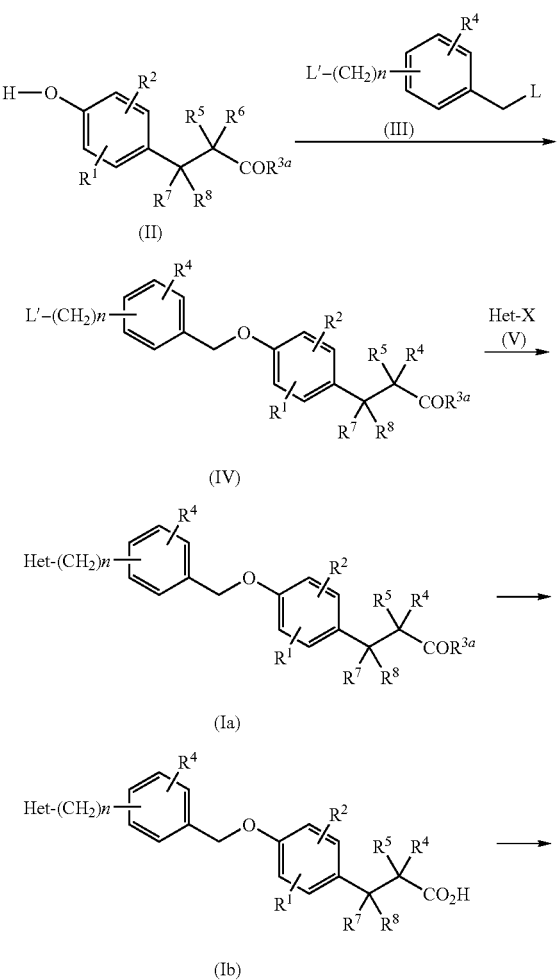

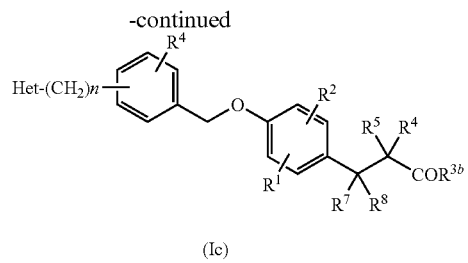

wherein $R^{3a}$ is an optionally substituted $C_{1-6}$ alkoxy group, $R^{3b}$ is an optionally substituted $C_{1-6}$ alkoxy group or an optionally substituted amino group, L is a leaving group or a hydroxy group, L' is a leaving group, X is a hydrogen atom or a metal (e.g., potassium, sodium, lithium, magnesium, copper, mercury, zinc, thallium, boron, tin and the like, which may be complexed) (when X is a hydrogen atom, then Het is a heterocycle containing at least one nitrogen atom as a ring-constituting atom, and the nitrogen atom and X are bonded), and other symbols are as defined above.

As "the leaving group" for L or L', for example, a halogen atom, an optionally halogenated $C_{1-6}$ alkylsulfonyloxy group (e.g., methanesulfonyloxy, ethanesulfonyloxy, trichloromethanesulfonyloxy, trifluoromethanesulfonyloxy), a $C_{6-10}$ arylsulfonyloxy group optionally having substituent(s) (e.g., a $C_{6-10}$ arylsulfonyloxy group (e.g., phenylsulfonyloxy, naphthylsulfonyloxy) optionally having 1 to 3 substituents selected from a $C_{1-6}$ alkyl group, a $C_{1-6}$ alkoxy group and a nitro group, and the like; as specific examples, phenylsulfonyloxy group, m-nitrophenylsulfonyloxy group, p-toluenesulfonyloxy group and the like) and the like can be mentioned.

Compounds represented by the formulas (II), (III) and (V) (to be abbreviated as compound (II), compound (III) and compound (V), respectively) can be easily obtained as commercially available products, or can also be produced according to a method known per se or a method analogous thereto.

A compound represented by the formula (IV) (to be abbreviated as compound (IV)) can be produced by reacting compound (II) with compound (III).

(i) When L is a hydroxy group, compound (IV) can be produced by subjecting compound (II) and compound (III) to the Mitsunobu reaction (*Synthesis*, 1981, pp. 1-27). In this reaction, compound (II) is reacted with compound (III) in the presence of azodicarboxylates such as diethyl azodicarboxylate, diisopropyl azodicarboxylate, 1,1'-(azodicarbonyl)dipiperidine and the like and phosphines such as triphenylphosphine, tributylphosphine and the like.

This reaction is advantageously carried out using a solvent inert to the reaction. While the solvent is not particularly limited as long as the reaction proceeds, for example, solvents including ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like, and the like, a mixed solvent thereof and the like are preferable.

The reaction time is generally about 5 min to about 48 hr, preferably about 10 min to about 24 hr. The reaction temperature is generally about −20° C. to about 200° C., preferably about 0° C. to about 100° C.

The amount of compound (III) to be used is about 0.8 to about 5 mol, preferably about 0.9 to about 2 mol, per 1 mol of compound (II).

The amount of each of the "azodicarboxylates" and "phosphines" to be used is about 1 to about 5 mol, preferably about 1 to about 2 mol, per 1 mol of compound (II).

(ii) When L is a leaving group, compound (IV) can be produced by reacting compound (II) with compound (III) in the presence of a base.

As the base, for example, alkali metal hydroxides such as sodium hydroxide, potassium hydroxide, lithium hydroxide and the like; alkaline earth metal hydroxides such as magnesium hydroxide, calcium hydroxide, barium hydroxide and the like; alkali metal carbonates such as sodium carbonate, potassium carbonate, cesium carbonate and the like; alkali metal hydrogencarbonates such as sodium hydrogencarbonate and the like; acetates such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-ethylmorpholine and the like; alkali metal hydrides such as sodium hydride, potassium hydride and the like; metal amides such as sodium amide, lithium diisopropylamide, lithium hexamethyldisilazide and the like; alkali metal $C_{1-6}$ alkoxides such as sodium methoxide, sodium ethoxide, sodium tert-butoxide, potassium tert-butoxide and the like, and the like can be mentioned.

This reaction is advantageously carried out using a solvent inert to the reaction. The solvent is not particularly limited as long as the reaction proceeds and, for example, solvents including ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; nitrites such as acetonitrile, propionitrile and the like; esters such as methyl acetate, ethyl acetate, butyl acetate and the like; sulfoxides such as dimethyl sulfoxide and the like; water and the like, a mixed solvent thereof and the like are preferable.

The amount of compound (III) to be used is about 0.8 to about 10 mol, preferably about 0.9 to about 2 mol, per 1 mol of compound (II). The amount of the base to be used is about 1 to about 10 mol, preferably about 1 to about 3 mol, per 1 mol of compound (II).

The reaction time is generally about 5 min to about 48 hr, preferably about 10 min to about 24 hr. The reaction temperature is generally about −50° C. to about 150° C., preferably about −20° C. to about 100° C.

Compound (Ia) can be produced by reacting compound (IV) with compound (V) (hereinafter a compound (V) wherein X is a hydrogen atom is referred to as compound (V-1) and a compound (V) wherein X is a metal is referred to as compound (V-2)).

The reaction of compound (IV) with compound (V) is generally carried out in the presence of a base. As the base, for example, alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogencarbonates such as sodium hydrogencarbonate, potassium hydrogencarbonate and the like; alkali metal $C_{1-6}$ alkoxides such as sodium methoxide, sodium ethoxide, sodium tert-butoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; metal amides such as sodium amide, lithium diisopropylamide, lithium hexamethyldisilazide and the like, and the like can be mentioned.

The reaction of compound (IV) with compound (V) is advantageously carried out using a solvent inert to the reaction. While the solvent is not particularly limited as long as the reaction proceeds, for example, solvents including alcohols such as methanol, ethanol, 1-propanol, 2-propanol, 1-butanol, tert-butanol and the like; ethers such as 1,4-dioxane, tetrahydrofuran, diethyl ether, tert-butyl methyl ether, diisopropyl ether, 1,2-dimethoxyethane, ethylene glycoldimethyl ether and the like; esters such as ethyl formate, ethyl acetate, butyl acetate and the like; halogenated hydrocarbons such as dichloromethane, chloroform, carbon tetrachloride, trichloroethylene and the like; hydrocarbons such as hexane, benzene, toluene and the like; amides such as formamide, N,N-dimethylformamide, N,N-dimethylacetamide and the like; nitriles such as acetonitrile, propionitrile and the like; sulfoxides such as dimethyl sulfoxide and the like; sulfolane; hexamethylphosphoramide; water and the like, a mixed solvent thereof and the like are preferable.

The reaction of compound (IV) with compound (V) can also be promoted by the use of a metal catalyst.

As the metal catalyst, metal complexes having various ligands are used and, for example, palladium compound [e.g., palladium(II) acetate, tetrakis(triphenylphosphine)palladium (0), bis(triphenylphosphine)palladium(II) dichloride, dichlorobis(triethylphosphine)palladium(0), tris(dibenzylideneacetone)dipalladium-2,2'-bis(diphenylphosphino)-1,1'-binaphthyl, complex of palladium(II) acetate and 1,1'-bis (diphenylphosphino)ferrocene, and the like], nickel compound [e.g., tetrakis(triphenylphosphine)nickel(0), bis (triethylphosphine)nickel(II) dichloride, bis(triphenylphosphine)nickel(II) dichloride and the like], rhodium compound [e.g., tris(triphenylphosphine)rhodium(III) trichloride and the like], cobalt compound, copper compound [e.g., copper oxide, copper(II) dichloride and the like], platinum compound and the like can be mentioned. Of these, palladium compound, nickel compound and copper compound are preferable. The amount of the metal catalyst to be used is about 0.000001 to about 5 mol, preferably about 0.0001 to about 1 mol, per 1 mol of compound (IV). When a metal catalyst unstable to oxygen is used in this reaction, the reaction is preferably carried out in an inert gas stream (e.g., argon gas or nitrogen gas).

The amount of compound (V) to be used is about 0.8 to about 10 mol, preferably about 0.9 to about 2 mol, per 1 mol of compound (IV). The amount of the base to be used is about 1 to about 20 mol, preferably about 1 to about 5 mol, per 1 mol of compound (IV).

The reaction temperature is generally about −10° C. to about 250° C., preferably about 0° C. to about 150° C.

While the reaction time varies depending on the kind of compound (IV), compound (V), metal catalyst, base or solvent, reaction temperature and the like, it is generally about 1 min to about 200 hr, preferably about 5 min to about 100 hr.

Compound (Ib) can be produced by subjecting compound (Ia) to hydrolysis reaction. The hydrolysis reaction is carried out using an acid or a base according to a conventional method.

As the acid, for example, mineral acids such as hydrochloric acid, sulfuric acid and the like; Lewis acids such as boron trichloride, boron tribromide and the like; organic acids such as trifluoroacetic acid, p-toluenesulfonic acid and the like, and the like can be mentioned. The Lewis acid can also be used in combination with a thiol or a sulfide.

As the base, for example, alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like can be mentioned. The amount of the acid or base to be used is about 0.5 to about 10 mol, preferably about 0.5 to about 6 mol, per 1 mol of compound (Ia).

The hydrolysis reaction is carried out without a solvent or in a solvent inert to the reaction. While the solvent is not particularly limited as long as the reaction proceeds, for example, solvents including alcohols such as methanol, ethanol, 1-propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethyl sulfoxide and the like; water and the like, a mixed solvent thereof and the like are preferable.

The reaction time is generally about 10 min to about 60 hr, preferably about 10 min to about 12 hr. The reaction temperature is generally about −10° C. to about 200° C., preferably about 0° C. to about 120° C.

Compound (Ic) can be produced by esterification or amidation of compound (Ib) by a method known per se or a method analogous thereto.

For the esterification reaction, a method known per se or a method analogous thereto can be used and, for example, (1) a method comprising reacting compound (Ib) with a compound represented by the formula: $R^{3a'}$-L' ($R^{3a'}$ is an optionally substituted $C_{1-6}$ alkyl group) in the presence of a base; (2) a method comprising reacting compound (Ib) with a compound represented by the formula: $R^{3a}$—H in the presence of an acid catalyst, condensing the compounds using a condensing agent [for example, carbodiimides (N,N'-dicyclohexylcarbodiimide, 1-ethyl-3-(3-dimethylaminopropyl)carbodiimide hydrochloride), phosphoric acid derivative (e.g., diethyl cyanophosphate, diphenylphosphoryl azide, bis(2-oxo-3-oxazolidinyl)phosphinic chloride)], or subjecting the compounds to the Mitsunobu reaction using a reagent such as triphenylphosphine, diethyl azodicarboxylate and the like; (3) a method comprising reacting a reactive derivative (e.g., acid halide, activated ester, acid azide) of compound (Ib) with a compound represented by the formula: $R^{3a}$—H in the presence of a base; and the like can be used.

For amidation reaction, a method known per se or a method analogous thereto can be used. For example, a method comprising reacting compound (Ib) with a compound represented by the formula: $R^{3b'}$—H ($R^{3b'}$ is an optionally substituted amino group) using a condensing agent [for example, carbodiimides (N,N'-dicyclohexylcarbodiimide, 1-ethyl-3-(3-dimethylaminopropyl)carbodiimide hydrochloride etc.), phosphoric acid derivative (e.g., diethyl cyanophosphate, diphenylphosphoryl azide, bis(2-oxo-3-oxazolidinyl)phosphinic chloride etc.) and the like], a method comprising reacting a reactive derivative (e.g., acid halide, acid anhydride, activated ester, acid imidazolide, acid azide) of compound (Ib) with a compound represented by the formula: $R^{3b'}$—H ($R^{3b'}$ is as defined above), and the like can be used.

Compound (Ia) can also be produced, for example, according to the method shown in the following Scheme 2 or a method analogous thereto.

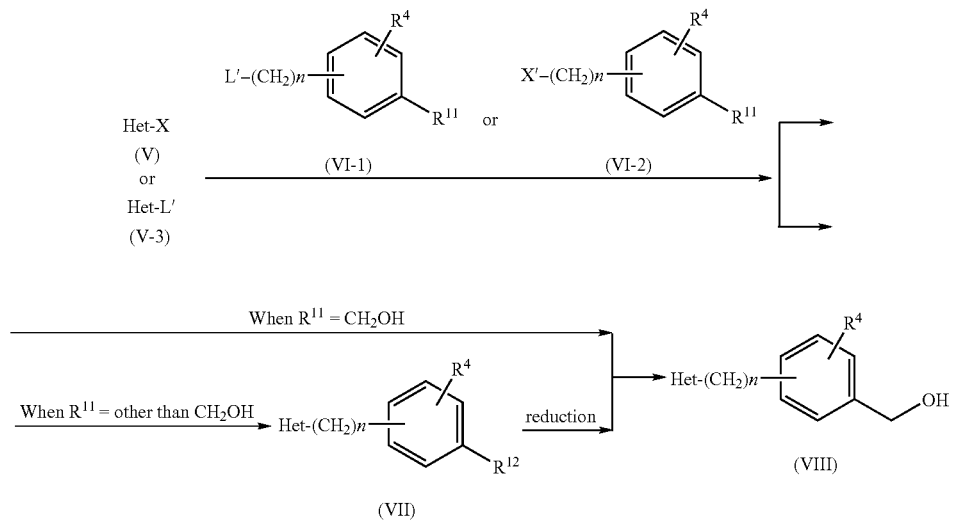

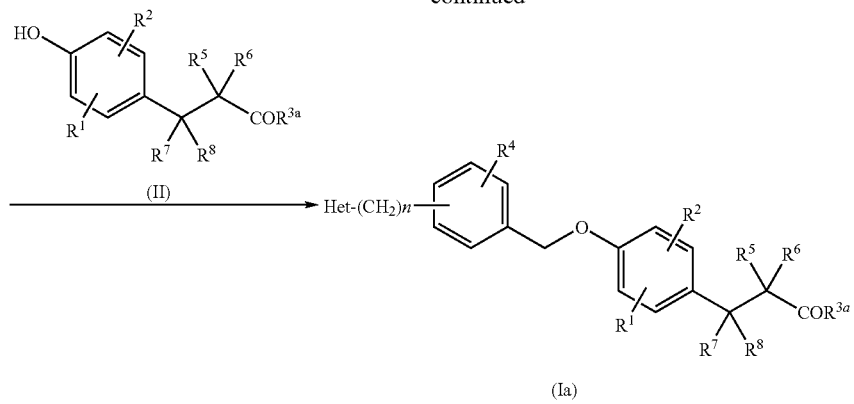

wherein X' is a metal, $R^{11}$ is an optionally substituted $C_{1-4}$ alkoxy-carbonyl group, a formyl group or a hydroxymethyl group (when, in the formula (VI-2), $R^{11}$ is a hydroxymethyl group, then X' is an optionally complexed boron), $R^{12}$ is an optionally substituted $C_{1-4}$ alkoxy-carbonyl group or a formyl group, and other symbols are as defined above.

As the metal represented by X', those exemplified as the aforementioned X can be used.

Compounds represented by the formulas (V-3), (VI-1) and (VI-2) (to be abbreviated as compound (V-3), compound (VI-1) and compound (VI-2), respectively) are easily commercially available, or can also be produced according to a method known per se or a method analogous thereto.

As the "optionally substituted $C_{1-4}$ alkoxy-carbonyl group" for $R^{11}$ or $R^{12}$, for example, a $C_{1-4}$ alkoxy-carbonyl group optionally having 1 to 3 substituents selected from a phenyl group, a halogen atom, a $C_{1-6}$ alkoxy group and the like (e.g., methoxycarbonyl, ethoxycarbonyl, benzyloxycarbonyl, 2-(ethoxy)ethoxycarbonyl) and the like can be mentioned.

(i) When $R^{11}$ of compound (VI-1) or compound (VI-2) is a hydroxymethyl group, a compound represented by the formula (VIII) (to be abbreviated as compound (VIII)) can be produced by reacting compound (V) with compound (VI-1) in the same manner as in the reaction of compound (IV) with compound (V) in Scheme 1, or can be produced by reacting compound (V-3) with compound (VI-2).

(ii) When $R^{11}$ of compound (VI-1) or compound (VI-2) is an optionally substituted $C_{1-4}$ alkoxy-carbonyl group or a formyl group (i.e., $R^{11}$ is $R^{12}$), compound (VIII) can also be produced by obtaining a compound represented by the formula (VII) (to be abbreviated as compound (VII)) in the same manner as in the above-mentioned (i) and subjecting this compound to a reduction reaction.

The reduction reaction is carried out using a reducing agent according to a conventional method. As the reducing agent, for example, metal hydrides such as aluminum hydride, diisobutylaluminum hydride, tributyltin hydride and the like; metal hydrogen complex compounds such as lithium aluminum hydride, sodium borohydride and the like; borane complexes such as borane tetrahydrofuran complex, borane dimethyl sulfide complex and the like; alkylboranes such as thexylborane, disiamylborane and the like; diborane; metals such as zinc, aluminum, tin, iron and the like; alkali metal (e.g., sodium, lithium etc.)/liquid ammonia (Birch reduction) and the like can be mentioned. The amount of the reducing agent to be used is appropriately determined according to the kind of the reducing agent. For example, the amount of each of the metal hydride or metal hydrogen complex compound to be used is about 0.25 to about 10 mol, preferably about 0.5 to about 5 mol, per 1 mol of compound (VII), the amount of each of the borane complex, alkylboranes or diborane to be used is about 1 to about 10 mol, preferably about 1 to about 5 mol, per 1 mol of compound (VII), and the amount of the metals (including alkali metal to be used for the Birch reduction) to be used is about 1 to about 20 mol, preferably about 1 to about 5 mol, per 1 mol of compound (VII).

The reduction reaction is advantageously carried out using a solvent inert to the reaction. While the solvent is not particularly limited as long as the reaction proceeds, for example, solvents including alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid and the like, and the like, a mixed solvent thereof and the like are preferable.

While the reaction time varies depending on the kind and amount of the reducing agent to be used, it is generally about 1 hr to about 100 hr, preferably about 1 hr to about 50 hr. The reaction temperature is generally about −20° C. to about 120° C., preferably about 0° C. to about 80° C.

Compound (Ia) can be produced by reacting compound (II) with compound (VIII) in the same manner as in the Mitsunobu reaction of compound (II) with compound (III) in Scheme 1.

Compounds represented by the formulas (If) and (Ig) (to be abbreviated as compound (If) and compound (Ig), respectively), which are compounds (I) wherein Het is $R^{13}$—Het' ($R^{13}$ is a substituent and Het' is a heterocyclic group for Het which contains, as a ring-constituting atom, at least one nitrogen atom bonded to $R^{13}$ (PG and H in the below-mentioned compound (Id) and compound (Ie), respectively)) can be produced, for example, according to the method shown in the following Scheme 3 or a method analogous thereto.

As the substituent for $R^{13}$, those exemplified as the substituents of Het can be mentioned. Of such substituents, an optionally substituted $C_{1-6}$ alkyl group (preferably, a $C_{1-6}$ alkyl group optionally substituted by 1 to 3 substituents selected from a halogen atom; a cyano group; a heterocyclic group (preferably, pyridyl); an optionally halogenated $C_{1-6}$ alkoxy group; a $C_{6-14}$ aryloxy group optionally substituted by optionally halogenated $C_{1-6}$ alkyl group(s); a $C_{6-14}$ aryl group optionally substituted by 1 to 3 halogen atoms; and a $C_{6-14}$ arylsulfonyl group); an optionally esterified carboxyl group (preferably, a $C_{1-6}$ alkoxy-carbonyl group) and the like are preferable.

of compound (Id) according to a deprotection reaction known per se or a method analogous thereto.

Compound (If) can be produced by reacting compound (Ie) with compound (IX) in the same manner as in the reaction of compound (II) with compound (III) wherein L is a leaving group in Scheme 1.

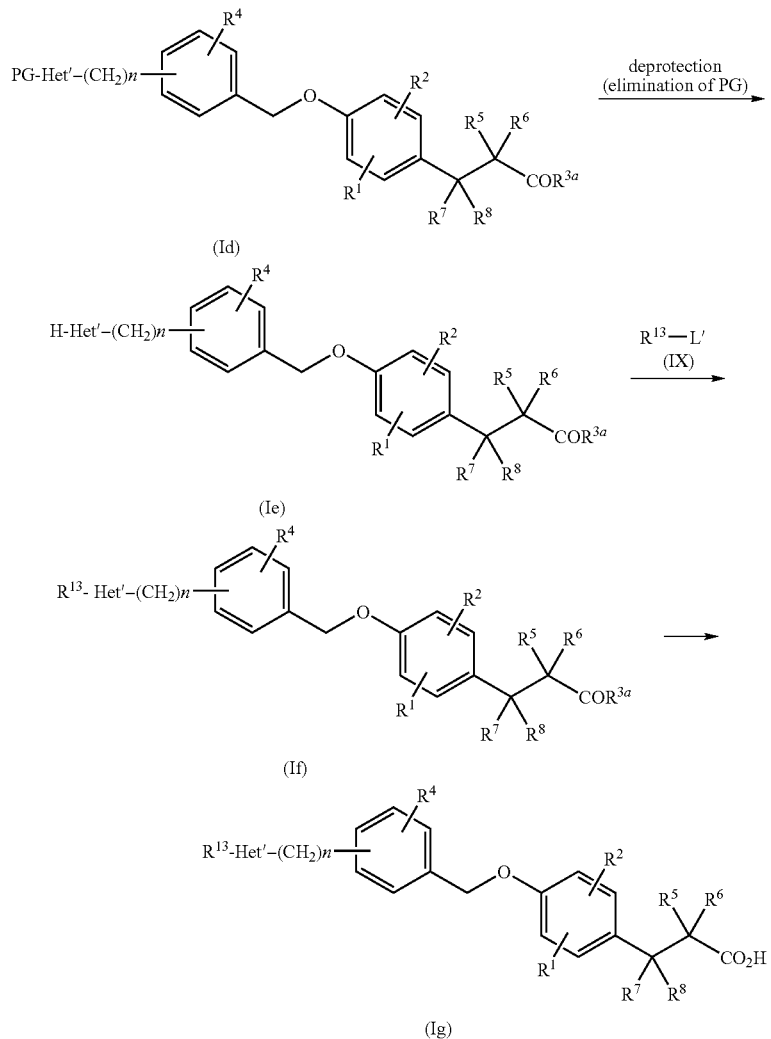

wherein PG is an amino-protecting group, and other symbols are as defined above.

As the amino-protecting group for PG, those mentioned below can be used.

A compound represented by the formula (IX) (to be abbreviated as compound (IX)) can be easily obtained as a commercially available product, or can also be produced according to a method known per se or a method analogous thereto.

A compound represented by the formula (Id) (to be abbreviated as compound (Id)) can be produced according to the methods described in the aforementioned Schemes 1 and 2, or a method analogous thereto.

A compound represented by the formula (Ie) (to be abbreviated as compound (Ie)) can be produced by eliminating PG Compound (Ig) can be produced from compound (If) by a method similar to the hydrolysis reaction of compound (Ia) in Scheme 1.

Of compounds (I), compounds represented by the formulas (Ih) and (Ii) (to be abbreviated as compound (Ih) and compound (Ii), respectively) wherein the heterocyclic group for Het contains, as a ring-constituting atom, at least one nitrogen atom bonded to —$(CH_2)n$-, and n is 1 can be produced, for example, according to the method shown in the following Scheme 4 or a method analogous thereto.

Scheme 4

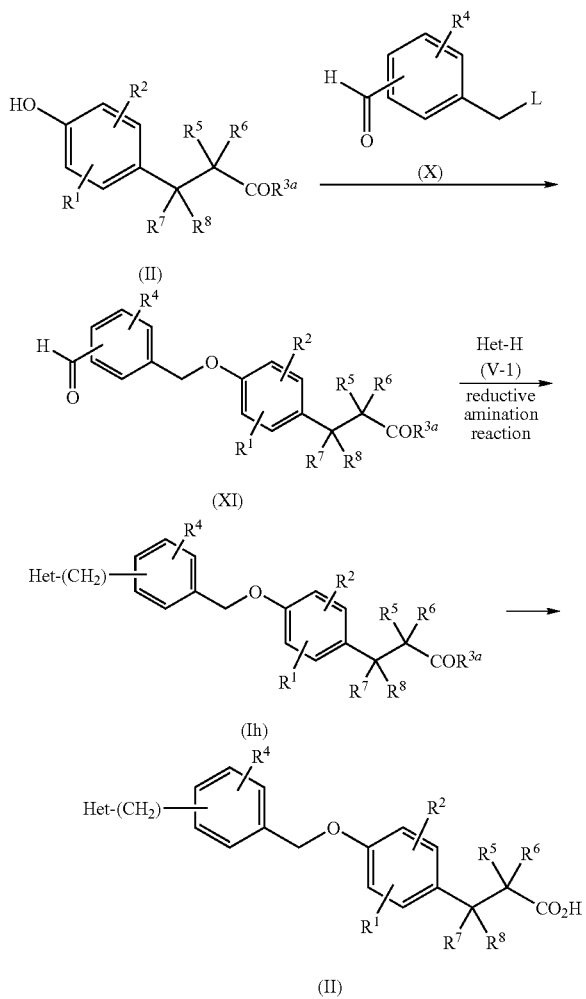

wherein symbols are as defined above.

A compound represented by the formula (X) (to be abbreviated as compound (X)) can be easily obtained as a commercially available product, or can also be produced according to a method known per se or a method analogous thereto.

A compound represented by the formula (XI) (to be abbreviated as compound (XI)) can be produced by reacting compound (II) with compound (X) in the same manner as in the reaction of compound (II) with compound (III) in Scheme 1.

Compound (Ih) can be produced by subjecting compound (XI) and compound (V-1) to a reductive amination reaction (e.g., described in *JIKKEN KAGAKU KOUZA*, 4$^{th}$ Edition., vol. 20, pp. 282-284 and 366-368 (Chemical Society of Japan); *J. Am. Chem. Soc.*, vol. 93, pp. 2897-2904, 1971; *Synthesis*, pp. 135, 1975 and the like).

The reductive amination reaction is carried out according to a conventional method and generally using a reducing agent. As the reducing agent, for example, metal hydrides such as aluminum hydride, diisobutylaluminum hydride, tributyltin hydride and the like; metal hydrogen complex compounds such as sodium cyanoborohydride, sodium triacetoxyborohydride, sodium borohydride, lithium aluminum hydride and the like; borane complexes such as borane tetrahydrofuran complex, borane dimethyl sulfide complex and the like; alkylboranes such as thexylborane, disiamylborane and the like; diborane; metals such as zinc, iron and the like, and the like can be mentioned. The amount of the reducing agent to be used is appropriately determined according to the kind of the reducing agent. For example, the amount of each of the metal hydride, metal hydrogen complex compound, borane complex, alkylboranes and diborane to be used is about 0.25 to about 10 mol, preferably about 0.5 to about 5 mol, per 1 mol of compound (XI), and the amount of the metals to be used is about 1 to about 20 mol, preferably about 1 to about 5 mol, per 1 mol of compound (XI).

The reductive amination reaction can also be carried out by a hydrogenation reaction. In this case, for example, catalysts such as palladium carbon, palladium black, platinum dioxide, Raney-nickel, Raney-cobalt and the like are used. The amount of the catalyst to be used is about 5 to about 1000 wt %, preferably about 10 to about 300 wt %, relative to compound (XI). The hydrogenation reaction can also be carried out using various hydrogen sources instead of gaseous hydrogen. As such hydrogen sources, for example, formic acid, ammonium formate, triethylammonium formate, sodium phosphinate, hydrazine and the like can be mentioned. The amount of the hydrogen source to be used is about 1 to about 10 mol, preferably about 1 to about 5 mol, per 1 mol of compound (XI).

This reaction is advantageously carried out using a solvent inert to the reaction. While the solvent is not particularly limited as long as the reaction proceeds, for example, solvents including halogenated hydrocarbons such as 1,2-dichloroethane and the like; alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid and the like, and the like, a mixed solvent thereof and the like are preferable.

This reaction can also be carried out in the presence of an acid for the purpose of promoting the reaction. As the acid, for example, mineral acids such as hydrochloric acid, sulfuric acid and the like; organic acids such as formic acid, acetic acid, propanoic acid, trifluoroacetic acid, methanesulfonic acid and the like, and the like can be mentioned. The amount of the acid to be used is about 1 mol to solvent amount, preferably about 1 to about 5 mol, per 1 mol of compound (XI).

While the reaction time varies depending on the reagent and solvent to be used, it is generally about 10 min to about 100 hr, preferably about 30 min to about 50 hr.

The reaction temperature is generally about -20° C. to about 100° C., preferably about 0° C. to about 80° C.

The amount of the compound (V-1) to be used is about 0.5 to about 5 mol, preferably about 1 to about 2 mol, per 1 mol of compound (XI).

Compound (Ii) can be produced from compound (Ih) in the same manner as in the hydrolysis reaction of compound (Ia) in Scheme 1.

Of compounds (VIII) shown in Scheme 2, a compound represented by the formula (XIV) (to be abbreviated as compound (XIV)) wherein the heterocyclic group for Het contains, as a ring-constituting atom, at least one nitrogen atom bonded to —(CH$_2$)n- and n is 1 can also be produced, for example, according to the method shown in the following Scheme 5 or a method analogous thereto.

Scheme 5

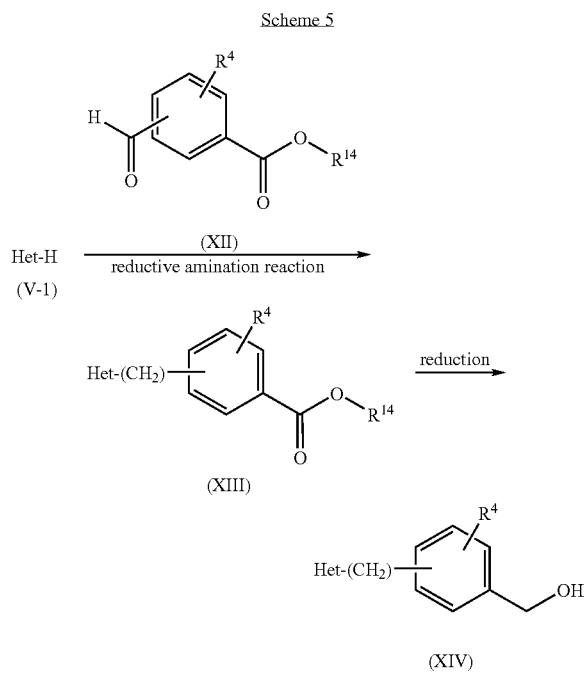

wherein $R^{14}$ is an optionally substituted $C_{1-4}$ alkyl group, and other symbols are as defined above.

A compound represented by the formula (XII) (to be abbreviated as compound (XII)) can be easily obtained as a commercially available product, or can also be produced according to a method known per se or a method analogous thereto.

As the "optionally substituted $C_{1-4}$ alkyl group" for $R^{14}$, for example, a $C_{1-4}$ alkyl group optionally having 1 to 3 substituents selected from a phenyl group, a halogen atom and the like (e.g., methyl, ethyl, benzyl) and the like can be mentioned.

A compound represented by the formula (XIII) (to be abbreviated as compound (XIII)) can be produced by reacting compound (V-1) with compound (XII) in the same manner as in the reaction of compound (XI) with compound (V-1) in Scheme 4.

Compound (XIV) can be produced by the reduction of compound (XIII) in the same manner as in the reduction reaction of compound (VII) in Scheme 2.

In addition, in each of the aforementioned reactions, when the starting compound has an amino group, a carboxyl group, a hydroxy group or a mercapto group as a substituent, a protecting group generally used in peptide chemistry and the like may be introduced into these groups. By removing the protecting group as necessary after the reaction, the objective compound can be obtained.

As the amino-protecting group, for example, formyl group; $C_{1-6}$ alkyl-carbonyl group (e.g., acetyl, ethylcarbonyl), phenylcarbonyl group, $C_{1-6}$ alkoxy-carbonyl group (e.g., methoxycarbonyl, ethoxycarbonyl, tert-butoxycarbonyl (Boc)), allyloxycarbonyl group (Alloc), phenyloxycarbonyl group, fluorenylmethyloxycarbonyl group (Fmoc), $C_{7-10}$ aralkyl-carbonyl group (e.g., benzylcarbonyl), $C_{7-10}$ aralkyloxy-carbonyl group (e.g., benzyloxycarbonyl (Z)), $C_{7-20}$ aralkyl group (e.g., benzyl, trityl), phthaloyl group, dithiasuccinoyl group and N,N-dimethylaminomethylene group, each optionally having substituent(s), and the like can be mentioned. As these substituents, phenyl group, halogen atom, $C_{1-6}$ alkyl-carbonyl group (e.g., acetyl, ethylcarbonyl, butylcarbonyl and the like), optionally halogenated $C_{1-6}$ alkoxy group, nitro group and the like are used. The number of the substituent(s) is about 1 to 3.

As the carboxyl-protecting group, for example, $C_{1-6}$ alkyl group, allyl group, benzyl group, phenyl group, trityl group and trialkylsilyl group, each optionally having substituent(s), and the like can be mentioned. As these substituents, halogen atom, formyl group, $C_{1-6}$ alkyl-carbonyl group (e.g., acetyl, ethylcarbonyl, butylcarbonyl), optionally halogenated $C_{1-6}$ alkoxy group, nitro group and the like are used. The number of the substituent(s) is about 1 to 3.

As the hydroxy-protecting group, for example, $C_{1-6}$ alkyl group, $C_{7-20}$ aralkyl group (e.g., benzyl, trityl), formyl group, $C_{1-6}$ alkyl-carbonyl group (e.g., acetyl, ethylcarbonyl), benzoyl group, $C_{7-10}$ aralkyl-carbonyl group (e.g., benzylcarbonyl), 2-tetrahydropyranyl group, tetrahydrofuranyl group and trialkylsilyl group (e.g., trimethylsilyl, tert-buthyldimethylsilyl, diisopropylethylsilyl), each optionally having substituent(s), and the like can be mentioned. As these substituents, halogen atom, $C_{1-6}$ alkyl group, phenyl group, $C_{7-10}$ aralkyl group (e.g., benzyl), $C_{1-6}$ alkoxy group, nitro group and the like are used. The number of the substituent(s) is about 1 to 4.

As the mercapto-protecting group, for example, $C_{1-6}$ alkyl group and $C_{7-20}$ aralkyl group (e.g., benzyl, trityl), each optionally having substituent(s), and the like can be mentioned. As these substituents, halogen atom, $C_{1-6}$ alkyl group, phenyl group, $C_{7-10}$ aralkyl group (e.g., benzyl), $C_{1-6}$ alkoxy group, nitro group and the like are used. The number of the substituent(s) is about 1 to 4.

For elimination of the protecting group, a method known per se or a method analogous thereto is used. For example, treatments with acid, base, reduction, ultraviolet rays, hydrazine, phenylhydrazine, sodium N-methyldithiocarbamate, tetrabutylammonium fluoride, palladium acetate and the like can be used.

Compound (I) obtained in this manner, other reaction intermediates and starting compounds thereof can be isolated and purified from the reaction mixture by a method known per se, such as extraction, concentration, neutralization, filtration, distillation, recrystallization, column chromatography, thin layer chromatography, preparative high performance liquid chromatography (preparative HPLC), medium pressure preparative liquid chromatography (medium pressure preparative LC) and the like.

The salt of compound (I) can be produced according to a method known per se. For example, when compound (I) is a basic compound, the salt can be produced by adding an inorganic acid or an organic acid, or when compound (I) is an acidic compound, it can be produced by adding an organic base or an inorganic base.

When compound (I) has optical isomers, these respective optical isomers and mixtures thereof are naturally encompassed in the scope of the present invention, and where desired, these isomers can be also subjected to optical resolution or individually produced according to a method known per se.

When compound (I) is present as a configurational isomer, diastereomer, conformer or the like, each can be isolated by the above separation and purification methods on demand. In addition, when compound (I) is in the form of racemates, they can be separated into S- and R-forms by any conventional optical resolution.

When compound (I) includes stereoisomers, both the isomers alone and mixtures of each isomers are included in the scope of the present invention.

In addition, compound (I) may be a hydrate or non-hydrate.

Compound (I) may be labeled with an isotope (e.g., $^3$H, $^{14}$C, $^{35}$S) or the like.

Since compound (I) and a prodrug thereof (hereinafter, sometimes to be also abbreviated to as a compound of the present invention) have a GPR40 receptor function modulating action (GPR40 receptor agonist activity and GPR40 receptor antagonist activity), particularly a GPR40 receptor agonist activity, show low toxicity and fewer side effects (e.g., acute toxicity, chronic toxicity, genetic toxicity, reproductive toxicity, cardiotoxicity, drug interaction, carcinogenicity), they are useful as safe GPR40 receptor function modulators, preferably GPR40 agonists.

A pharmaceutical agent containing the compound of the present invention shows a superior GPR40 receptor function modulating action in mammals (e.g., mouse, rat, hamster, rabbit, cat, dog, bovine, sheep, monkey, human etc.), and are useful as modulators of physiological function in which GPR40 receptor is involved or agents for the prophylaxis or treatment of disease state or disease in which GPR40 receptor is involved.

To be specific, a pharmaceutical agent containing the compound of the present invention is useful as insulin secretion modulators (preferably insulin secretagogues), hypoglycemic drugs and pancreatic p cell protectors.

Moreover, a pharmaceutical agent containing the compound of the present invention is useful as agents for the prophylaxis or treatment of diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder, depression, depression and mania, schizophrenia, attention deficit hyperactivity disorder, visual disorder, appestat disorder (e.g., hyperorexia), obesity, hypoglycemia, hypertension, edema, insulin resistance, unstable diabetes, fatty atrophy, insulin allergy, insulinoma, lipotoxicity, pancreatic fatigue, hyperinsulinemia, cancers (e.g., breast cancer), metabolic syndrome, immune diseases (e.g., immunodeficiency), inflammatory disease (e.g., enteritis, arthritis, allergy), multiple sclerosis, acute kidney failure and the like; particularly, diseases such as diabetes, impaired glucose tolerance, ketosis, acidosis, diabetic neuropathy, diabetic nephropathy, diabetic retinopathy, macular edema, hyperlipidemia, genital disorder, skin disease, arthropathy, osteopenia, arteriosclerosis, thrombotic disease, dyspepsia, memory and learning disorder and the like. Here, diabetes includes type I diabetes, type II diabetes and gestational diabetes. In addition, hyperlipidemia includes hypertriglyceridemia, hypercholesterolemia, hypo-high-density-lipoproteinemia, postprandial hyperlipidemia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). On the other hand, according to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can be also used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

Since the compound of the present invention has a superior insulin secretion promoting action, it can be preferably used as an agent for treating insulin secretion deficient diabetes in patients with insulin secretion deficient diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea skeleton, such as glinide compounds (e.g., repaglinide, senaglinide, nateglinide, mitiglinide, a calcium salt hydrate thereof etc.), and the like, can be mentioned.

A pharmaceutical agent containing the compound of the present invention shows low toxicity, and can be safely administered orally or parenterally (e.g., topical, rectal, intravenous administration etc.) in the form of the compound of the present invention as it is or after admixing with a pharmacologically acceptable carrier to give a pharmaceutical preparation according to a method known per se employed for general production methods for pharmaceutical preparations.

The dosage form of the aforementioned pharmaceutical preparation is, for example, an oral agent such as tablets (inclusive of sublingual tablets and orally disintegrable tablets), capsules (inclusive of soft capsules and micro capsules), granules, powders, troches, syrups, emulsions, suspensions and the like; or a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like.

These agents may be controlled-release preparations such as rapid-release preparations and sustained-release preparations (e.g., sustained-release microcapsules).

The content of the compound of the present invention in a pharmaceutical preparation is about 0.01 to about 100% by weight relative to the whole preparation. While the dose of the compound of the present invention varies depending on the administration subject, administration route, diseases, condition and the like, for example, the compound of the present invention can be orally administered to an adult patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions a day.

As the above-mentioned pharmacologically acceptable carrier, various organic or inorganic carrier substances conventionally used as a preparation material can be mentioned. For example, excipient, lubricant, binder and disintegrant for solid preparations, solvent, dissolution aids, suspending agent, isotonicity agent, buffer and soothing agent for liquid preparations and the like can be mentioned. Where necessary, additives such as preservative, antioxidant, coloring agent, sweetening agent, adsorbing agent, wetting agent and the like can also be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the dissolution aids, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropanoate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphate, acetate, carbonate, citrate and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfite, ascorbic acid, α-tocopherol and the like can be mentioned.

As the coloring agent, for example, water-soluble edible tar pigments (e.g., food colors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., β-carotene, chlorophil, red iron oxide) and the like can be mentioned.

As the sweetening agent, for example, saccharin sodium, dipotassium glycyrrhizinate, aspartame, stevia and the like can be mentioned.

The compound of the present invention can be used in combination with drugs such as therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, therapeutic agents for pollakiuria or urinary incontinence, therapeutic agents for dysuria and the like (hereinafter, sometimes to be abbreviated to as drug X).

As the above-mentioned therapeutic agents for diabetes, insulin preparations (e.g., animal insulin preparations extracted from pancreas of bovine or swine; human insulin preparations genetically synthesized using Escherichia coli or yeast; zinc insulin; protamine zinc insulin; fragment or derivative of insulin (e.g., INS-1 etc.), oral insulin preparation and the like), insulin sensitizers (e.g., pioglitazone or a salt thereof (preferably hydrochloride), rosiglitazone or a salt thereof (preferably maleate), Reglixane (JTT-501), Netoglitazone (MCC-555), GI-262570, FK-614, Rivoglitazone (CS-011), Muraglitazar (BMS-298585), compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), BM-13-1258, LM-4156, MBX-102, LY-519818, MX-6054, LY-510929, Balaglitazone (N,N-2344), T-131 or a salt thereof, THR-0921), α-glucosidase inhibitors (e.g., voglibose, acarbose, miglitol, emiglitate etc.), biguanides (e.g., phenformin, metformin, buformin or salts thereof (e.g., hydrochloride, fumarate, succinate) etc.), insulin secretagogues [sulfonylureas (e.g., tolbutamide, glibenclamide, gliclazide, chlorpropamide, tolazamide, acetohexamide, glyclopyramide, glimepiride etc.), repaglinide, senaglinide, mitiglinide or calcium salt hydrate thereof, nateglinide etc.], GLP-1 receptor agonists [e.g., GLP-1, GLP-1MR agent, N,N-2211, AC-2993 (exendin-4), BIM-51077, Aib(8,35) hGLP-1 (7,37)$NH_2$, CJC-1131 etc.], dipeptidyl peptidase IV inhibitors (e.g., NVP-DPP-278, PT-100, P32/98, P93/01, NVP-DPP-728, LAF237, TS-021 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., sodium vanadate etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.), 11β-hydroxysteroid dehydrogenase inhibitors (e.g., BVT-3498 etc.), adiponectin or agonists thereof, IKK inhibitors (e.g., AS-2868 etc.), leptin resistance improving drugs, somatostatin receptor agonists (compounds described in WO01/25228, WO03/42204, WO98/45285 and WO99/22735 etc.), glucokinase activators (e.g., Ro-28-1675) and the like can be mentioned.

Examples of the therapeutic agents for diabetic complications include aldose reductase inhibitors (e.g., Tolrestat, Epalrestat, Zenarestat, Zopolrestat, Fidarestat (SNK-860), AS-3201, Minalrestat (ARI-509), CT-112 etc.), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole etc.) and the like), protein kinase C (PKC) inhibitors (e.g., ruboxistaurin mesylate; LY-333531 etc.), AGE inhibitors (e.g., ALT-945, pimagedine, pyratoxanthine, N-phenacylthiazolium bromide (ALT-766), EXO-226, ALT-711, Pyridorin, Pyridoxamine etc.), active oxygen scavengers (e.g., thioctic acid etc.), cerebral vasodilators (e.g., tiapuride etc.), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin or salts thereof (e.g., sodium salt, calcium salt etc.) etc.), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate etc.), antioxidants (e.g., lipoic acid, probucol) and the like.

Examples of the antihypertensive agents include angiotensin converting enzyme inhibitors (e.g., captopril, enalapril, delapril etc.), angiotensin II receptor antagonists (e.g., losartan, candesartan cilexetil, eprosartan, valsartan, telmisartan, irbesartan, olmesartan medoxomil, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonists (e.g., manidipine, nifedipine, amlodipine, efonidipine, nicardipine etc.), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834 etc.); neuropeptide Y antagonists (e.g., CP-422935 etc.); cannabinoid receptor antagonists (e.g., SR-141716, SR-147778 etc.); ghrelin antagonists and the like), 11β-hydroxysteroid dehydrogenase inhibitors (e.g., BVT-3498 etc.)), pancreatic lipase inhibitors (e.g., orlistat, ATL-962 etc.), β3 agonists (e.g., CL-316243, SR-58611-A, UL-TG-307, AJ-9677, AZ40140 etc.), peptide anorexiants (e.g., leptin, CNTF (Ciliary Neurotropic Factor) etc.), cholecystokinin agonists (e.g., lintitript, FPL-15849 etc.), feeding deterrents (e.g., P-57 etc.) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlortalidone, mefruside, indapamide etc.), azosemide, isosorbide, etacrynic acid, piretanide, bumetamide, furosemide and the like.

Examples of the chemotherapeutic agents include alkylating agents (e.g., cyclophosphamide, ifosfamide etc.), metabolic antagonists (e.g., methotrexate, 5-fluorouracil and a derivative thereof etc.), antitumor antibiotics (e.g., mitomycin, adriamycin etc.), plant-derived antitumor agents (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to interleukins such as IL-1, IL-2, IL-12 and the like. Examples of the anti-inflammatory agents include non-steroidal antiinflammatory agents such as aspirin, acetaminophen, indomethacin and the like, and the like.

Examples of the antithrombotic agents include heparin (e.g., heparin sodium, heparin calcium, dalteparin sodium etc.), warfarin (e.g., warfarin potassium etc.), anti-thrombin drugs (e.g., aragatroban etc.), thrombolytic agents (e.g., urokinase, tisokinase, alteplase, nateplase, monteplase, pamiteplase etc.), platelet aggregation inhibitors (e.g., ticlopidine hydrochloride, cilostazol, ethyl icosapentate, beraprost sodium, sarpogrelate hydrochloride etc.) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-ameliorating action established in animal models and clinical situations, such as cyclooxygenase inhibitors (e.g., indomethacin etc.), progesterone derivatives (e.g., megestrol acetate), glucosteroids (e.g., dexamethasone etc.), metoclopramide agents, tetrahydrocannabinol agents, fat metabolism improving agents (e.g., eicosapentanoic acid etc.), growth hormones, IGF-1, or antibodies to a cachexia-inducing factor such as TNF-α, LIF, IL-6 and oncostatin M, can be used in combination with the compound of the present invention.

Furthermore, glycosylation inhibitors (e.g., ALT-711 etc.), nerve regeneration promoting drugs (e.g., Y-128, VX853, prosaptide, etc.), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agents), α2 receptor agonists (e.g., clonidine), local analgesics (e.g., capsaicin), antianxiety drugs (e.g., benzothiazepine), phosphodiesterase inhibitors (e.g., sildenafil), dopamine receptor agonists (e.g., apomorphine) and the like can be also used in combination with the compound of the present invention.

The above-mentioned drug X may be used in a mixture of two or more kinds thereof at an appropriate ratio.

By combining the compound of the present invention with drug X, superior effects such as (1) decreased dose of the compound of the present invention and/or drug X as compared to single administration of the compound of the present invention or drug X,
(2) possible setting of a long treatment period by selecting drug X having different action and mechanism from those of the compound of the present invention,
(3) possible designing of a sustained treatment effect by selecting drug X having different action and mechanism from those of the compound of the present invention,
(4) a synergistic effect afforded by a combined use of the compound of the present invention and drug X, and the like can be achieved.

When the compound of the present invention and drug X are used in combination, the administration time of the compound of the present invention and the drug X is not restricted, and the compound of the present invention and the drug X can be administered to an administration subject simultaneously, or may be administered at staggered times. The dosage of the drug may be determined according to the dose clinically used, and can be appropriately selected depending on an administration subject, administration route, disease, combination and the like.

The administration mode of the compound of the present invention and the drug X is not particularly restricted, and it is sufficient that the compound of the present invention and the drug X are combined in administration. As such administration mode, the following methods can be mentioned: (1) The compound of the present invention and the drug X are simultaneously formulated to give a single preparation which is administered. (2) The compound of the present invention and the drug X are separately formulated to give two kinds of preparations which are administered simultaneously by the same administration route. (3) The compound of the present invention and the drug X are separately formulated to give two kinds of preparations which are administered by the same administration route at staggered times. (4) The compound of the present invention and the drug X are separately formulated to give two kinds of preparations which are administered simultaneously by the different administration routes. (5) The compound of the present invention and the drug X are separately formulated to give two kinds of preparations which are administered by the different administration routes at staggered times (for example, the compound of the present invention and the drug X are administered in this order, or in the reverse order), and the like.

EXAMPLES

The present invention is further explained in detail by referring to the following Reference Examples, Examples, Formulation Examples and Experimental Example, which are mere working examples not to be construed as limitative and may be changed without departing from the scope of the present invention.

The term "room temperature" in the following Reference Examples and Examples indicates the range of generally from about 10° C. to about 35° C. As for "%", the yield is in mol/mol %, the solvent used for column chromatography is in % by volume and other "%" is in % by weight. OH proton, NH proton etc. that could not be confirmed due to broad peak by proton NMR spectrum are not included in the data.

The other symbols used herein mean the following:

s: singlet
d: doublet
t: triplet
q: quartet
m: multiplet
br: broad
J: coupling constant
Hz: Hertz
$CDCl_3$: deuterated chloroform
DMSO-$d_6$: $d_6$-dimethyl sulfoxide
$^1$H NMR: proton nuclear magnetic resonance
TFA: trifluoroacetic acid In the following Reference Examples and Examples, mass spectrum (MS) and nuclear magnetic resonance spectrum (NMR) were measured under the following conditions.

MS measurement tools: ZMD manufactured by Waters Corporation, ZQ2000 manufactured by Waters Corporation or platform II manufactured by Micromass Ltd.

ionization method: Electron Spray Ionization (ESI) or Atmospheric Pressure Chemical Ionization (APCI). Unless specifically indicated, ESI was used.

NMR measurement tools: Varian Gemini 200 (200 MHz) manufactured by Varian, Varian Gemini 300 (300 MHz) manufactured by Varian, AVANCE 300 manufactured by Bruker BioSpin Corp.

In Reference Examples and Examples, purification by preparative HPLC was performed under the following conditions preparative HPLC tools: high through-put purification system manufactured by Gilson, Inc.

column: YMC Combiprep ODS-A S-5 μm, 20×50 mm
solvent:
  Solution A; 0.1% trifluoroacetic acid-containing water,
  Solution B; 0.1% trifluoroacetic acid-containing acetonitrile gradient cycle A: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10).

gradient cycle B: 0.00 min (Solution A/Solution B=95/5), 1.00 min (Solution A/Solution B=95/5), 5.20 min (Solution A/Solution B=5/95), 6.40 min (Solution A/Solution B=5/95), 6.50 min (Solution A/Solution B=95/5), 6.60 min (Solution A/Solution B=95/5).

flow rate: 25 ml/min,
detection method: UV 220 nm

In the present specification, the melting point (m.p.) refers to that measured using, for example, micromelting point measuring apparatus (Büchi, B-545) and the like.

In general, melting points vary depending on measurement apparatuses, measurement conditions and the like. The crystal in the present specification may show a different melting point from that described in the present specification, as long as it is within general error range.

Reference Example 1

3-(1,3,5-trimethyl-1H-pyrazol-4-yl)benzaldehyde

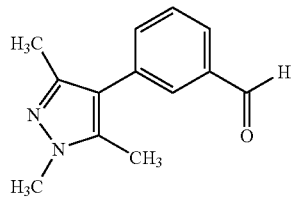

4-Bromo-1,3,5-trimethyl-1H-pyrazole (2.84 g, 15.0 mmol) and (3-formylphenyl)boronic acid (2.13 g, 15.0 mmol) were dissolved in a mixed solution of 1 M aqueous sodium carbonate solution (30 mL), ethanol (15 mL) and toluene (30 mL), and after argon substitution, tetrakis(triphenylphosphine)palladium(0) (0.867 g, 0.750 mmol) was added. The reaction mixture was stirred under an argon atmosphere at 80° C. for 24 hr. After cooling the reaction mixture, water and ethyl acetate were added, and the insoluble material was filtered off through celite. The organic layer of the filtrate washed with saturated brine, dried over anhydrous magnesium sulfate, and concentrated under reduced pressure. The residue was purified by silica gel column chromatography (5%-95% ethyl acetate/hexane) to give the title compound (2.05 g, yield 64%) as a brown oil. MS: m/z 215 (MH$^+$).

Reference Example 2

[3-(1,3,5-trimethyl-1H-pyrazol-4-yl)phenyl]methanol

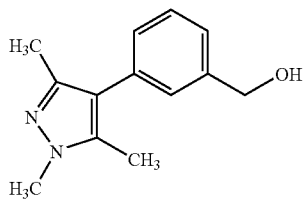

3-(1,3,5-Trimethyl-1H-pyrazol-4-yl)benzaldehyde (2.05 g, 9.57 mmol) was dissolved in a mixed solution of 1,2-dimethoxyethane (10 mL) and tetrahydrofuran (10 mL), sodium borohydride (0.265 g, 7.00 mmol) was added under ice-cooling, and the mixture was stirred under a nitrogen atmosphere at the same temperature for 3 hr. Dilute aqueous citric acid solution was added to the reaction mixture, and the mixture was extracted with ethyl acetate. The extract washed with saturated brine, dried over anhydrous sodium sulfate, and concentrated under reduced pressure. The residue was purified by silica gel column chromatography (50% ethyl acetate/hexane-ethyl acetate) to give the title compound (1.20 g, yield 58%) as a colorless oil. MS: m/z 217 (MH$^+$).

Reference Example 3

3-(2,4,5-trimethyl-3-thienyl)benzaldehyde

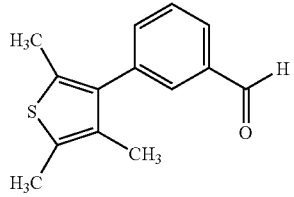

In the same manner as in Reference Example 1, the title compound was obtained as a yellow oil from 3-iodo-2,4,5-trimethylthiophene and (3-formylphenyl)boronic acid. yield 54%, MS: m/z 231 (MH$^+$).

Reference Example 4

[3-(2,4,5-trimethyl-3-thienyl)phenyl]methanol

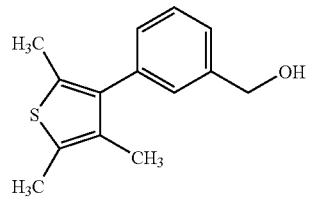

In the same manner as in Reference Example 2, the title compound was obtained as a colorless oil from 3-(2,4,5-trimethyl-3-thienyl)benzaldehyde. yield 83%, $^1$H NMR (CDCl$_3$) δ: 1.69 (1H, br s), 1.91 (3H, s), 2.25 (3H, s), 2.34 (3H, s), 4.74 (2H, s), 7.13 (1H, dt, J=7.4, 1.4 Hz), 7.20 (1H, s), 7.31-7.35 (1H, m), 7.41 (1H, t, J=7.4 Hz).

Reference Example 5

3-(1-benzothiophen-3-yl)benzaldehyde

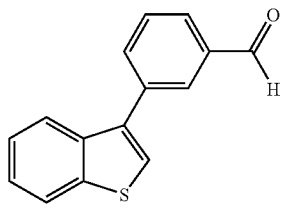

(3-Formylphenyl)boronic acid (1.7 g, 11.3 mmol), 3-bromo-1-benzothiophene (2.0 g, 9.39 mmol) and cesium carbonate (4.6 g, 14.1 mmol) were added to a mixed solution of ethanol (10 mL) and toluene (50 mL) and, after argon substitution, tetrakis(triphenylphosphine)palladium(0) (0.20 g, 0.17 mmol) was added. The reaction mixture was stirred under an argon atmosphere at 70° C. for 18 hr. After cooling the reaction mixture, the insoluble material was filtered off through celite, and the filtrate was concentrated under reduced pressure. The residue was subjected to silica gel column chromatography (ethyl acetate:hexane=1:10-1:5) to give the title compound (2.1 g, yield 94%) as a pale-yellow oil. MS: m/z 239 (MH⁺).

Reference Example 6

[3-(1-benzothiophen-3-yl)phenyl]methanol

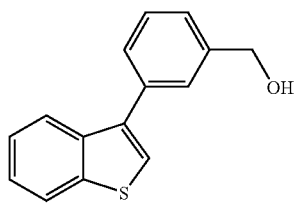

To a solution (30 mL) of 3-(1-benzothiophen-3-yl)benzaldehyde (2.1 g, 8.81 mmol) in anhydrous tetrahydrofuran was added lithium aluminum hydride (0.37 g, 9.75 mmol) under ice-cooling, and the mixture was stirred at room temperature for 2 hr. The reaction solution was ice-cooled, sodium sulfate decahydrate (3.0 g, 5.74 mmol) was added, and the mixture was stirred at room temperature for 1 hr. The precipitated insoluble material was filtered through celite, and the filtrate was concentrated under reduced pressure. The residue was subjected to silica gel column chromatography (ethyl acetate:hexane=1:5-1:3) to give the title compound (2.0 g, yield 95%) as a colorless oil. $^1$H NMR (CDCl$_3$) δ: 1.72 (1H, t, J=5.8 Hz), 4.80 (2H, d, J=5.8 Hz), 7.35-7.64 (7H, m), 7.88-7.98 (2H, m).

Reference Example 7

3-(1-benzothiophene-5-yl)benzaldehyde

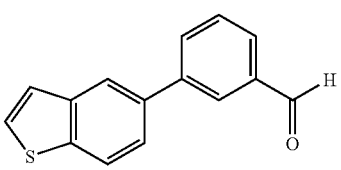

In the same manner as in Reference Example 5, the title compound was obtained as a pale-yellow oil from (3-formylphenyl)boronic acid and 5-bromo-1-benzothiophene. yield 70%, MS: m/z 239 (MH⁺).

Reference Example 8

[3-(1-benzothiophene-5-yl)phenyl]methanol

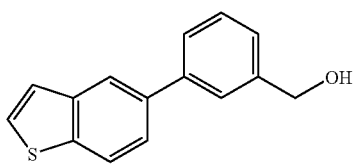

3-(1-Benzothiophene-5-yl)benzaldehyde (3.9 g, 16.4 mmol) was dissolved in a mixed solution of ethanol (80 mL) and tetrahydrofuran (20 mL), and the mixture was ice-cooled. Sodium borohydride (0.62 g, 16.4 mmol) was added to the solution. After stirring under ice-cooling for 3 hr, aqueous citric acid solution was added to the reaction solution, and the mixture was extracted with ethyl acetate. The extract was washed with aqueous sodium chloride solution, dried over anhydrous magnesium sulfate, and concentrated under reduced pressure. The obtained oil was crystallized from ethyl acetate-hexane to give the title compound (3.9 g, yield 99%) as colorless prism crystals.

$^1$H NMR (CDCl$_3$) δ: 1.73 (1H, t, J=6.0 Hz), 4.79 (2H, d, J=6.0 Hz), 7.35-7.63 (6H, m), 7.68 (1H, s), 7.94 (1H, d, J=8.1 Hz), 8.04 (1H, d, J=1.8 Hz).

Reference Example 9

2-(1-benzothiophen-3-yl)benzaldehyde

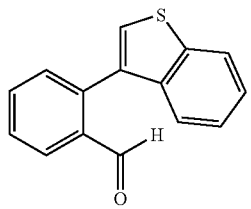

In the same manner as in Reference Example 5, the title compound was obtained as a pale-yellow oil from 3-bromo-1-benzothiophene and (2-formylphenyl)boronic acid. yield 100%, MS: m/z 239 (MH$^+$).

Reference Example 10

[2-(1-benzothiophen-3-yl)phenyl]methanol

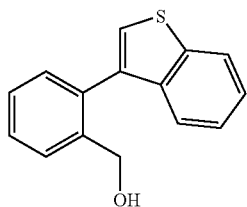

In the same manner as in Reference Example 8, the title compound was obtained as a colorless oil from 2-(1-benzothiophen-3-yl)benzaldehyde. yield 86%, $^1$H NMR (CDCl$_3$) δ: 1.52 (1H, t, J=6.0 Hz), 4.54 (2H, d, J=6.0 Hz), 7.28-7.97 (9H, m).

Reference Example 11 tert-butyl 5-bromo-1H-indole-1-carboxylate

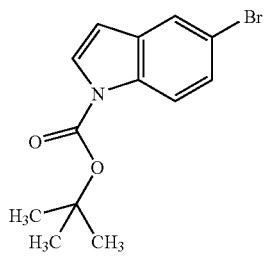

A solution of 5-bromo-indole (5.0 g, 25.5 mmol), di-tert-butyl dicarbonate (7.6 mL, 33.1 mmol) and 4-dimethylaminopyridine (0.15 g, 1.23 mmol) in acetonitrile (50 mL) was stirred at room temperature for 3 hr. An aqueous citric acid solution was added to the reaction solution, and the mixture was extracted with ethyl acetate. The extract was washed with aqueous sodium chloride solution, dried over anhydrous magnesium sulfate, and concentrated under reduced pressure to give the title compound (7.8 g, yield 100%) as a pale-yellow oil.

Reference Example 12 tert-butyl 5-(3-formylphenyl)-1H-indole-1-carboxylate

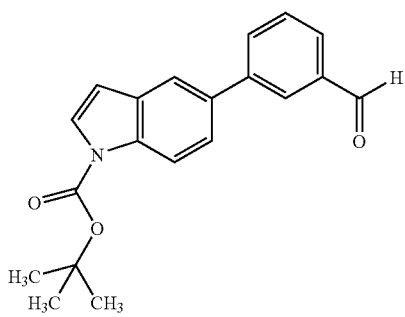

In the same manner as in Reference Example 5, the title compound was obtained as colorless prism crystals from (3-formylphenyl)boronic acid and tert-butyl 5-bromo-1H-indole-1-carboxylate. yield 61%, MS: m/z 322 (MH$^+$).

Reference Example 13 tert-butyl 5-(3-hydroxymethylphenyl)-1H-indole-1-carboxylate

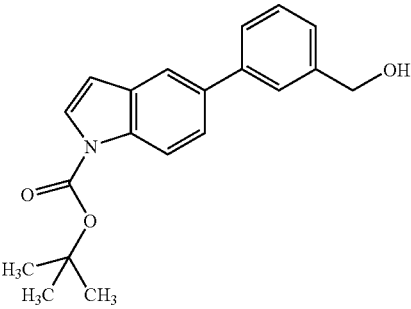

In the same manner as in Reference Example 8, the title compound was obtained as a colorless oil from tert-butyl 5-(3-formylphenyl)-1H-indole-1-carboxylate. yield 99%, $^1$H NMR (CDCl$_3$) δ: 1.69 (9H, s), 4.78 (2H, d, J=6.0 Hz), 6.61 (1H, d, J=3.9 Hz), 7.33 (1H, d, J=7.5 Hz), 7.44 (1H, t, J=7.5 Hz), 7.54-7.65 (4H, m), 7.77 (1H, d, J=1.8 Hz), 8.18 (1H, br s, J=8.4 Hz).

Reference Example 14

3-(5-chloro-3-methyl-1-benzothiophen-2-yl)benzaldehyde

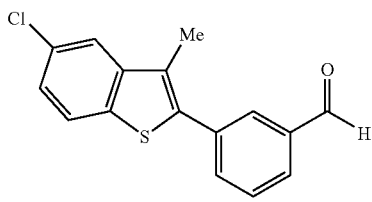

In the same manner as in Reference Example 5, the title compound was obtained as colorless needle crystals from 2-bromo-5-chloro-3-methyl-1-benzothiophene and (3-formylphenyl)boronic acid. yield 95%, $^1$H NMR (CDCl$_3$) δ: 2.45 (3H, s), 7.34 (1H, dd, J=1.8, 8.4 Hz), 7.60-8.06 (6H, m), 10.10 (1H, s).

Reference Example 15

[3-(5-chloro-3-methyl-1-benzothiophen-2-yl)phenyl]methanol

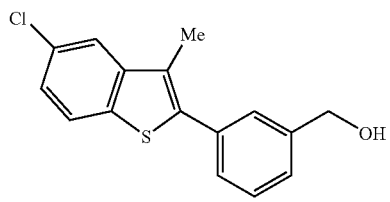

In the same manner as in Reference Example 8, the title compound was obtained as colorless needle crystals from 3-(5-chloro-3-methyl-1-benzothiophen-2-yl)benzaldehyde. yield 93%, $^1$H NMR (CDCl$_3$) δ: 1.70-1.80 (1H, m), 2.43 (3H, s), 4.78 (2H, br s), 7.31 (1H, dd, J=1.8, 8.4 Hz), 7.37-7.57 (4H, m), 7.69 (1H, d, J=1.8 Hz), 7.73 (1H, d, J=8.4 Hz).

Reference Example 16

3-(2-methyl-1H-indol-1-yl)benzaldehyde

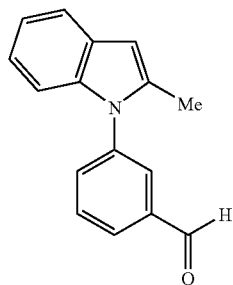

1-[3-(1,3-Dioxolan-2-yl)phenyl]-2-methyl-1H-indole (1.1 g, 3.94 mmol) synthesized according to the method described in *J. Am. Chem. Soc.*, 2002, vol. 124, pp. 11684-11688 was dissolved in tetrahydrofuran (40 mL), 5 N hydrochloric acid (10 mL) was added to the solution, and the mixture was stirred at 50° C. for 40 min. Water was added to the reaction solution and the mixture was extracted with ethyl acetate. The extract was washed with aqueous sodium chloride solution, dried over anhydrous magnesium sulfate, and concentrated under reduced pressure. The obtained residue was subjected to silica gel column chromatography (ethyl acetate:hexane=1:6) to give the title compound (50 mg, yield 5%) as a pale-yellow oil. MS: m/z 236 (MH$^+$).

Reference Example 17

[3-(2-methyl-1H-indol-1-yl)phenyl]methanol

In the same manner as in Reference Example 8, the title compound was obtained as a colorless oil from 3-(2-methyl-1H-indol-1-yl)benzaldehyde. yield 100%, $^1$H NMR (CDCl$_3$) δ: 2.30 (3H, s), 4.78 (2H, s), 6.39 (1H, s), 7.04-7.60 (8H, m).

Reference Example 18 methyl 4-[(2-phenyl-1H-indol-1-yl)methyl]benzoate

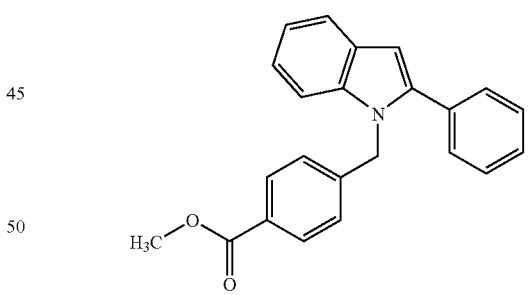

A mixed solution of 2-phenylindole (4.2 g, 21.7 mmol) and sodium hydride (60% in oil, 0.96 g, 24 mmol) in tetrahydrofuran (90 mL) and N,N-dimethylformamide (10 mL) was stirred under ice-cooling for 20 min. Methyl 4-bromomethylbenzoate (5.0 g, 21.8 mmol) was added to the reaction mixture, and the mixture was stirred at room temperature for 18 hr. Aqueous citric acid solution was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:10-1:5-

1:2) to give the title compound (2.8 g, yield 38%) as a pale-yellow oil. MS: m/z 342 (MH$^+$).

Reference Example 19

{4-[(2-phenyl-1H-indol-1-yl)methyl]phenyl}methanol

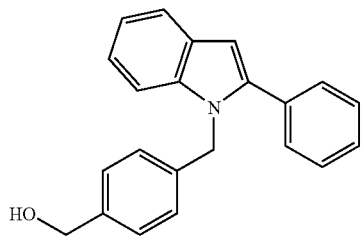

Methyl 4-[(2-phenyl-1H-indol-1-yl)methyl]benzoate (2.8 g, 8.20 mmol) was dissolved in anhydrous tetrahydrofuran (100 mL), and the mixture was ice-cooled. A 1.5 M diisobutylaluminum hydride toluene solution (13.5 mL, 20.3 mmol) was added dropwise to the solution. The solution was stirred under ice-cooling for 4 hr, and aqueous citric acid solution was added to the reaction solution. The mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:4-1:2) to give the title compound (2.25 g, yield 88%) as a colorless oil. MS: m/z 314 (MH$^+$).

Reference Example 20 ethyl (2E)-3-(2,6-difluoro-4-methoxyphenyl)acrylate

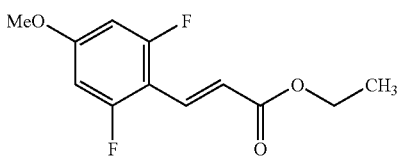

A solution of ethyl diethylphosphonoacetate (2.34 g, 10.4 mmol) and sodium hydride (60% in oil, 0.38 g, 9.50 mmol) in tetrahydrofuran (40 mL) was stirred under ice-cooling for 10 min. 2,6-Difluoro-4-methoxybenzaldehyde (1.5 g, 8.71 mmol) was added to the solution, and the mixture was stirred for 4 hr while raising the temperature to room temperature. The reaction mixture was diluted with ethyl acetate, and the mixture washed successively with aqueous citric acid solution, water and aqueous sodium chloride solution, dried over anhydrous magnesium sulfate, and concentrated under reduced pressure. The residue was subjected to silica gel column chromatography (ethyl acetate:hexane=1:10-1:5) to give the title compound (1.1 g, yield 52%) as colorless needle crystals. MS: m/z 243 (MH$^+$).

Reference Example 21 ethyl 3-(2,6-difluoro-4-methoxyphenyl)propanoate

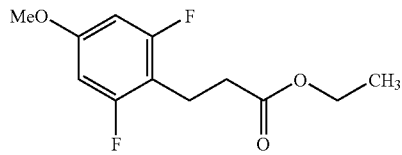

Ethyl (2E)-3-(2,6-difluoro-4-methoxyphenyl)acrylate (1.1 g, 4.54 mmol) was dissolved in a mixed solvent of tetrahydrofuran (30 mL) and ethanol (30 mL), 10% palladium-carbon (50% water-containing product, 0.30 g) was added, and the mixture was stirred under a hydrogen atmosphere at room temperature for 5 hr. The catalyst was filtered off and the obtained filtrate was concentrated to give the title compound (1.17 g, yield 100%) as a colorless oil. MS: m/z 245 (MH$^+$).

Reference Example 22 ethyl 3-(2,6-difluoro-4-hydroxyphenyl)propanoate

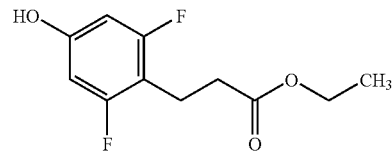

A solution of ethyl 3-(2,6-difluoro-4-methoxyphenyl)propanoate (1.17 g, 4.79 mmol), aluminum chloride (1.9 g, 14.2 mmol) and 1-octanethiol (1.7 mL, 9.80 mmol) in dichloromethane (20 mL) was stirred for 4 hr while raising the temperature from under ice-cooling to room temperature. The reaction mixture was poured into ice water, and the mixture was stirred for 1 hr. The mixture was extracted with dichloromethane. The extract washed with aqueous sodium chloride solution, dried over anhydrous magnesium sulfate, and concentrated under reduced pressure. The residue was subjected to silica gel column chromatography (ethyl acetate:hexane=1:10-1:5) to give the title compound (1.0 g, yield 91%) as a colorless oil. MS: m/z 231 (MH$^+$).

Reference Example 23 methyl 3-{4-[(3-bromobenzyl)oxy]phenyl}propanoate

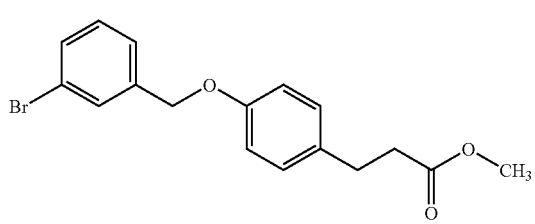

To a solution of methyl 3-(4-hydroxyphenyl)propanoate (0.3 g, 1.67 mmol) in N,N-dimethylformamide (4.0 mL) was added sodium hydride (60% in oil, 0.073 g, 1.83 mmol) with stirring under ice-cooling, and the mixture was stirred at the same temperature for 15 min. 3-Bromobenzyl bromide (0.44 g, 1.75 mmol) was added to the mixture with stirring under ice-cooling, and the mixture was stirred at room temperature for 2 hr. The reaction mixture was diluted with ethyl acetate, and the mixture washed with 5% aqueous potassium hydrogensulfate solution and saturated brine. The ethyl acetate layer was dried over anhydrous magnesium sulfate, and concentrated under reduced pressure to give the title compound (0.84 g, yield 72%) as a colorless powder. $^1$H NMR (CDCl$_3$) δ: 2.60 (2H, t, J=7.8 Hz), 2.90 (2H, t, J=7.8 Hz), 3.67 (3H, s), 5.01 (2H, s), 6.88 (2H, d, J=8.4 Hz), 7.12 (2H, d, J=8.4 Hz), 7.25 (1H, m), 7.35 (1H, d, J=7.5 Hz), 7.45 (1H, d, J=7.5 Hz), 7.59 (1H, s).

Reference Example 24 methyl 3-{4-[(4-bromobenzyl)oxy]phenyl}propanoate

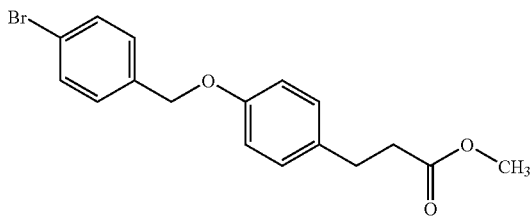

In the same manner as in Reference Example 23, the title compound was obtained as a colorless powder from methyl 3-(4-hydroxyphenyl)propanoate and 4-bromobenzyl bromide yield 72%, MS (ESI$^+$): 349 (MH$^+$), 351.

Reference Example 25 methyl 3-(4-{[4-(chloromethyl)benzyl[oxy}phenyl)propanoate

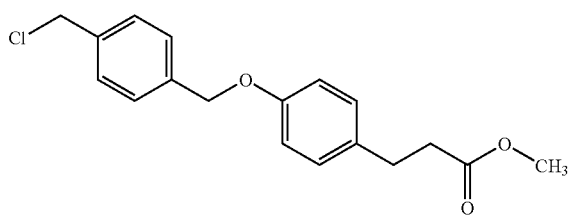

To a mixture of 4-(chloromethyl)benzyl alcohol (9.66 g, 61.1 mmol), methyl 3-(4-hydroxyphenyl)propanoate (10 g, 55.5 mmol), triphenylphosphine (18.9 g, 72.1 mmol) and tetrahydrofuran (200 mL) was added dropwise diethyl azodicarboxylate (40% toluene solution, 32.8 mL, 72.3 mmol) with stirring at 0° C., and the mixture was stirred at room temperature for 12 hr. After completion of the reaction, the reaction mixture was concentrated under reduced pressure, and the residue was purified by silica gel column chromatography (hexane/ethyl acetate=9/1-hexane/ethyl acetate=4/1) to give the title compound (9.89 g, yield 56%) as colorless crystals.

$^1$H NMR (CDCl$_3$) δ: 2.60 (2H, t, J=7.8 Hz), 2.89 (2H, t, J=7.8 Hz), 3.66 (3H, s), 4.60 (2H, s), 5.04 (2H, s), 6.89 (2H, d, J=8.7 Hz), 7.11 (2H, d, J=8.7 Hz), 7.34-7.45 (4H, m).

Reference Example 26

{4-[(2,5-diphenyl-1H-pyrrol-1-yl)methyl]phenyl}methanol

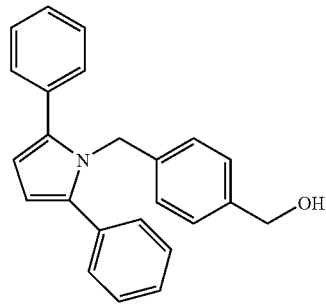

A mixture of methyl 4-aminomethylbenzoate hydrochloride (1.0 g, 4.96 mmol), 1,2-dibenzoylethane (1.2 g, 4.96 mmol) and acetic acid (10 mL) was heated under reflux for 4 days. After cooling, the reaction mixture was diluted with ethyl acetate, and the mixture washed with water, saturated aqueous sodium hydrogencarbonate and saturated brine, dried over anhydrous magnesium sulfate, and concentrated under reduced pressure. The residue was purified by silica gel column chromatography (hexane-hexane/ethyl acetate=6/1) to give a yellow oil (0.38 g). To a solution of the obtained oil in tetrahydrofuran (3.8 mL) was added lithium aluminum hydride (39 mg, 1.0 mmol) with stirring at 0° C., and the mixture was stirred at the same temperature for 2 hr. After completion of the reaction, sodium sulfate decahydrate (0.68 g, 2.1 mmol) was added to the reaction mixture, and the mixture was stirred at room temperature for 2 hr. The insoluble material was filtered off, and the filtrate was concentrated under reduced pressure. The residue was purified by silica gel column chromatography (hexane/ethyl acetate=4/1-hexane/ethyl acetate=1/1) to give the title compound (0.22 g, yield 13%) as a colorless oil. $^1$H NMR (CDCl$_3$) δ: 1.52 (1H, t, J=6.0 Hz), 4.59 (2H, d, J=6.0 Hz), 5.23 (2H, s), 6.36 (2H, s), 6.66 (2H, d, J=8.1 Hz), 7.13 (2H, d, J=8.1 Hz), 7.20-7.40 (10H, m).

Reference Example 27 ethyl (2E)-3-(2-fluoro-4-methoxyphenyl)acrylate

To a solution of ice-cooled ethyl diethylphosphonoacetate (9.45 g, 42.1 mmol) in tetrahydrofuran (50 mL) was added sodium hydride (60% in oil, 1.54 g, 38.5 mmol) and the mixture was stirred for 15 min. A solution of 2-fluoro-4-methoxybenzaldehyde (5.00 g, 32.4 mmol) in tetrahydrofuran (30 mL) was added dropwise. The mixture was stirred at room temperature for 2 hr, and water was added. The mixture was extracted with ethyl acetate. The extract washed with saturated brine, dried over anhydrous magnesium sulfate, and concentrated under reduced pressure. The residue was purified by silica gel column chromatography (20% ethyl acetate/hexane) to give the title compound (7.07 g, yield 97%) as a colorless oil. $^1$H NMR (CDCl$_3$) δ: 1.33 (3H, t, J=7.1 Hz), 3.83 (3H, s), 4.26 (2H, q, J=7.1 Hz), 6.41 (1H, d, J=16.2 Hz), 6.61-6.73 (2H, m), 7.45 (1H, t, J=8.6 Hz), 7.75 (1H, d, J=16.2 Hz).

Reference Example 28 ethyl 3-(2-fluoro-4-methoxyphenyl)propanoate

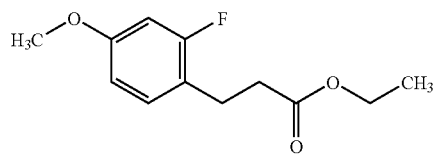

A mixture of ethyl (2E)-3-(2-fluoro-4-methoxyphenyl) acrylate (7.07 g, 31.5 mmol), tetrahydrofuran (50 mL), ethanol (5 mL) and platinum oxide (300 mg) was stirred overnight at room temperature under a hydrogen atmosphere. The catalyst was filtered off, and the filtrate was concentrated. The residue was purified by silica gel column chromatography (20% ethyl acetate/hexane) to give the title compound (5.97 g, yield 84%) as a colorless oil. $^1$H NMR (CDCl$_3$) δ: 1.23 (3H, t, J=7.2 Hz), 2.58 (2H, t, J=7.6 Hz), 2.90 (2H, t, J=7.6 Hz), 3.77 (3H, s), 4.12 (2H, q, J=7.2 Hz), 6.57-6.63 (2H, m), 7.07-7.13 (1H, m).

Reference Example 29 ethyl 3-(2-fluoro-4-hydroxyphenyl)propanoate

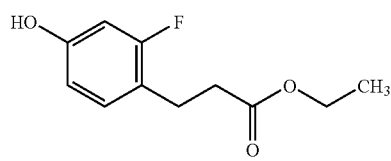

To a solution of ethyl 3-(2-fluoro-4-methoxyphenyl)propanoate (57.4 g, 254 mmol) and aluminum chloride (101 g, 761 mmol) in dichloromethane (250 mL) was added dropwise 1-octanethiol (74.3 g, 508 mmol), and the mixture was stirred at room temperature for 2 hr. The reaction mixture was poured into ice water, and the mixture was stirred for 30 min. The organic layer was separated, washed with saturated brine, dried over anhydrous magnesium sulfate, and concentrated under reduced pressure. The residue was purified by silica gel column chromatography (20% ethyl acetate/hexane) to give the title compound (44.6 g, yield 83%) as a colorless oil. $^1$H NMR (CDCl$_3$) δ: 1.23 (3H, t, J=7.2 Hz), 2.58 (2H, t, J=8.1 Hz), 2.89 (2H, t, J=8.1 Hz), 4.12 (2H, q, J=7.2 Hz), 6.51-6.56 (2H,m), 7.01-7.06 (1H, m).

Reference Example 30

5-fluoro-2-propyl-1H-indole

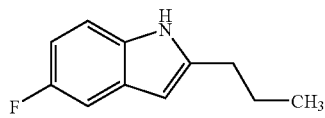

To a suspension of ethyltriphenylphosphonium bromide (0.86 g, 2.30 mmol) in tetrahydrofuran (20 mL) was added sodium hydride (60% in oil, 80 mg, 1.99 mmol) with stirring at room temperature, and the mixture was stirred at the same temperature for 20 min. To the solution was added 5-fluoro-1H-indole-2-carbaldehyde (0.25 g, 1.53 mmol) synthesized according to the method described in WO99/09025, and the mixture was stirred at 70° C. for 3 hr. After cooling, the reaction mixture was diluted with ethyl acetate, and the mixture washed with water and saturated brine, dried, and concentrated under reduced pressure. The residue was purified by silica gel column chromatography (hexane/ethyl acetate=10/1-hexane/ethyl acetate=4/1) to give a beige powder. A mixture of the obtained powder, 10% palladium-carbon (50% water-containing product, 0.1 g) and methanol (10 mL) was stirred under a hydrogen atmosphere for 3 hr. The catalyst was filtered off and the filtrate was concentrated under reduced pressure. The residue was purified by silica gel column chromatography (hexane/ethyl acetate=20/1-hexane/ethyl acetate=4/1) to give the title compound (0.18 g, yield 65%) as a colorless oil. MS (ESI+): 178 (M+H).

Reference Example 31

3-(chloromethyl)-4-isobutoxybenzaldehyde

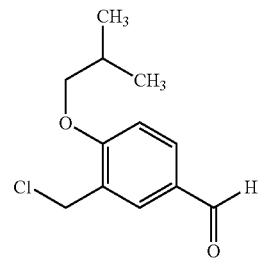

To a mixture of 4-isobutoxybenzaldehyde (6.9 g, 38.7 mmol), aluminum chloride (12.9 g, 96.8 mmol) and nitromethane (39 mL) was added methoxyacetyl chloride (4.1 mL, 44.5 mmol), with stirring at 0° C., and the mixture was stirred at the same temperature for 3 hr. After completion of the reaction, the reaction mixture was poured into ice water, and the mixture was extracted with ethyl acetate. The organic layer was dried over anhydrous magnesium sulfate, and concentrated under reduced pressure. The residue was purified by silica gel column chromatography (hexane/ethyl acetate=10/1-hexane/ethyl acetate=4/1) to give the title compound (5.22 g, yield 60%) as colorless crystals. $^1$H NMR (CDCl$_3$) δ: 1.08 (6H, d, J=6.9 Hz), 2.19 (1H, m), 3.89 (2H, d, J=6.0 Hz), 4.68 (2H, s), 6.98 (1H, d, J=8.4 Hz), 7.84 (1H, dd, J=2.1, 8.4 Hz), 7.91 (1H, d, J=2.1 Hz), 9.89 (1H, s).

Reference Example 32

4-isobutoxy-3-[(2-phenyl-1H-indol-1-yl)methyl]benzaldehyde

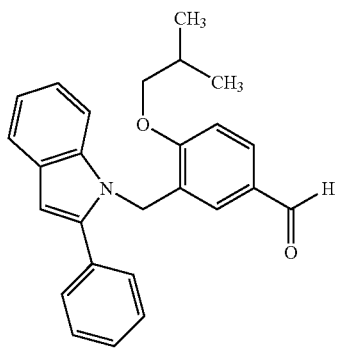

To a solution of 2-phenyl-1H-indole (0.94 g, 4.85 mmol) in N,N-dimethylformamide (10 mL) was added sodium hydride (60% in oil, 0.19 g, 4.85 mmol) with stirring at 0° C., and the mixture was stirred at the same temperature for 5 min. 3-(Chloromethyl)-4-isobutoxybenzaldehyde (1.0 g, 4.41 mmol) and sodium iodide (0.73 g, 4.85 mmol) were added to the obtained mixture and the mixture was stirred at the same temperature for 2 hr. After completion of the reaction, the reaction mixture was diluted with ethyl acetate, and the mixture was washed with 5% aqueous potassium hydrogensulfate solution and saturated brine, dried over anhydrous magnesium sulfate, and concentrated under reduced pressure. The residue was purified by silica gel column chromatography (hexane/ethyl acetate=10/1-hexane/ethyl acetate=4/1) to give the title compound (0.60 g, yield 36%) as colorless crystals.

$^1$H NMR (CDCl$_3$) δ: 1.03 (6H, d, J=6.9 Hz), 2.13 (1H, m), 3.88 (2H, d, J=6.6 Hz), 5.37 (2H, s), 6.71 (1H, s), 7.00 (1H, d, J=8.4 Hz), 7.09-7.20 (4H, m), 7.32-7.46 (5H, m), 7.69 (1H, m), 7.80 (1H, dd, J=2.1, 8.4 Hz), 9.64 (1H, s).

Reference Example 33

[4-isobutoxy-3-[(2-phenyl-1H-indol-1-yl)methyl]phenyl}methanol

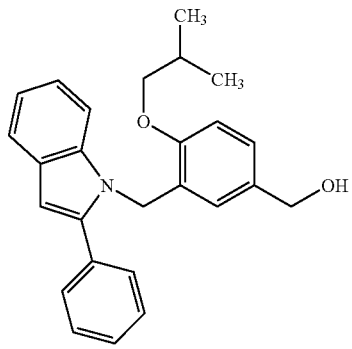

To a mixture of 4-isobutoxy-3-[(2-phenyl-1H-indol-1-yl)methyl]benzaldehyde (0.6 g, 1.56 mmol), methanol (3 mL) and tetrahydrofuran (6 mL) was added sodium borohydride (30 mg, 0.78 mmol) with stirring at 0° C., and the mixture was stirred at the same temperature for 1.5 hr. After completion of the reaction, the reaction mixture was diluted with ethyl acetate, and the mixture washed with 5% aqueous potassium hydrogensulfate solution and saturated brine, dried over anhydrous magnesium sulfate, and concentrated under reduced pressure. The residue was purified by silica gel column chromatography (hexane/ethyl acetate=10/1-hexane/ethyl acetate=1/1) to give the title compound (0.60 g, yield 99%) as a colorless oil. $^1$H NMR (CDCl$_3$) δ: 1.00 (6H, d, J=6.6 Hz), 1.37 (1H, t, J=6.0 Hz), 2.09 (1H, m), 3.79 (2H, d, J=6.6 Hz), 4.40 (2H, d, J=6.0 Hz), 5.36 (2H, s), 6.62 (1H, d, J=1.8 Hz), 6.68 (1H, s), 6.88 (1H, d, J=8.1 Hz), 7.10-7.18 (3H, m), 7.23 (1H, d, J=2.1, 8.4 Hz), 7.29-7.48 (5H, m), 7.68 (1H, m).

Reference Example 34

{3-[(2-phenyl-1H-indol-1-yl)methyl]phenyl}methanol

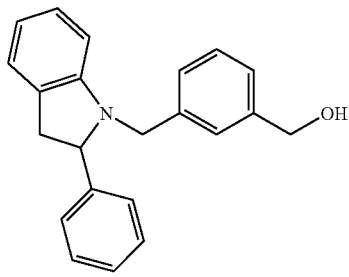

To a solution of 2-phenyl-1H-indole (4.64 g, 24.0 mmol) in N,N-dimethylformamide (50 mL) was added sodium hydride (60% in oil, 0.96 g, 24.0 mmol) with stirring at 0° C., and the mixture was stirred at the same temperature for 10 min. Methyl 3-(bromomethyl)benzoate (5.0 g, 21.8 mmol) was added to the obtained mixture, and the mixture was stirred at the same temperature for 2 hr. After completion of the reaction, the reaction mixture was diluted with ethyl acetate, and the mixture washed with 5% aqueous potassium hydrogensulfate solution and saturated brine, dried over anhydrous magnesium sulfate, and concentrated under reduced pressure to give methyl 3-[(2-phenyl-1H-indol-1-yl)methyl]benzoate (3.67 g). Then, to a solution of the product in tetrahydrofuran (37 mL) was added lithium aluminum hydride (0.41 g, 10.7 mmol) with stirring at 0° C., and the mixture was stirred at the same temperature for 2 hr. After completion of the reaction, sodium hydrogensulfate decahydrate (6.9 g, 21.4 mmol) was added to the reaction mixture, and the mixture was stirred at room temperature for 2 hr. The insoluble material was filtered off, and the filtrate was concentrated under reduced pressure. The residue was purified by silica gel column chromatography (hexane/ethyl acetate=10/1-hexane/ethyl acetate=1/1) to give the title compound (2.63 g, yield 79%) as a yellow oil. $^1$H NMR (CDCl$_3$) δ: 1.57 (1H, m), 4.62 (2H, d, J=2.1 Hz), 5.37

(2H, s), 6.66 (1H, s), 6.93 (1H, m), 7.07 (1H, s), 7.11-7.20 (3H, m), 7.22-7.31 (2H, m), 7.33-7.48 (5H, m), 7.67 (1H, m).

Reference Example 35

4-isobutoxy-3-[(2-methyl-3,4-dihydroquinolin-1(2H)-yl)methyl]benzaldehyde

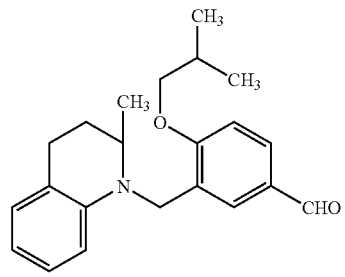

In the same manner as in Reference Example 32, the title compound was obtained as a yellow oil from 3-(chloromethyl)-4-isobutoxybenzaldehyde and 2-methyl-1,2,3,4-tetrahydroquinoline. yield 91%, $^1$H NMR (CDCl$_3$) δ: 1.09 (6H, d, J=6.6 Hz), 1.21 (3H, d, J=6.3 Hz), 1.90 (1H, m), 2.03-2.28 (2H, m), 2.81 (1H, m), 2.95 (1H, m), 3.59 (1H, m), 3.90 (2H, d, J=6.3 Hz), 4.42 (1H, d, J=18.3 Hz), 4.55 (1H, d, J=18.3 Hz), 6.26 (1H, d, J=7.5 Hz), 6.58 (1H, m), 6.88-7.04 (3H, m), 7.67 (1H, m), 7.78 (1H, dd, J=2.1, 8.4 Hz), 9.79 (1H, s).

Reference Example 36

5-[(E)-2-phenylvinyl]-3-[4-(trifluoromethyl)phenyl]-1H-pyrazole

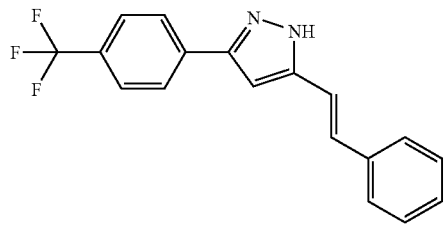

3-[4-(Trifluoromethyl)phenyl]-1H-pyrazole-5-carbaldehyde (1.20 g, 5.00 mmol) was dissolved in N,N-dimethylformamide (10 mL), benzyltriphenylphosphonium bromide (3.25 g, 7.50 mmol) and potassium carbonate (2.76 g, 20.0 mmol) were added, and the mixture was stirred at room temperature for 14 hr. The reaction mixture was poured into water, and the mixture was extracted with ethyl acetate. The ethyl acetate layer was dried over anhydrous magnesium sulfate, and concentrated under reduced pressure. The residue was purified by silica gel column chromatography (hexane:ethyl acetate=19:1-1:2) to give the title compound (630 mg, yield 40%) as colorless crystals. MS: m/z 315 (MH$^+$), $^1$H NMR (CDCl$_3$) δ: 6.79 (1H, s), 6.99 (1H, d, J=16.5 Hz), 7.10 (1H, d, J=16.5 Hz), 7.28-7.39 (3H, m), 7.41-7.47 (2H, m), 7.64 (2H, d, J=8.5 Hz), 7.87 (2H, d, J=8.0 Hz), 10.90 (1H, s).

Reference Example 37

5-(2-phenylethyl)-3-[4-(trifluoromethyl)phenyl]-1H-pyrazole

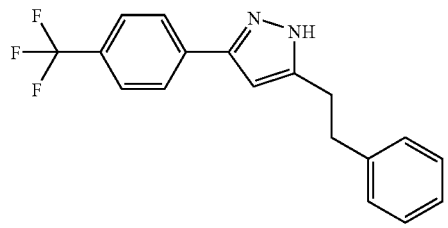

5-[(E)-2-Phenylvinyl]-3-[4-(trifluoromethyl)phenyl]-1H-pyrazole (1.56 g, 4.96 mmol) was dissolved in a mixed solvent of tetrahydrofuran (30 mL) and ethanol (30 mL), 10% palladium-carbon (50% water-containing product, 500 mg) was added, and the mixture was stirred at room temperature under an atmospheric hydrogen atmosphere for 2 hr. The catalyst was filtered off and the filtrate was concentrated to give the title compound (880 mg, yield 56%) as colorless crystals. MS: m/z 317 (MH$^+$).

Reference Example 38

3-bromo-1-(2-ethoxyethyl)-2-phenyl-1H-indole

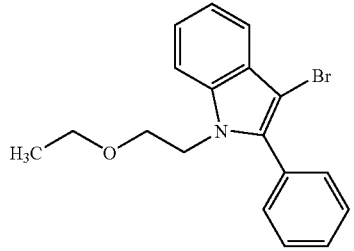

Under ice-cooling, sodium hydride (60% in oil, 0.48 g, 12.0 mmol) was added to a solution of 3-bromo-2-phenyl-1H-indole (2.72 g, 10.0 mmol) in N,N-dimethylformamide (10 mL) by small portions, and the mixture was stirred under a nitrogen atmosphere at the same temperature for 30 min. 2-Chloroethyl ethyl ether (1.65 mL, 15.0 mmol) was added to the reaction mixture, and the mixture was stirred at 70° C. for 3 hr. Water was added to the reaction mixture, and the mixture was extracted with ethyl acetate. The extract washed with saturated brine, dried over anhydrous magnesium sulfate, and concentrated under reduced pressure. The residue was purified by silica gel column chromatography (hexane-25% ethyl acetate/hexane) to give the title compound (2.60 g, yield 76%) as a red oil. MS: m/z 344 (MH$^+$).

Reference Example 39

3-[1-(2-ethoxyethyl)-2-phenyl-1H-indol-3-yl]benzaldehyde

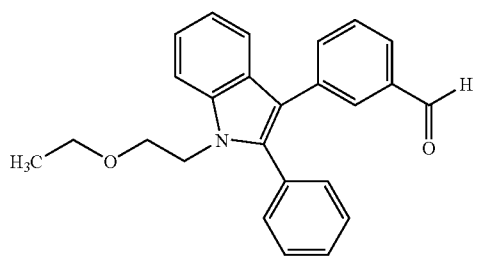

In the same manner as in Reference Example 1, the title compound was obtained as a yellow oil from 3-bromo-1-(2-ethoxyethyl)-2-phenyl-1H-indole and (3-formylphenyl)boronic acid. yield 30%, MS: m/z 370 (MH$^+$).

Reference Example 40

{3-[1-(2-ethoxyethyl)-2-phenyl-1H-indol-3-yl]phenyl}methanol

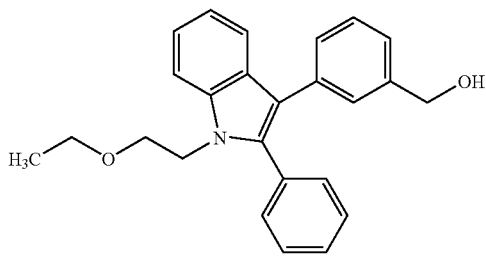

In the same manner as in Reference Example 2, the title compound was obtained as a colorless oil from 3-[1-(2-ethoxyethyl)-2-phenyl-1H-indol-3-yl]benzaldehyde. Yield 97%, MS: m/z 372 (MH$^+$).

Reference Example 41

{4-[(3-methyl-5-phenyl-1H-pyrazol-1-yl)methyl]phenyl}methanol

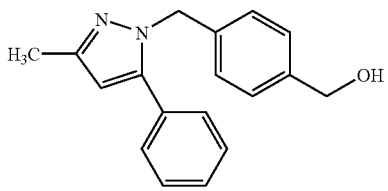

A mixture of 3-methyl-5-phenyl-1H-pyrazole (760 mg, 5.0 mmol), [4-(chloromethyl)phenyl]methanol (850 mg, 5.43 mmol), potassium carbonate (1.38 g, 10.0 mmol) and N,N-dimethylformamide (20 mL) was stirred at 120° C. for 1 hr. The reaction mixture was poured into 10% aqueous citric acid solution, and the mixture was extracted with ethyl acetate. The ethyl acetate layer was dried using a Presep Dehydration tube (manufactured by Wako Pure Chemical Industries, Ltd.) and concentrated. The residue was purified by silica gel column chromatography (10%-80% ethyl acetate/hexane) to give the title compound (850 mg, yield 61%) as colorless crystals. $^1$H NMR (CDCl$_3$) δ: 2.21 (3H, s), 4.66 (2H, s), 5.33 (2H, s), 6.38 (1H, s), 7.13 (2H, d, J=8.1 Hz), 7.27-7.34 (3H, m), 7.34-7.42 (2H, m), 7.77-7.83 (2H, m).

Reference Example 42

{4-[(5-methyl-3-phenyl-1H-pyrazol-1-yl)methyl]phenyl}methanol

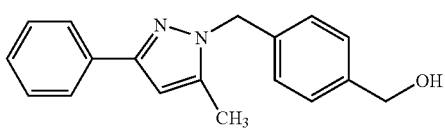

The title compound (205 mg, yield 14%) was obtained as colorless crystals from a fraction eluted later by silica gel column chromatography in Reference Example 41. $^1$H NMR (CDCl$_3$) δ: 1.66 (1H, t, J=5.8 Hz), 2.33 (3H, s), 4.65 (2H, d, J=5.7 Hz), 5.27 (2H, s), 6.14 (1H, s), 7.04 (2H, d, J=8.3 Hz), 7.24-7.28 (1H, m), 7.28-7.33 (3H, m), 7.34-7.41 (3H, m).

Reference Example 43

{4-[(3-isopropyl-5-phenyl-1H-pyrazol-1-yl)methyl]phenyl)methanol

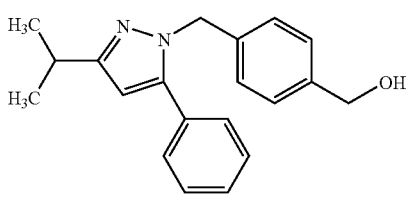

In the same manner as in Reference Example 41, the title compound (285 mg, yield 9%) was obtained as a colorless oil from 3-isopropyl-5-phenyl-1H-pyrazole and [4-(chloromethyl)phenyl]methanol. $^1$H NMR (CDCl$_3$) δ: 1.32 (6H, d, J=7.0 Hz), 1.64 (1H, t, J=5.8 Hz), 2.99-3.09 (1H, m), 4.66 (2H, d, J=5.8 Hz), 5.30 (2H, s), 6.18 (1H, s), 6.97-7.06 (2H, m), 7.24-7.39 (7H, m).

Reference Example 44

{4-isobutoxy-3-[(2-methyl-3,4-dihydroquinolin-1 (2H)-yl)methyl]phenyl}methanol

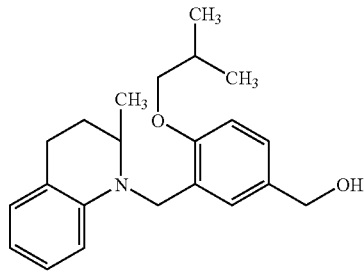

In the same manner as in Reference Example 33, the title compound was obtained as a colorless oil from 4-isobutoxy-3-[(2-methyl-3,4-dihydroquinolin-1 (2H)-yl)methyl]benzaldehyde. yield 94%, $^1$H NMR (CDCl$_3$) δ: 1.07 (6H, d, J=6.6 Hz), 1.20 (3H, d, J=6.6 Hz), 1.42 (1H, t, J=5.7 Hz), 1.86 (1H, m), 2.01-2.22 (2H, m), 2.77 (1H, m), 2.94 (1H, m), 3.58 (1H, m), 3.80 (2H, d, J=6.3 Hz), 4.41 (1H, d, J=18.3 Hz), 4.48-4.60 (3H, m), 6.32 (1H, d, J=7.8 Hz), 6.55 (1H, m), 6.85 (1H, d, J=8.4 Hz), 6.93 (1H, m), 7.00 (1H, d, J=7.2 Hz), 7.13 (1H, d, J=2.1 Hz), 7.21 (1H, dd, J=2.1, 8.4 Hz).

Reference Example 45

{4-[(2-methyl-1H-indol-1-yl)methyl]phenyl}methanol

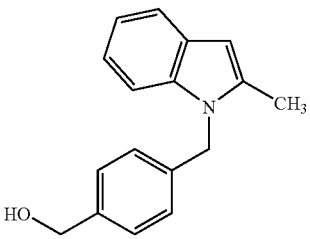

In the same manner as in Reference Example 18 and Reference Example 19, the title compound was obtained as pale-yellow crystals from 2-methylindole. (yield 14%, 2 steps), MS: m/z 252 (MH$^+$).

Reference Example 46

3-[(3,5-dimethyl-1H-pyrazol-1-yl)methyl]-4-isobutoxybenzaldehyde

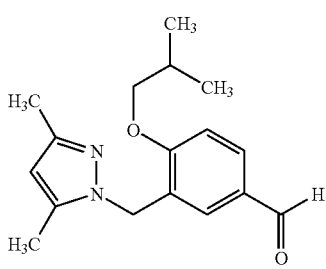

In the same manner as in Reference Example 32, the title compound was obtained as colorless crystals from 3-(chloromethyl)-4-isobutoxybenzaldehyde and 3,5-dimethylpyrazole. yield 90%, MS (ESI+): 287 (M+H).

Reference Example 47

{3-[(3,5-dimethyl-1H-pyrazol-1-yl)methyl]-4-isobutoxyphenyl}methanol

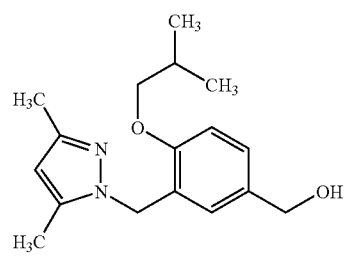

In the same manner as in Reference Example 33, the title compound was obtained as a colorless oil from 3-[(3,5-dimethyl-1H-pyrazol-1-yl)methyl]-4-isobutoxybenzaldehyde. yield 80%, MS (ESI+): 289 (M+H).

Reference Example 48 methyl 3-isopropoxy-4-methylbenzoate

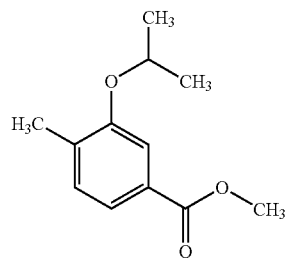

To a mixture of methyl 3-hydroxy-4-methylbenzoate (5.28 g, 31.8 mmol), potassium carbonate (6.59 g, 47.7 mmol) and N,N-dimethylformamide (50 mL) were added 2-bromopropane (3.58 mL, 38.2 mmol) and potassium iodide (0.53 g, 3.18 mmol) with stirring at room temperature, and the mixture was stirred at 80° C. for 7 hr. 2-Bromopropane (1.79 mL, 19.1 mmol) and potassium iodide (0.27 g, 1.59 mmol) were added to the reaction mixture, and the mixture was further stirred at 80° C. for 15 hr. The reaction mixture was cooled, and diluted with ethyl acetate. The mixture washed with water and saturated brine, dried over anhydrous magnesium sulfate, and concentrated under reduced pressure. The residue was purified by silica gel column chromatography (hexane/ethyl acetate=19/1-hexane/ethyl acetate=4/1) to give the title compound (6.3 g, yield 96%) as a colorless oil. MS (ESI+): 209 (M+H).

Reference Example 49 methyl 4-(bromomethyl)-3-isopropoxybenzoate

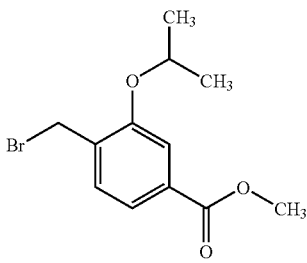

To a solution of methyl 3-isopropoxy-4-methylbenzoate (1.0 g, 4.8 mmol) in ethyl acetate (20 mL) were added N-bromosuccinimide (0.92 g, 5.19 mmol) and 2,2'-azobis(isobutyronitrile) (3 mg), and the mixture was heated under reflux for 6 hr. The reaction mixture was cooled, washed with water and saturated brine, dried over anhydrous magnesium sulfate, and concentrated under reduced pressure. The residue was purified by silica gel column chromatography (hexane/ethyl acetate=10/1-hexane/ethyl acetate=4/1) to give the title compound (0.89 g, yield 64%) as a colorless oil. MS (ESI+): 287 (M+H), 289.

Reference Example 50 methyl 4-[(3,5-diphenyl-1H-pyrazol-1-yl)methyl]-3-isopropoxybenzoate

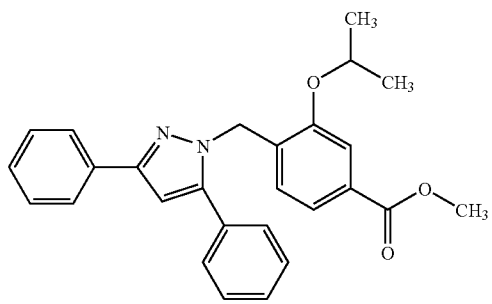

To a solution of 3,5-diphenyl-1H-pyrazole (0.36 g, 1.65 mmol) in N,N-dimethylformamide (8.6 mL) was added sodium hydride (60% in oil, 66 mg, 1.65 mmol) with stirring at room temperature, and the mixture was stirred at the same temperature for 30 min. A solution of methyl 4-(bromomethyl)-3-isopropoxybenzoate (0.43 g, 1.50 mmol) in N,N-dimethylformamide (4.3 mL) and sodium iodide (22 mg, 0.15 mmol) were added to the reaction mixture, and the mixture was stirred at room temperature for 3 hr. The reaction mixture was diluted with ethyl acetate, and the mixture washed with water and saturated brine, dried over anhydrous magnesium sulfate, and concentrated under reduced pressure. The residue was purified by silica gel column chromatography (hexane/ethyl acetate=10/1-hexane/ethyl acetate=4/1) to give the title compound (0.59 g, yield 92%) as a colorless oil. MS (ESI+): 427 (M+H).

Reference Example 51

(4-[(3,5-diphenyl-1H-pyrazol-1-yl)methyl]-3-isopropoxyphenyl}methanol

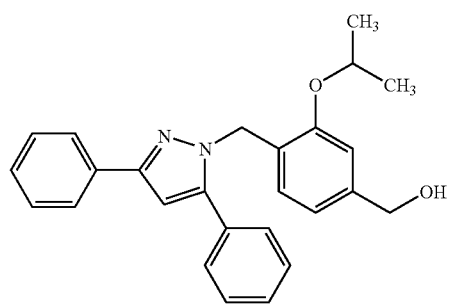

To a solution of methyl 4-[(3,5-diphenyl-1H-pyrazol-1-yl) methyl]-3-isopropoxybenzoate (0.59 g, 1.38 mmol) in tetrahydrofuran (12 mL) was added lithium aluminum hydride (52 mg, 1.38 mmol) with stirring at 0° C., and the mixture was stirred at the same temperature for 2.5 hr. After completion of the reaction, sodium sulfate decahydrate (0.89 g, 2.76 mmol) was added to the reaction mixture, and the mixture was stirred at room temperature for 2 hr. The insoluble material was filtered off, and the filtrate was concentrated under reduced pressure. The residue was purified by silica gel column chromatography (hexane/ethyl acetate=5/1-hexane/ethyl acetate=1/1) to give the title compound (0.50 g, yield 92%) as a colorless oil. MS (ESI+): 399 (M+H).

Reference Example 52

3-bromo-1-(2-ethoxyethyl)-2-methyl-1H-indole

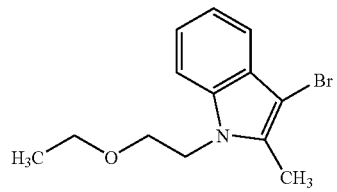

Under ice-cooling, sodium hydride (60% in oil, 1.44 g, 36.0 mmol) was added to a solution of 3-bromo-2-methyl-1H-indole (6.30 g, 30.0 mmol) in N,N-dimethylformamide (30 mL) by small portions, and the mixture was stirred under a nitrogen atmosphere at the same temperature for 1 hr. 2-Bromoethyl ethyl ether (5.07 mL, 45.0 mmol) and sodium iodide (0.747 g, 4.50 mmol) were added to the reaction mixture, and the mixture was stirred at 70° C. for 6 hr. The reaction mixture was concentrated under reduced pressure, water was added and the mixture was extracted with ethyl acetate. The extract was washed with saturated brine, dried over anhydrous magnesium sulfate, and concentrated under reduced pressure. The residue was purified by silica gel column chromatography (hexane-25% ethyl acetate/hexane) to give the title compound (6.30 g, yield 74%) as a dark-purple oil. MS m/z 282 (MH+).

Reference Example 53

3-[1-(2-ethoxyethyl)-2-methyl-1H-indol-3-yl]benzaldehyde

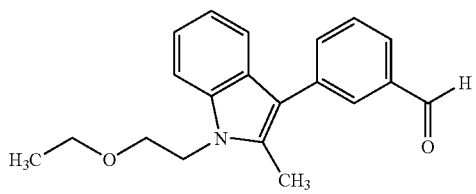

In the same manner as in Reference Example 1, the title compound was obtained as a yellow oil from 3-bromo-1-(2-ethoxyethyl)-2-methyl-1H-indole and (3-formylphenyl)boronic acid. yield 13%, MS m/z 308 (MH+).

Reference Example 54

{3-[1-(2-ethoxyethyl)-2-methyl-1H-indol-3-yl]phenyl}methanol

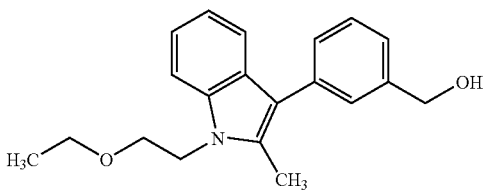

In the same manner as in Reference Example 2, the title compound was obtained as a colorless oil from 3-[1-(2-ethoxyethyl)-2-methyl-1H-indol-3-yl]benzaldehyde. yield 92%, MS m/z 310 (MH+).

Reference Example 55 ethyl 3-tert-butyl-1-{4-[(methoxymethoxy)methyl]benzyl}-1H-pyrazole-5-carboxylate

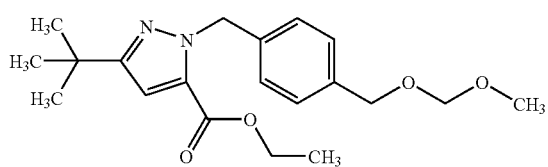

A mixed solution of ethyl 3-tert-butyl-1H-pyrazole-5-carboxylate (3.00 g, 15.3 mmol), [4-(chloromethyl)phenyl]methanol (2.50 g, 16.0 mmol), potassium carbonate (2.11 g, 15.3 mmol) and N,N-dimethylformamide (40 mL) was stirred at 70° C. for 3 hr. Water was added to the reaction solution, and the mixture was extracted with ethyl acetate. The extract washed with aqueous sodium chloride solution, dried over anhydrous magnesium sulfate, and concentrated under reduced pressure. To a mixture of the obtained oil, N-ethyldiisopropylamine (8.00 mL, 45.9 mmol) and tetrahydrofuran (50 mL) was added dropwise a solution of chloromethyl methyl ether (4.40 mL, 46.3 mmol) in tetrahydrofuran (10 mL) at 0° C. The reaction mixture was stirred overnight at room temperature, and concentrated, and the obtained residue was subjected to silica gel chromatography (ethyl acetate: hexane=1:3) to give the title compound (1.95 g, yield 35%) as a colorless oil. $^1$H NMR (CDCl$_3$) δ: 1.31 (1H, t, J=7.1 Hz), 1.32 (9H, s), 3.39 (3H, s), 4.26 (2H, q, J=7.1 Hz), 4.54 (2H, s), 4.68 (2H, s), 5.70 (2H, s), 6.71 (1H, s), 7.15-7.33 (4H, m).

Reference Example 56

(3-tert-butyl-1-{4-[(methoxymethoxy)methyl]benzyl}-1H-pyrazol-5-yl)methanol

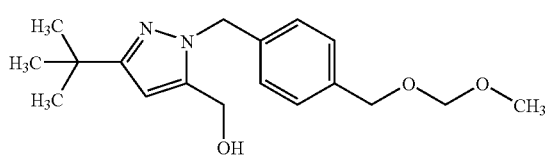

To a solution of ethyl 3-tert-butyl-1-{4-[(methoxymethoxy)methyl]benzyl}-1H-pyrazole-5-carboxylate (1.95 g, 5.41 mmol) in tetrahydrofuran (20 mL) was added lithium aluminum hydride (0.26 g, 5.5 mmol) under ice-cooling, and the mixture was stirred at room temperature for 30 min. Ethanol (10 mL) and saturated aqueous ammonium chloride solution (1.0 mL) were added to the reaction mixture. The precipitated insoluble material was filtered off, and the filtrate was concentrated under reduced pressure. The obtained residue subjected to silica gel chromatography (ethyl acetate:hexane=1:1) to give the title compound (1.45 g, yield 84%) as a colorless oil.

$^1$H NMR (CDCl$_3$) δ: 1.32 (9H, s), 1.57 (1H, t, J=6.0 Hz), 3.39 (3H, s), 4.49 (2H, d, J=6.2 Hz), 4.68 (2H, s), 5.36 (2H, s), 5.55 (2H, s), 6.10 (1H, s), 7.05-7.13 (2H, m), 7.24-7.33 (2H, m).

Reference Example 57

3-tert-butyl-1-[{4-[(methoxymethoxy)methyl]benzyl}-5-(phenoxymethyl)-1H-pyrazole

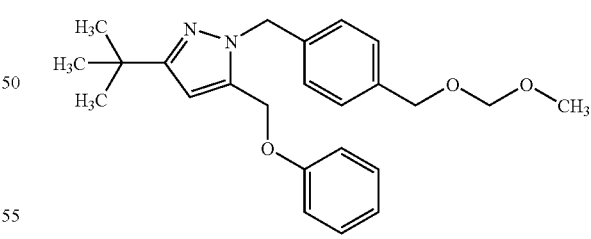

To a mixture of (3-tert-butyl-1-{4-[(methoxymethoxy)methyl]benzyl}-1H-pyrazol-5-yl)methanol (1.45 g, 4.55 mmol), phenol (0.47 g, 5.0 mmol), tributylphosphine (2.27 mL, 9.11 mmol) and tetrahydrofuran (70 mL) was added 1,1'-(azodicarbonyl)dipiperidine (2.30 g, 9.12 mmol), and the mixture was stirred at room temperature for 2 hr. The reaction solution was concentrated, and diisopropyl ether was added to the residue. The insoluble material was filtered off, and the filtrate was concentrated under reduced pressure. The residue was subjected to silica gel column chromatography (ethyl acetate:hexane=1:3) to give the title compound (1.66 g, yield 93%) as a colorless oil. $^1$H NMR (CDCl$_3$) δ: 1.33 (9H, s), 3.40 (3H, s), 4.55 (2H, s), 4.68 (2H, s), 4.83 (2H, s), 5.37 (2H, s), 6.21 (1H, s), 6.80-7.10 (5H, m), 7.18-7.32 (4H, m).

Reference Example 58

(4-{[3-tert-butyl-5-(phenoxymethyl)-1H-pyrazol-1-yl]methyl}phenyl)methanol

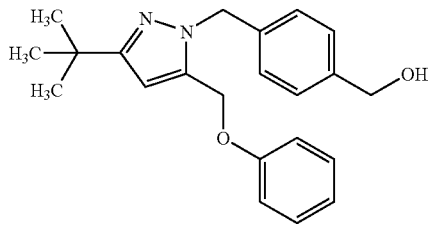

A mixture of 3-tert-butyl-1-{4-[(methoxymethoxy)methyl]benzyl)-5-(phenoxymethyl)-1H-pyrazole (1.66 g, 4.21 mmol), concentrated hydrochloric acid (0.2 mL) and methanol (20 mL) was refluxed overnight. Water was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:1) to give the title compound (1.35 g, yield 91%) as a colorless oil.

$^1$H NMR (CDCl$_3$) δ 1.34 (9H, s), 4.65 (2H, s), 4.83 (2H, s), 5.37 (2H, s), 6.21 (1H, s), 6.80-7.10 (5H, m), 7.20-7.34 (4H, m).

Reference Example 59 methyl 4-[(3-tert-butyl-5-{[4-(methoxycarbonyl)benzyl]oxy}-1H-pyrazol-1-yl)methyl]benzoate

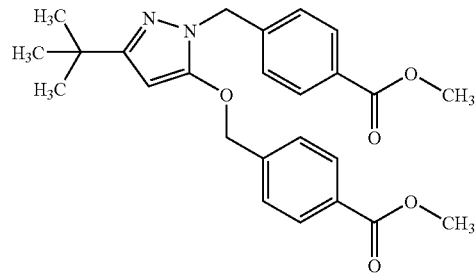

A mixture of 5-tert-butyl-2,4-dihydro-3H-pyrazol-3-one (5.00 g, 35.7 mmol), methyl 4-(bromomethyl)benzoate (17.16 g, 74.91 mmol), potassium carbonate (10.5 g, 76.0 mmol) and N,N-dimethylformamide (50 mL) was stirred overnight at 60° C. Water was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:3) to give the title compound (6.90 g, yield 44%) as a colorless oil. melting point 93-94° C.

Reference Example 60 methyl 4-[(3-tert-butyl-5-oxo-4,5-dihydro-1H-pyrazol-1-yl)methyl]benzoate

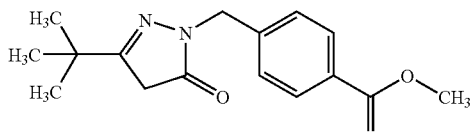

A mixture of methyl 4-[(3-tert-butyl-5-{[4-(methoxycarbonyl)benzyl]oxy}-1H-pyrazol-1-yl)methyl]benzoate (6.90 g, 15.8 mmol), 10% palladium-carbon (50% water-containing product, 0.35 g) and tetrahydrofuran (50 mL) was stirred overnight at room temperature under a hydrogen atmosphere. The catalyst was filtered off and the obtained filtrate was concentrated to give the title compound (3.70 g, yield 81%) as colorless crystals. melting point 161-162° C.

Reference Example 61 methyl 4-{[5-(benzyloxy)-3-tert-butyl-1H-pyrazol-1-yl]methyl}benzoate

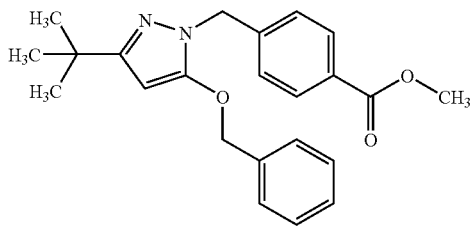

A mixture of methyl 4-[(3-tert-butyl-5-oxo-4,5-dihydro-1H-pyrazol-1-yl)methyl]benzoate (2.00 g, 6.94 mmol), benzyl bromide (0.91 mL, 7.7 mmol), potassium carbonate (0.96 g, 6.9 mmol) and N,N-dimethylformamide (25 mL) was stirred overnight at room temperature. Water was added to the reaction solution, and the mixture was extracted with ethyl acetate. The extract washed with aqueous sodium chloride solution, dried over anhydrous magnesium sulfate, and concentrated under reduced pressure. The residue subjected to silica gel column chromatography (ethyl acetate:hexane=1:3) to give the title compound (2.14 g, yield 81%) as a yellow oil.

$^1$H NMR (CDCl$_3$) δ: 1.29 (9H, s), 3.90 (3H, s), 5.01 (2H, s), 5.19 (2H, s), 5.49 (1H, s), 7.00-7.37 (7H, m), 7.92-8.00 (2H, m).

Reference Example 62

(4-{[5-(benzyloxy)-3-tert-butyl-1H-pyrazol-1-yl]methyl}phenyl)methanol

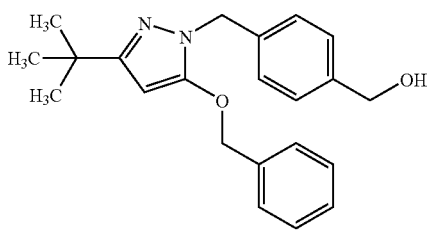

To a solution of methyl 4-([5-(benzyloxy)-3-tert-butyl-1H-pyrazol-1-yl]methyl]benzoate (2.14 g, 5.65 mmol) in tetrahydrofuran (20 mL) was added lithium aluminum hydride (0.27 g, 5.7 mmol) under ice-cooling, and the mixture was stirred at room temperature for 30 min. Ethanol (10 mL) and saturated aqueous ammonium chloride solution (1.0 mL) were added to the reaction mixture. The precipitated insoluble material was filtered off, and the filtrate was concentrated under reduced pressure. The residue was subjected to silica gel chromatography (ethyl acetate:hexane=1:1) to give the title compound (1.97 g, yield 99%) as a colorless oil. $^1$H NMR (CDCl$_3$) δ: 1.28 (9H, s), 1.77 (1H, br t), 4.62-4.70 (2H, m), 5.00 (2H, s), 5.13 (2H, s), 5.47 (1H, s), 7.08-7.38 (9H, m).

Reference Example 63 methyl 4-({3-tert-butyl-5-[(6-methylpyridin-2-yl)methoxy]-1H-pyrazol-1-yl}methyl)benzoate

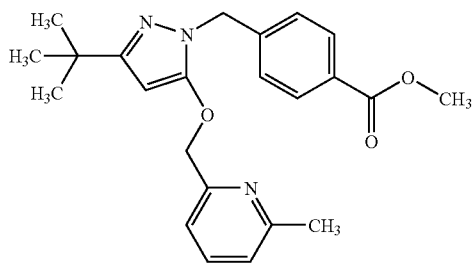

To a mixture of methyl 4-[(3-tert-butyl-5-oxo-4,5-dihydro-1H-pyrazol-1-yl)methyl]benzoate (1.68 g, 5.83 mmol), (6-methylpyridin-2-yl)methanol (0.79 g, 6.4 mmol), tributylphosphine (2.90 mL, 11.6 mmol) and tetrahydrofuran (80 mL) was added 1,1'-(azodicarbonyl)dipiperidine (2.94 g, 11.7 mol), and the mixture was stirred at room temperature for 2 hr. The reaction solution was concentrated, and diisopropyl ether was added to the residue. The insoluble material was filtered off, and the filtrate was concentrated under reduced pressure. The residue was subjected to silica gel column chromatography (ethyl acetate:hexane=2:3) to give the title compound (2.14 g, yield 93%) as a yellow oil. $^1$H NMR (CDCl$_3$) δ: 1.27 (9H, s), 2.54 (3H, s), 3.90 (3H, s), 5.11 (2H, s), 5.25 (2H, s), 5.47 (1H, s), 6.96 (1H, d, J=7.8 Hz), 7.06 (1H, d, J=7.8 Hz), 7.19 (2H, d, J=8.6 Hz), 7.51 (1H, t, J=7.7 Hz), 7.93-8.00 (2H, m).

Reference Example 64

[4-({3-tert-butyl-5-[(6-methylpyridin-2-yl)methoxy]-1H-pyrazol-1-yl}methyl)phenyl]methanol

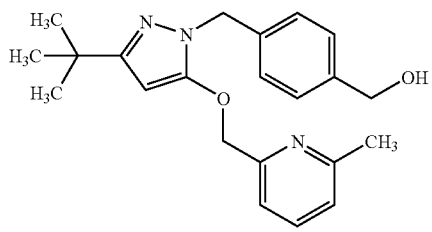

To a solution (20 mL) of methyl 4-({3-tert-butyl-5-[(6-methylpyridin-2-yl)methoxy]-1H-pyrazol-1-yl}methyl)benzoate (2.14 g, 5.44 mmol) in tetrahydrofuran was added lithium aluminum hydride (0.26 g, 5.5 mmol) under ice-cooling, and the mixture was stirred at room temperature for 30 min. Ethanol (10 mL) and saturated aqueous ammonium chloride solution (1.0 mL) were added to the reaction mixture. The precipitated insoluble material was filtered off, and the filtrate was concentrated under reduced pressure. The residue was subjected to silica gel chromatography (ethyl acetate:hexane=3:1) to give the title compound (1.86 g, yield 94%) as a yellow oil. $^1$H NMR (CDCl$_3$) δ: 1.26 (9H, s), 2.24 (1H, br s), 2.53 (3H, s), 4.64 (2H, br s), 5.09 (2H, s), 5.17 (2H, s), 5.43 (1H, s), 6.97-7.08 (2H, m), 7.10-7.16 (2H, m), 7.23-7.30 (2H, m), 7.51 (1H, t, J=7.8 Hz).

Reference Example 65

{4-[(3-tert-butyl-5-phenyl-1H-pyrazol-1-yl)methyl]phenyl}methanol

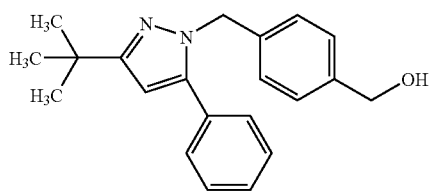

In the same manner as in Reference Example 41, the title compound was obtained as a colorless oil from 3-tert-butyl-5-phenyl-1H-pyrazole. yield 20%, $^1$H NMR (CDCl$_3$) δ: 1.37

(9H, s), 1.68 (1H, t, J=5.9 Hz), 4.65 (2H, d, J=5.9 Hz), 5.27-5.35 (2H, m), 6.20 (1H, s), 7.00 (2H, d, J=8.3 Hz), 7.23-7.37 (7H, m).

Reference Example 66

3-tert-butyl-1H-pyrazole-5-carbaldehyde

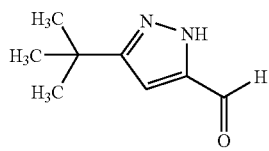

To a solution of ethyl 3-tert-butyl-1H-pyrazole-5-carboxylate (4.0 g, 20.4 mmol) in tetrahydrofuran (50 mL) was added lithium aluminum hydride (800 mg, 21.1 mmol) by small portions at 0° C., and the mixture was allowed to warm to room temperature and stirred for 1 hr. Sodium sulfate decahydrate (7.6 g) was added to the reaction mixture, and the mixture was stirred at room temperature for 30 min. The insoluble material was filtered off. The filtrate was concentrated and the residue was dissolved in tetrahydrofuran (100 mL). Manganese dioxide (10.0 g) was added, and the mixture was stirred at room temperature for 3 hr. The insoluble material was filtered off, and the filtrate was concentrated to give the title compound (2.13 g, yield 69%) as colorless crystals. $^1$H NMR (CDCl$_3$) δ: 1.37 (9H, s), 6.65 (1H, s), 9.95 (1H, s).

Reference Example 67

3-tert-butyl-5-(2-phenylethyl)-1H-pyrazole

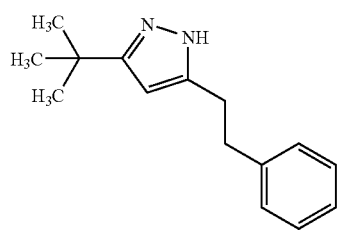

A mixture of 3-tert-butyl-1H-pyrazole-5-carbaldehyde (1.52 g, 10.0 mmol), benzyltriphenylphosphonium bromide (6.50 g, 15.0 mmol), potassium carbonate (2.76 g, 20.0 mmol) and N,N-dimethylformamide (30 mL) was stirred at room temperature for 14 hr. The reaction mixture was poured into 1 N hydrochloric acid, and the mixture was extracted with ethyl acetate. The organic layer was concentrated and the residue was purified by silica gel column chromatography (5%-80% ethyl acetate/hexane) to give pale-yellow crystals. The obtained crystals were dissolved in a mixed solvent of ethanol (50 mL) and tetrahydrofuran (50 mL), and 10% palladium-carbon (50% water-containing product, 2.0 g) was added. The mixture was stirred under an atmospheric hydrogen atmosphere for 3 hr. The insoluble material was filtered off, and the filtrate was concentrated to give the title compound (1.90 g, yield 83%) as colorless crystals. $^1$H NMR (CDCl$_3$) δ: 1.31 (9H, s), 2.90-2.99 (4H, m), 5.89 (1H, s), 7.18-7.33 (5H, m).

Reference Example 68 ethyl 3-(4-fluorophenyl)-1H-pyrazole-5-carboxylate

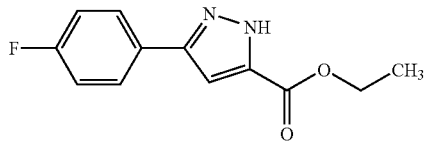

A mixture of ethyl 3-(4-fluorobenzoyl)pyruvate (11.3 g, 47.4 mmol), hydrazine monohydrate (2.50 g, 50.0 mmol) and ethanol (50 mL) was heated under reflux for 1 hr. The reaction mixture was cooled and poured into water. The precipitated solid was collected by filtration, washed with water, and dried to give the title compound (11.0 g, quantitative) as colorless crystals. $^1$H NMR (CDCl$_3$) δ: 1.41 (3H, t, J=7.2 Hz), 4.41 (2H, q, J=7.2 Hz), 7.05-7.18 (3H, m), 7.76 (2H, dd, J=8.2, 5.4 Hz), 11.21 (1H, s).

Reference Example 69

3-(4-fluorophenyl)-5-(2-phenylethyl)-1H-pyrazole

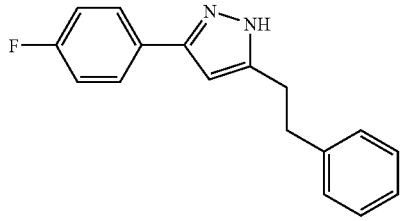

In the same manner as in Reference Example 66 and Reference Example 67, the title compound was obtained as colorless crystals from ethyl 3-(4-fluorophenyl)-1H-pyrazole-5-carboxylate. yield 40%, $^1$H NMR (CDCl$_3$) δ: 2.99 (4H, s), 6.31 (1H, s), 7.01-7.12 (2H, m), 7.15-7.36 (5H, m), 7.63-7.74 (2H, m).

Example 1 methyl 3-(4-{[3-(1,3,5-trimethyl-1H-pyrazol-4-yl)benzyl]oxy}phenyl)propanoate

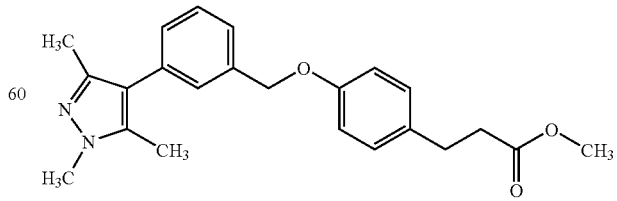

A solution of methyl 3-(4-hydroxyphenyl)propanoate (0.541 g, 3.00 mmol), [3-(1,3,5-trimethyl-1H-pyrazol-4-yl)

phenyl]methanol (0.433 g, 2.00 mmol) and tributylphosphine (0.747 mL, 3.00 mmol) in toluene (30 mL) was stirred under ice-cooling, and 1,1'-(azodicarbonyl)dipiperidine (0.757 g, 3.00 mmol) was added by small portions. The mixture was allowed to warm to room temperature and the mixture was stirred for 22 hr. Hexane (15 mL) was added to the reaction mixture. The precipitated insoluble material was filtered off, and the filtrate was concentrated under reduced pressure. The residue was purified by silica gel column chromatography (30%-70% ethyl acetate/hexane) to give the title compound (0.406 g, yield 54%) as a pale-yellow oil.

MS: m/z 379 (MH⁺).

Example 2

3-(4-{[3-(1,3,5-trimethyl-1H-pyrazol-4-yl)benzyl]oxy}phenyl)propanoic acid

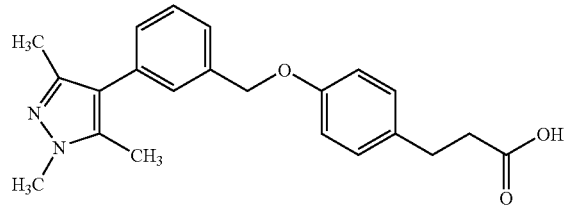

To a mixed solution of methyl 3-(4-{[3-(1,3,5-trimethyl-1H-pyrazol-4-yl)benzyl]oxy}phenyl)propanoate (0.406 g, 1.07 mmol) in methanol (5 mL) and tetrahydrofuran (5 mL) was added 2 M aqueous sodium hydroxide solution (1.5 mL), and the mixture was stirred at room temperature for 20 hr. Water was added to the reaction mixture, and the mixture was neutralized with 10% aqueous citric acid solution and extracted with ethyl acetate. The extract washed with saturated brine, dried over anhydrous sodium sulfate, and concentrated under reduced pressure. The residue was recrystallized from ethyl acetate-hexane to give the title compound (0.391 g, quantitative) as colorless needle crystals. MS: m/z 365 (MH⁺).

Example 3 methyl 3-(4-{[3-(2,4,5-trimethyl-3-thienyl)benzyl]oxy}phenyl)propanoate

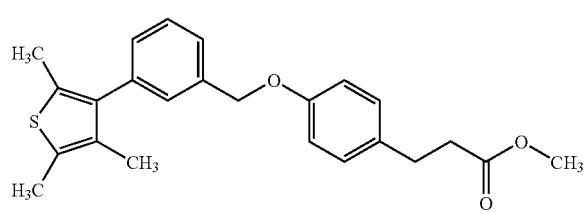

In the same manner as in Example 1, the title compound was obtained as a colorless oil from methyl 3-(4-hydroxyphenyl)propanoate and [3-(2,4,5-trimethyl-3-thienyl)phenyl]methanol. yield 80%, MS: m/z 395 (MH⁺).

Example 4

3-(4-([3-(2,4,5-trimethyl-3-thienyl)benzyl]oxy}phenyl)propanoic acid

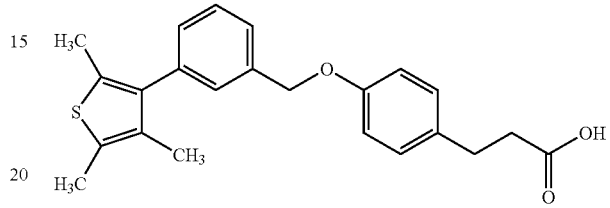

In the same manner as in Example 2, the title compound was obtained as colorless needle crystals from methyl 3-(4-{[3-(2,4,5-trimethyl-3-thienyl)benzyl]oxy}phenyl)propanoate. yield 72%, MS: m/z 381 (MH⁺).

Example 5 methyl 3-(4-{[3-(1-benzothiophen-3-yl)benzyl]oxy}phenyl)propanoate

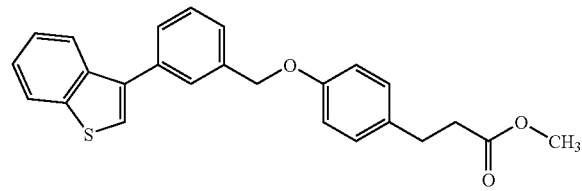

To a solution of [3-(1-benzothiophen-3-yl)phenyl]methanol (0.70 g, 2.91 mmol), methyl 3-(4-hydroxyphenyl)propanoate (0.58 g, 3.22 mmol) and tributylphosphine (0.95 mL, 3.81 mmol) in anhydrous tetrahydrofuran (40 mL) was added 1,1'-(azodicarbonyl)dipiperidine (0.96 g, 3.80 mmol) by small portions, and the mixture was stirred at room temperature for 18 hr. The reaction solution was diluted with diethyl ether (40 mL). The precipitate was filtered off, and the filtrate was concentrated under reduced pressure. The obtained residue was subjected to silica gel column chromatography (ethyl acetate:hexane=1:5) to give the title compound (1.0 g, yield 85%) as a colorless oil. MS: m/z 403 (MH⁺).

Example 6

3-(4-{[3-(1-benzothiophen-3-yl)benzyl]oxy}phenyl)propanoic acid

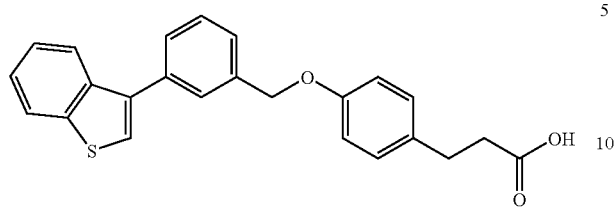

Methyl 3-(4-{[3-(1-benzothiophen-3-yl)benzyl]oxy}phenyl)propanoate (0.80 g, 1.99 mmol) was dissolved in a mixed solvent of tetrahydrofuran (10 mL) and ethanol (10 mL). An aqueous solution (5 mL) of 85% potassium hydroxide (0.28 g, 4.24 mmol) was added to the solution, and the mixture was stirred at room temperature for 18 hr. The reaction solution was diluted with ethyl acetate, and the mixture washed successively with aqueous citric acid solution, water and aqueous sodium chloride solution, dried over anhydrous magnesium sulfate, and concentrated under reduced pressure. The obtained crystals were washed with diethyl ether-hexane to give the title compound (0.70 g, yield 91%) as colorless prism crystals. MS: m/z 371 (M–OH), $^1$H NMR (CDCl$_3$) δ: 2.65 (2H, t, J=7.4 Hz), 2.92 (2H, t, J=7.4 Hz), 5.13 (2H, s), 6.93 (2H, d, J=8.8 Hz), 7.14 (2H, d, J=8.8 Hz), 7.34-7.98 (9H, m).

Example 7 methyl 3-(4-{[3-(1-benzothiophene-5-yl)benzyl]oxy}phenyl)propanoate

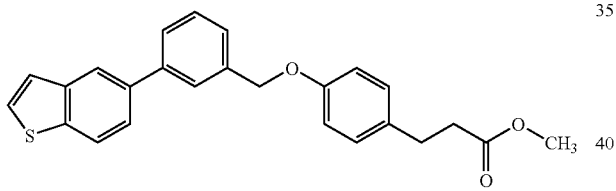

In the same manner as in Example 5, the title compound was obtained as colorless prism crystals from [3-(benzothiophene-5-yl)phenyl]methanol and methyl 3-(4-hydroxyphenyl)propanoate. yield 82%, MS: m/z 403 (MH$^+$).

Example 8

3-(4-{[3-(1-benzothiophene-5-yl)benzyl]oxy}phenyl)propanoic acid

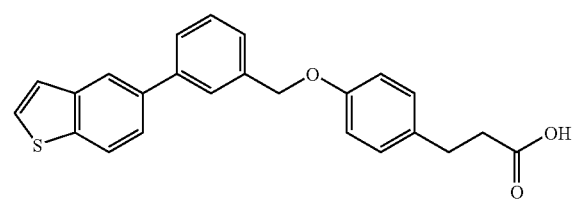

In the same manner as in Example 6, the title compound was obtained as colorless prism crystals from methyl 3-(4-{[3-(1-benzothiophene-5-yl)benzyl]oxy}phenyl)propanoate. yield 94%, $^1$H NMR (CDCl$_3$) δ: 2.65 (2H, t, J=7.4 Hz), 2.92 (2H, t, J=7.4 Hz), 5.12 (2H, s), 6.94 (2H, d, J=8.4 Hz), 7.14 (2H, d, J=8.4 Hz), 7.37-7.68 (6H, m), 7.72 (1H, s), 7.94 (1H, d, J=8.4 Hz), 8.03 (1H, d, J=1.6 Hz).

Example 9 methyl 3-(4-{[2-(1-benzothiophen-3-yl)benzyl]oxy]phenyl)propanoate

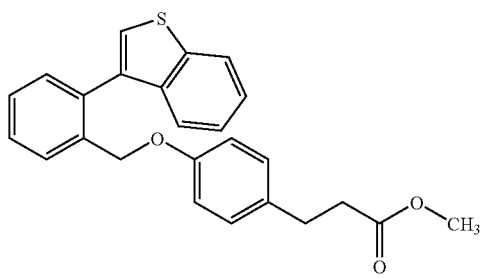

In the same manner as in Example 5, the title compound was obtained as a pale-yellow oil from [2-(1-benzothiophen-3-yl)phenyl]methanol and methyl 3-(4-hydroxyphenyl)propanoate. yield 93%, MS: m/z 403 (MH$^+$).

Example 10

3-(4-{[2-(1-benzothiophen-3-yl)benzyl]oxy}phenyl)propanoic acid

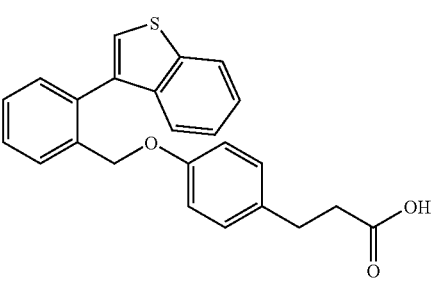

In the same manner as in Example 6, the title compound was obtained as colorless prism crystals from methyl 3-(4-{[2-(1-benzothiophen-3-yl)benzyl]oxy}phenyl)propanoate. yield 81%, $^1$H NMR (CDCl$_3$) δ: 2.61 (2H, t, J=7.6 Hz), 2.86 (2H, t, J=7.6 Hz), 4.85 (2H, s), 6.72 (2H, d, J=8.8 Hz), 7.03 (2H, d, J=8.8 Hz), 7.30-7.94 (9H, m).

Example 11 methyl 3-(4-([3-(1-tert-butoxycarbonyl-1H-indol-5-yl)benzyl]oxy}phenyl)propanoate

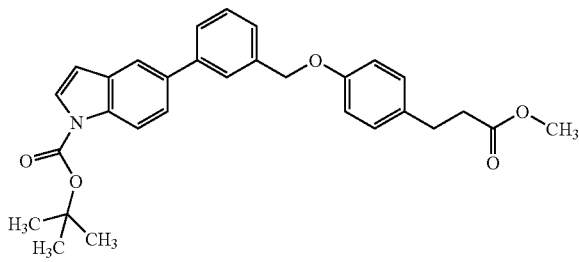

In the same manner as in Example 5, the title compound was obtained as a colorless oil from tert-butyl 5-(3-hydroxymethylphenyl)-1H-indole-1-carboxylate and methyl 3-(4-hydroxyphenyl)propanoate. yield 90%, $^1$H NMR (CDCl$_3$) δ: 1.69 (9H, s), 2.60 (2H, t, J=7.5 Hz), 2.90 (2H, t, J=7.5 Hz), 3.66 (3H, s), 5.10 (2H, s), 6.61 (1H, d, J=3.6 Hz), 6.93 (2H, d, J=8.7 Hz), 7.11 (2H, d, J=8.7 Hz), 7.35-7.62 (5H, m), 7.69 (1H, s), 7.76 (1H, d, J=1.2 Hz), 8.17 (1H, br d, J=8.4 Hz).

Examples 12 and 13

3-(4-([3-(1H-indol-5-yl)benzyl]oxy}phenyl)propanoic acid and 3-(4-{[3-(1-tert-butoxycarbonyl-1H-indol-5-yl)benzyl]oxy}phenyl)propanoic acid

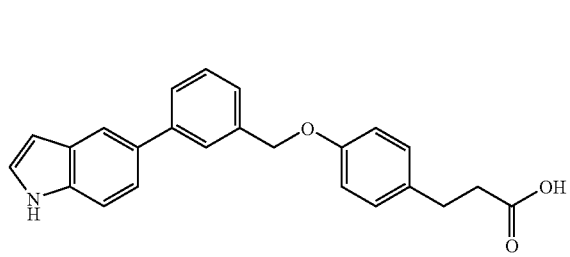

Methyl 3-(4-{[3-(1-tert-butoxycarbonyl-1H-indol-5-yl)benzyl]oxy}phenyl)propanoate (3.8 g, 7.83 mmol) was dissolved in a mixed solvent of tetrahydrofuran (30 mL) and methanol (30 mL), and the mixture was ice-cooled. An aqueous solution (10 mL) of 85% potassium hydroxide (1.0 g, 15.1 mmol) was added to the solution, and the mixture was stirred at room temperature for 18 hr. The reaction solution was diluted with ethyl acetate, and the mixture washed successively with aqueous citric acid solution, water and aqueous sodium chloride solution, dried over anhydrous magnesium sulfate, and concentrated under reduced pressure. The obtained oil was crystallized from diethyl ether-hexane to give 3-(4-{[3-(1H-indol-5-yl)benzyl]oxy}phenyl)propanoic acid (2.2 g, yield 76%) as colorless needle crystals. MS: m/z 372 (MH$^+$).

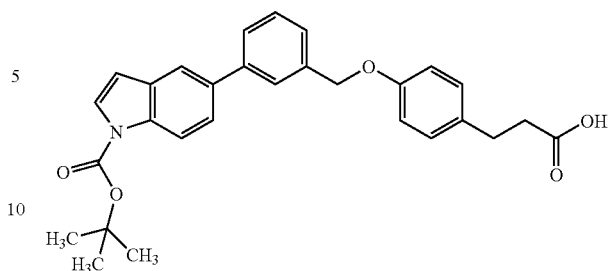

The residual filtrate was concentrated under reduced pressure and the residue was subjected to silica gel column chromatography (ethyl acetate:hexane=1:5-1:3-1:2) and crystallized from diethyl ether-hexane to give 3-(4-{[3-(1-tert-butoxycarbonyl-1H-indol-5-yl)benzyl]oxy}phenyl)propanoic acid (74 mg, yield 2%) as colorless prism crystals. $^1$H NMR (CDCl$_3$) δ: 1.69 (9H, s), 2.65 (2H, t, J=7.6 Hz), 2.91 (2H, t, J=7.6 Hz), 5.11 (2H, s), 6.61 (1H, d, J=3.6 Hz), 6.94 (2H, d, J=8.8 Hz), 7.14 (2H, d, J=8.8 Hz), 7.35-7.80 (7H, m), 8.18 (1H, d, J=8.4 Hz).

Example 14 methyl 3-(4-{[3-(1H-indol-5-yl)benzyl]oxy}phenyl)propanoate

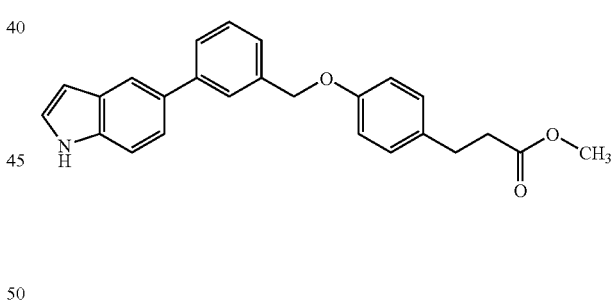

To a solution of 3-(4-{[3-(1H-indol-5-yl)benzyl]oxy}phenyl)propanoic acid (1.0 g, 2.69 mmol) in tetrahydrofuran (30 mL) was added a 2 mol/L trimethylsilyldiazomethane diethyl ether solution (1.5 mL, 3.0 mmol), and the mixture was stirred at room temperature for 18 hr. The reaction solution was diluted with ethyl acetate, and the mixture washed successively with aqueous citric acid solution, water and aqueous sodium chloride solution, dried over anhydrous magnesium sulfate, and concentrated under reduced pressure. The residue was subjected to silica gel column chromatography (ethyl acetate:hexane=1:5-1:3-1:2) to give the title compound (0.90 g, yield 86%) as a pale-yellow oil.

MS: m/z 386 (MH$^+$).

Example 15 methyl 3-(4-{[3-(1-methyl-1H-indol-5-yl)benzyl]oxy}phenyl)propanoate

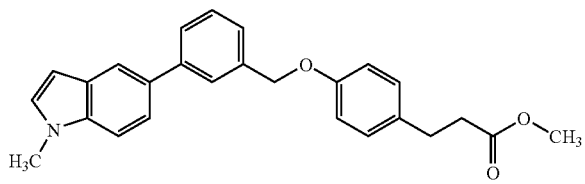

A solution of methyl 3-(4-{[3-(1H-indol-5-yl)benzyl]oxy]phenyl)propanoate (0.40 g, 1.04 mmol), iodomethane (0.18 mL, 2.89 mmol) and potassium carbonate (0.50 g, 3.62 mmol) in N,N-dimethylformamide (20 mL) was stirred at room temperature for 4 days. The reaction solution was diluted with ethyl acetate, and the mixture washed successively with aqueous citric acid solution, water and aqueous sodium chloride solution, dried over anhydrous magnesium sulfate, and concentrated under reduced pressure. The residue was subjected to silica gel column chromatography (ethyl acetate:hexane=1:5-1:3-1:2) to give the title compound (0.23 g, yield 56%) as colorless prism crystals. MS: m/z 400 (MH$^+$).

Example 16

3-(4-{[3-(1-methyl-1H-indol-5-yl)benzyl]oxy}phenyl)propanoic acid

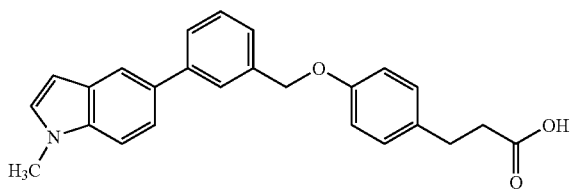

In the same manner as in Example 6, the title compound was obtained as pale-green prism crystals from methyl 3-(4-{[3-(1-methyl-1H-indol-5-yl)benzyl]oxy}phenyl)propanoate. yield 88%, MS: m/z 386 (MH$^+$).

Example 17 methyl 3-(4-([3-(5-chloro-3-methyl-1-benzothiophen-2-yl)benzyl]oxy)phenyl)propanoate

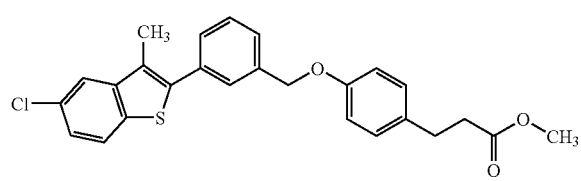

In the same manner as in Example 5, the title compound was obtained as colorless prism crystals from [3-(5-chloro-3-methyl-1-benzothiophen-2-yl)phenyl]methanol and methyl 3-(4-hydroxyphenyl)propanoate. yield 100%, MS: m/z 451 (MH$^+$).

Example 18

3-(4-{[3-(5-chloro-3-methyl-1-benzothiophen-2-yl)benzyl]oxy]phenyl)propanoic acid

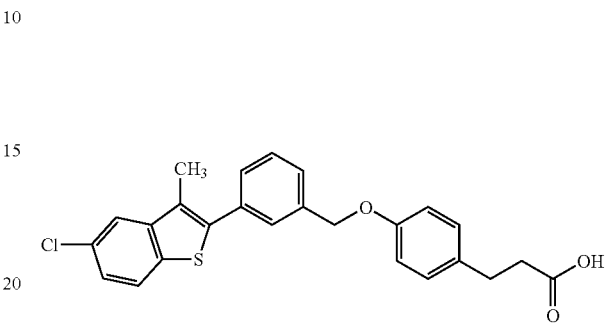

In the same manner as in Example 6, the title compound was obtained as colorless prism crystals from methyl 3-(4-{[3-(5-chloro-3-methyl-1-benzothiophen-2-yl)benzyl]oxy}phenyl)propanoate. yield 94%, $^1$H NMR (CDCl$_3$) δ: 2.40 (3H, s), 2.66 (2H, t, J=7.6 Hz), 2.92 (2H, t, J=7.6 Hz), 5.11 (2H, s), 6.93 (2H, d, J=8.6 Hz), 7.14 (2H, d, J=8.6 Hz), 7.31 (1H, dd, J=1.8, 8.4 Hz), 7.43-7.60 (4H, m), 7.69 (1H, d, J=1.8 Hz), 7.73 (1H, d, J=8.4 Hz).

Example 19 methyl 3-(4-{[3-(1-benzyl-1H-indol-5-yl)benzyl]oxy)phenyl)propanoate

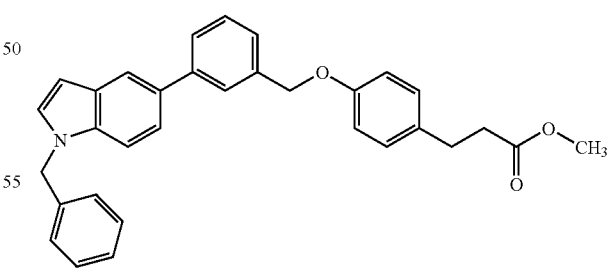

In the same manner as in Example 15, the title compound was obtained as a colorless oil from methyl 3-(4-{[3-(1H-indol-5-yl)benzyl]oxy}phenyl)propanoate. yield 22%, MS: m/z 476 (MH$^+$).

Example 20

3-(4-([3-(1-benzyl-1H-indol-5-yl)benzyl]oxy}phenyl)propanoic acid

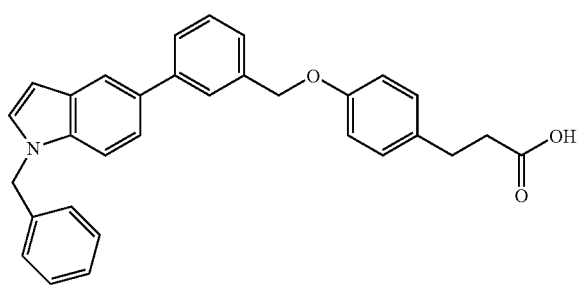

In the same manner as in Example 6, the title compound was obtained as a pale-yellow oil from methyl 3-(4-{[3-(1-benzyl-1H-indol-5-yl)benzyl]oxy}phenyl)propanoate. yield 78%, MS: m/z 462 (MH$^+$).

Examples 21 and 22 methyl 3-(4-{[3-(1-propyl-1H-indol-5-yl)benzyl]oxy}phenyl)propanoate and 3-(4-([3-(1-propyl-1H-indol-5-yl)benzyl]oxy}phenyl)propanoic acid A mixed solution of methyl 3-(4-{[3-(1H-indol-5-yl)benzyl]oxy}phenyl)propanoate (0.65 g, 1.69 mmol) and sodium hydride (60% in oil, 80 mg, 2.0 mmol) in tetrahydrofuran (18 mL) and N,N-dimethylformamide (3 mL) was stirred under ice-cooling for 20 min. 1-Iodopropane (0.25 mL, 2.56 mmol) was added to the solution, and the mixture was stirred at room temperature for 2 days. Aqueous citric acid solution was added to the reaction solution, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate: hexane=1:5-1:2-1:1) to give the title compound.

methyl 3-(4-{[3-(1-propyl-1H-indol-5-yl)benzyl]oxy}phenyl)propanoate (0.41 g, yield 57%), colorless oil, MS: m/z 428 (MH$^+$).

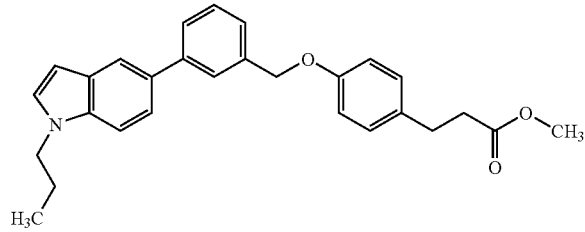

3-(4-{[3-(1-propyl-1H-indol-5-yl)benzyl]oxy}phenyl)propanoic acid (0.19 g, yield 27%), colorless needle crystals, MS: m/z 414 (MH$^+$).

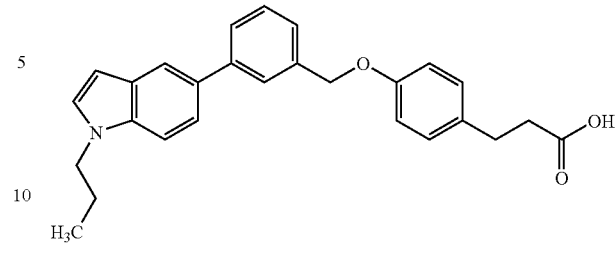

Example 23 methyl 3-(4-{[3-(2-methyl-1H-indol-1-yl)benzyl]oxy]phenyl)propanoate

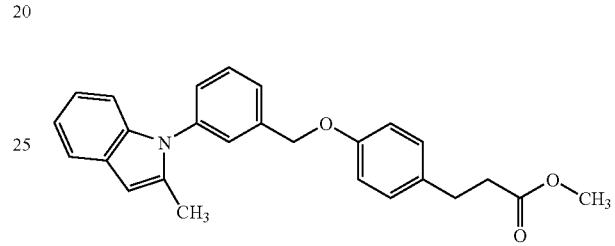

In the same manner as in Example 5, the title compound was obtained as a colorless oil from [3-(2-methyl-1H-indol-1-yl)phenyl]methanol and methyl 3-(4-hydroxyphenyl)propanoate. yield 67%, MS: m/z 400 (MH$^+$).

Example 24

3-(4-{[3-(2-methyl-1H-indol-1-yl)benzyl]oxy}phenyl)propanoic acid

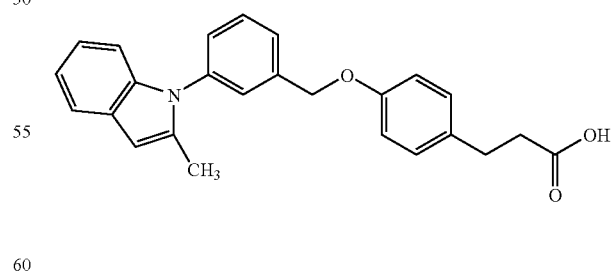

In the same manner as in Example 6, the title compound was obtained as a pale-yellow oil from methyl 3-(4-{[3-(2-methyl-1H-indol-1-yl)benzyl]oxy}phenyl)propanoate. yield 87%, MS: m/z 386 (MH$^+$).

Example 25 ethyl 3-[2,6-difluoro-4-({4-[(2-phenyl-1H-indol-1-yl)methyl]benzyl}oxy)phenyl]propanoate

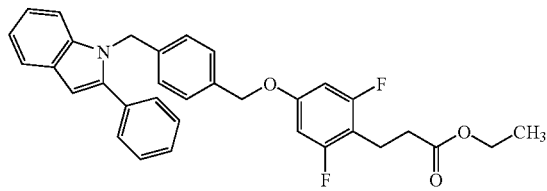

In the same manner as in Example 5, the title compound was obtained as a colorless oil from (4-[(2-phenyl-1H-indol-1-yl)methyl]phenyl}methanol and ethyl 3-(2,6-difluoro-4-hydroxyphenyl)propanoate. yield 70%, MS: m/z 526 (MH$^+$).

Example 26

3-[2,6-difluoro-4-({4-[(2-phenyl-1H-indol-1-yl)methyl]benzyl}oxy)phenyl]propanoic acid

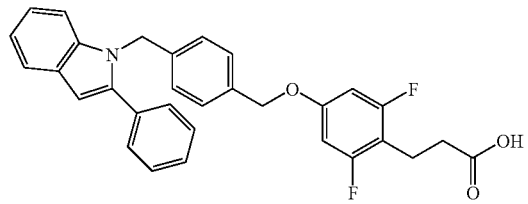

In the same manner as in Example 6, the title compound was obtained as colorless prism crystals from ethyl 3-[2,6-d]fluoro-4-([4-[(2-phenyl-1H-indol-1-yl)methyl]benzyl}oxy)phenyl]propanoate. yield 84%, MS: m/z 498 (MH$^+$).

Example 27

3-{4-[(3-(piperidin-1-yl)benzyl)oxy]phenyl}propanoic acid

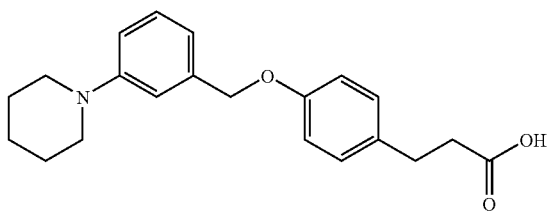

A mixture of methyl 3-{4-[(3-bromobenzyl)oxy]phenyl)propanoate (0.3 g, 0.86 mmol), piperidine (0.13 mL, 1.29 mmol), tris(dibenzylideneacetone)dipalladium(0) (31 mg, 34 µmol), rac-2,2'-bis(diphenylphosphino)-1,1'-binaphthyl (32 mg, 52 µmol), cesium carbonate (0.39 g, 1.2 mmol) and toluene (6.0 mL) was stirred under a nitrogen atmosphere at 80° C. for 22 hr. After cooling, the reaction mixture washed with water and saturated brine, dried over anhydrous magnesium sulfate, and concentrated under reduced pressure. The residue was purified by silica gel column chromatography (hexane/ethyl acetate=10/1-hexane/ethyl acetate=4/1) to give a yellow oil (124 mg). Then, a mixture of the obtained oil, 1 N sodium hydroxide aqueous solution (0.7 mL), methanol (2.0 mL) and tetrahydrofuran (4.0 mL) was stirred at room temperature for 2 hr. The reaction mixture was adjusted to pH 7 with 1 N hydrochloric acid, and concentrated under reduced pressure. The residue was purified by preparative HPLC (gradient cycle A), and the objective fractions were collected and concentrated. Water was added to the residue, and the mixture was adjusted to pH 7 with saturated aqueous sodium hydrogencarbonate and extracted with ethyl acetate. The organic layer was dried over anhydrous magnesium sulfate and concentrated under reduced pressure to give the title compound (32 mg, yield 27%) as an orange powder.

MS (APCI−): 338 (M−H).

Example 28

3-(4-{[3-(4-phenylpiperidin-1-yl)benzyl]oxy}phenyl)propanoic acid

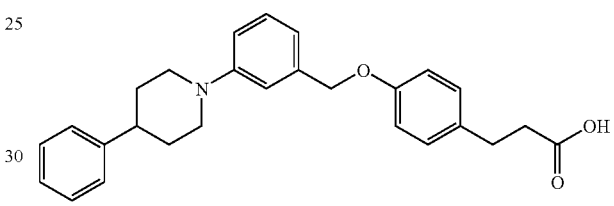

In the same manner as in Example 27, the title compound was obtained as a beige powder from methyl 3-{4-[(3-bromobenzyl)oxy]phenyl}propanoate and 4-phenylpiperidine. yield 52%, $^1$H NMR (CDCl$_3$) δ: 1.81-2.03 (4H, m), 2.58-2.72 (3H, m), 2.77-2.97 (4H, m), 3.83 (2H, d, J=12.6 Hz), 5.00 (2H, s), 6.87-6.98 (4H, m), 7.05 (1H, m), 7.12 (2H, d, J=8.7 Hz), 7.18-7.36 (6H, m).

Example 29

3-(4-{[3-(2-phenylmorpholin-4-yl)benzyl]oxy}phenyl)propanoic acid

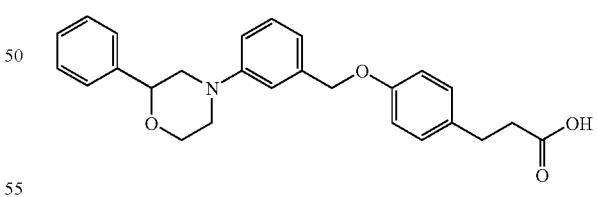

A mixture of methyl 3-{4-[(3-bromobenzyl)oxy]phenyl}propanoate (0.3 g, 0.86 mmol), 2-phenylmorpholine (0.21 g, 1.29 mmol), tris(dibenzylideneacetone)dipalladium (0) (31 mg, 34 µmol), rac-2,2'-bis(diphenylphosphino)-1,1'-binaphthyl (32 mg, 52 µmol), cesium carbonate (0.39 g, 1.2 mmol) and toluene (6.0 mL) was stirred under a nitrogen atmosphere at 80° C. for 16 hr. After cooling, the reaction mixture washed with water and saturated brine, dried over anhydrous magnesium sulfate, and concentrated under reduced pressure to give an oil. Then, to a mixture of the obtained oil, methanol (4.0 mL) and tetrahydrofuran (6.0 mL)

was added 1N aqueous sodium hydroxide solution (2.0 mL) with stirring at room temperature, and the mixture was stirred at the same temperature for 2 hr. The reaction mixture was adjusted to pH 7 with 1N hydrochloric acid and extracted with ethyl acetate. The organic layer was dried over anhydrous magnesium sulfate, and concentrated under reduced pressure. The residue was purified by silica gel column chromatography (hexane/ethyl acetate=2/1-hexane/ethyl acetate=1/2) to give the title compound (0.18 g, yield 36%) as a yellow oil.

MS (APCI−): 416 (M−H).

Example 30

3-[4-({3-[4-(2-methylphenoxy)piperidin-1-yl]benzyl}oxy)phenyl]propanoic acid

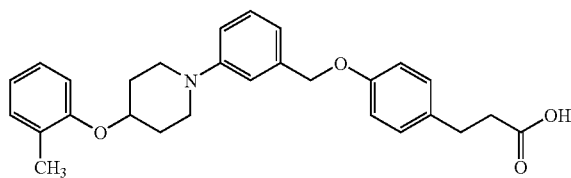

In the same manner as in Example 29, the title compound was obtained as a yellow oil from methyl 3-{4-[(3-bromobenzyl)oxy]phenyl}propanoate and 4-(2-methylphenoxy)piperidine. yield 38%, MS (APCI−): 444 (M−H).

Example 31

3-(4-{[3-(3-phenylpyrrolidin-1-yl)benzyl]oxy}phenyl)propanoic acid

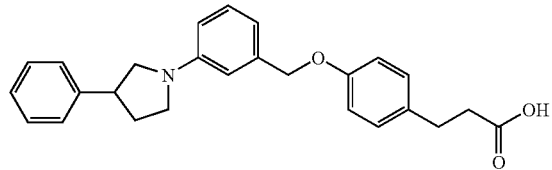

In the same manner as in Example 29, the title compound was obtained as beige crystals from methyl 3-{4-[(3-bromobenzyl)oxy]phenyl}propanoate and 3-phenylpyrrolidine. yield 52%, MS (APCI−): 400 (M−H).

Example 32

3-[4-({3-[4-(2-methylphenyl)piperidin-1-yl]benzyl}oxy)phenyl]propanoic acid

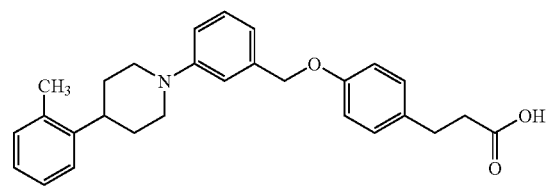

In the same manner as in Example 29, the title compound was obtained as a brown oil from methyl 3-{4-[(3-bromobenzyl)oxy]phenyl}propanoate and 4-(2-methylphenyl)piperidine. yield 28%, MS (APCI−): 428 (M−H).

Example 33

3-[4-([4-[4-(2-methylphenoxy)piperidin-1-yl]benzyl}oxy)phenyl]propanoic acid

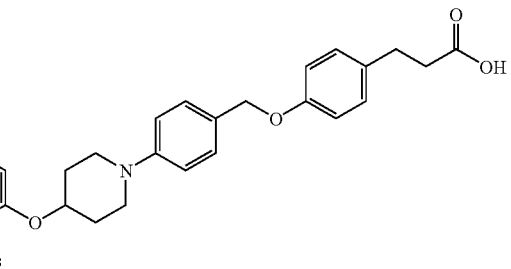

In the same manner as in Example 29, the title compound was obtained as colorless crystals from methyl 3-{4-[(4-bromobenzyl)oxy]phenyl}propanoate and 4-(2-methylphenoxy)piperidine. yield 16%, MS (APCI−): 444 (M−H).

Example 34

3-(4-([3-(3,4-dihydroquinolin-1 (2H)-yl)benzyl]oxy)phenyl)propanoic acid

A mixture of methyl 3-{4-[(3-bromobenzyl)oxy]phenyl}propanoate (0.3 g, 0.86 mmol), 1,2,3,4-tetrahydroquinoline (0.17 mL, 1.29 mmol), tris(dibenzylideneacetone)dipalladium(0) (31 mg, 34 μmol), rac-2,2'-bis(diphenylphosphino)-1,1'-binaphthyl (32 mg, 52 μmol), cesium carbonate (0.39 g, 1.2 mmol) and toluene (6.0 mL) was stirred under a nitrogen atmosphere at 90° C. for 16 hr. After cooling, the reaction mixture washed with water and saturated brine, dried over anhydrous magnesium sulfate, and concentrated under reduced pressure to give an oil. Then, a mixture of the obtained oil, 1N aqueous sodium hydroxide solution (1.7 mL), methanol (2.0 mL) and tetrahydrofuran (4.0 mL) was stirred at room temperature for 2 hr. The reaction mixture was concentrated, and the residue as partitioned between ethyl acetate and 1N hydrochloric acid. The organic layer was dried and concentrated under reduced pressure. The residue was purified by preparative HPLC (gradient cycle A), and the object fractions were collected and concentrated. Water was added to the residue, and the mixture was adjusted to pH 7 with saturated aqueous sodium hydrogencarbonate and extracted with ethyl acetate. The organic layer was dried over anhydrous magnesium sulfate and concentrated under

Example 35

3-(4-{[3-(3,4-dihydroisoquinolin-2(1H)-yl)benzyl]oxy}phenyl)propanoic acid

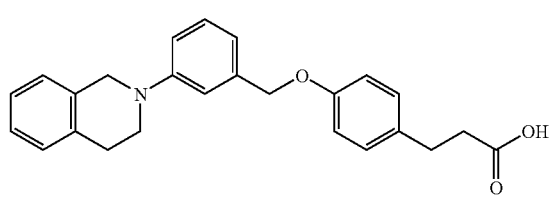

In the same manner as in Example 34, the title compound was obtained as a brown powder from methyl 3-{4-[(3-bromobenzyl)oxy]phenyl]propanoate and 1,2,3,4-tetrahydroisoquinoline. yield 10%, MS (APCI–): 386 (M–H).

Example 36

3-(4-{[3-(2,3-dihydro-1H-indol-1-yl)benzyl]oxy}phenyl)propanoic acid

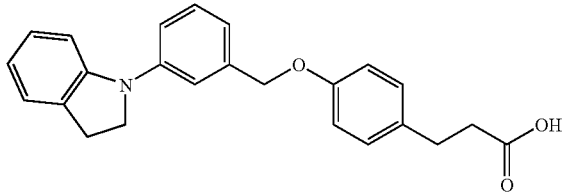

In the same manner as in Example 34, the title compound was obtained as a green powder from methyl 3-{4-[(3-bromobenzyl)oxy]phenyl}propanoate and indoline. yield 13%, MS (APCI–):372 (M–H).

Example 37

3-(4-{[3-(2-methyl-2,3-dihydro-1H-indol-1-yl)benzyl]oxy}phenyl)propanoic acid

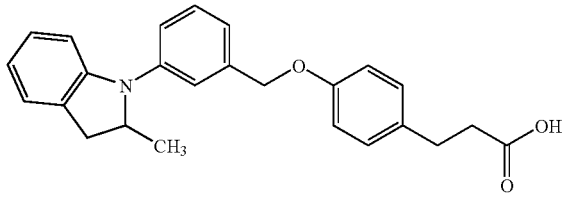

In the same manner as in Example 34, the title compound was obtained as a green oil from methyl 3-{4-[(3-bromobenzyl)oxy]phenyl}propanoate and 2-methylindoline. yield 10%, MS (APCI–): 386 (M–H).

Example 38

3-(4-{[3-(6-methyl-3,4-dihydroquinolin-1(2H)-yl)benzyl]oxy)phenyl)propanoic acid

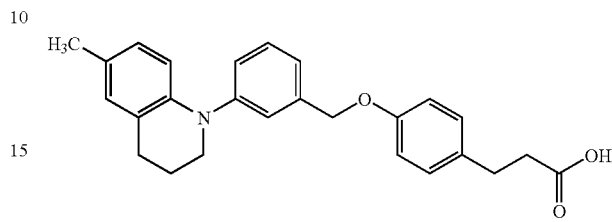

In the same manner as in Example 34, the title compound was obtained as a beige powder from methyl 3-(4-[(3-bromobenzyl)oxy]phenyl}propanoate and 6-methyl-1,2,3,4-tetrahydroquinoline. yield 15%, MS (APCI–): 400 (M–H).

Example 39

3-(4-([3-(5-methyl-2,3-dihydro-1H-indol-1-yl)benzyl]oxy}phenyl)propanoic acid

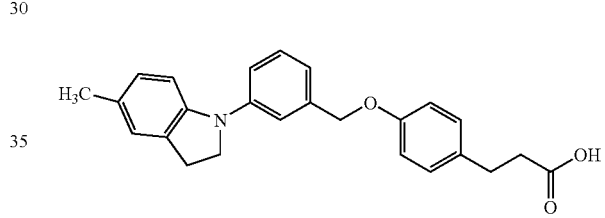

In the same manner as in Example 34, the title compound was obtained as a beige powder from methyl 3-{4-[(3-bromobenzyl)oxy]phenyl)propanoate and 5-methylindoline. yield 29%, MS (APCI–): 386 (M–H).

Example 40

3-(4-{[3-(2-methyl-3,4-dihydroquinolin-1(2H)-yl)benzyl]oxy}phenyl)propanoic acid

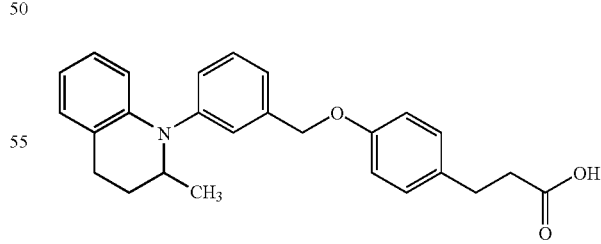

In the same manner as in Example 34, the title compound was obtained as a beige powder from methyl 3-{4-[(3-bromobenzyl)oxy]phenyl}propanoate and 2-methyl-1,2,3,4-tetrahydroquinoline. yield 13%, MS (APCI–): 400 (M–H), $^1$H NMR (CDCl$_3$) δ: 1.16 (3H, d, J=6.6 Hz), 1.84 (1H, m), 2.06 (1H, m), 2.65 (2H, t, J=7.8 Hz), 2.74-2.98 (4H, m), 3.91 (1H, m), 5.01 (2H, s), 6.54 (1H, dd, J=8.1, 0.6 Hz), 6.67 (1H, m), 6.84-6.93 (3H, m), 7.04 (1H, d, J=6.6 Hz), 7.09-7.23 (4H, m), 7.28 (1H, s), 7.36 (1H, t, J=7.8 Hz).

Example 41

3-(4-[(4-{[5-(benzyloxy)-1H-indol-1-yl]methyl}benzyl)oxy]phenyl}propanoic acid

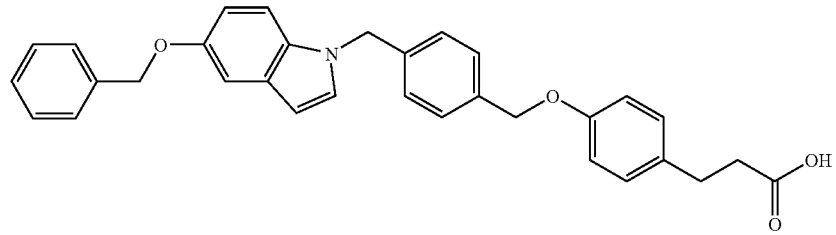

To a solution of 5-(benzyloxy)-1H-indole (0.19 g, 0.86 mmol) in N,N-dimethylformamide (10 mL) was added sodium hydride (60% in oil, 35 mg, 0.86 mmol) with stirring at 0° C., and the mixture was stirred at the same temperature for 10 min. Methyl 3-(4-{[4-(chloromethyl)benzyl]oxy}phenyl)propanoate (0.25 g, 0.78 mmol) was added to the obtained mixture and the mixture was stirred at room temperature for 12 hr. The reaction mixture was diluted with ethyl acetate, and the mixture washed with 5% aqueous potassium hydrogensulfate solution and saturated brine, dried over anhydrous magnesium sulfate, and concentrated under reduced pressure. The residue was purified by silica gel column chromatography (hexane/ethyl acetate=10/1-hexane/ethyl acetate=3/1) to give an oil. Then, a mixture of the obtained oil, 1 N aqueous sodium hydroxide solution (1.6 mL), methanol (3.0 mL) and tetrahydrofuran (6.0 mL) was stirred at room temperature for 2 hr. The reaction mixture was diluted with ethyl acetate, and the mixture was washed with 5% aqueous potassium hydrogensulfate solution, water and saturated brine, dried over anhydrous magnesium sulfate, and concentrated under reduced pressure. The residue was purified by silica gel column chromatography (hexane/ethyl acetate=10/1-hexane/ethyl acetate=1/2) to give the title compound (200 mg, yield 49%) as beige crystals. MS (APCI−): 490 (M−H).

Example 42

3-{4-[(4-{[4-(2,6-diisopropylphenoxy)piperidin-1-yl]methyl}benzyl)oxy]phenyl}propanoic acid

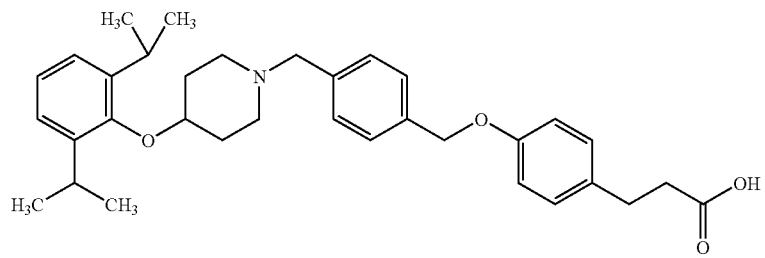

To a mixture of methyl 3-[4-({4-[(4-hydroxypiperidin-1-yl)methyl]benzyl}oxy)phenyl]propanoate (0.20 g, 0.52 mmol), 2,6-diisopropylphenol (0.15 mL, 0.78 mmol), tributylphosphine (0.20 mL, 0.78 mmol) and tetrahydrofuran (6.0 mL) was added 1,1'-(azodicarbonyl)dipiperidine (0.20 g, 0.78 mmol) with stirring at 0° C., and the mixture was stirred at room temperature for 16 hr. Diethyl ether was added to the reaction mixture, the insoluble material was filtered off, and the filtrate was concentrated under reduced pressure to give an oil. Then, a mixture of the obtained oil, 1 N aqueous sodium hydroxide solution (1.0 mL), methanol (3.0 mL) and tetrahydrofuran (6.0 mL) was stirred at room temperature for 2 hr. The reaction mixture was neutralized with 1 N hydrochloric acid, and diluted with ethyl acetate. The mixture washed with water and saturated brine, dried over anhydrous magnesium sulfate, and concentrated under reduced pressure. The residue was purified by silica gel column chromatography (hexane/ethyl acetate=2/1-hexane/ethyl acetate=1/2) to give the title compound (45 mg, yield 16%) as colorless crystals. MS (APCI−): 528 (M−H).

Example 43

3-{4-[(4-{[4-(1-naphthyloxy)piperidin-1-yl]methyl}benzyl)oxy]phenyl}propanoic acid

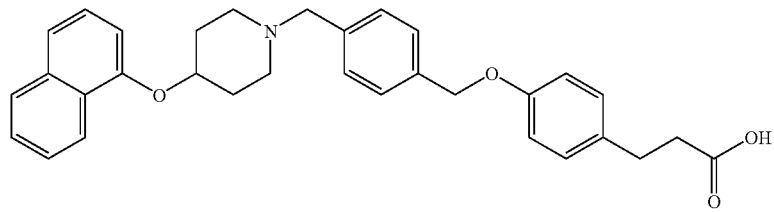

In the same manner as in Example 42, the title compound was obtained as colorless crystals from methyl 3-[4-({4-[(4-hydroxypiperidin-1-yl)methyl]benzyl}oxy)phenyl]propanoate and 1-naphthol. yield 9%, MS (APCI−): 494 (M−H).

Example 44 methyl 3-[4-({4-[(2-phenyl-1H-indol-1-yl)methyl]benzyl}oxy)phenyl]propanoate

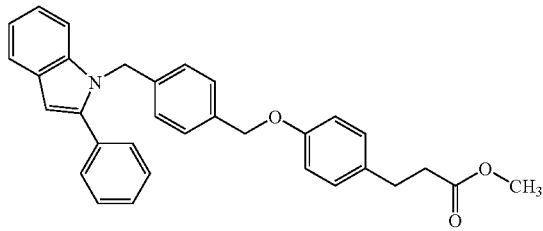

To a solution of 2-phenylindole (0.17 g, 0.86 mmol) in N,N-dimethylformamide (5 mL) was added sodium hydride (60% in oil, 35 mg, 0.86 mmol) with stirring at 0° C., and the mixture was stirred at the same temperature for 10 min. Methyl 3-(4-{[4-(chloromethyl)benzyl]oxy}phenyl)propanoate (0.25 g, 0.78 mmol) was added to the obtained mixture and the mixture was stirred at room temperature for 16 hr. The reaction mixture was diluted with ethyl acetate, and the mixture washed with 5% aqueous potassium hydrogensulfate solution and saturated brine, dried over anhydrous magnesium sulfate, and concentrated under reduced pressure. The residue was purified by silica gel column chromatography (hexane/ethyl acetate=10/1-hexane/ethyl acetate=3/1) to give the title compound (0.17 g, yield 46%) as a colorless oil. $^1$H NMR (CDCl$_3$) δ: 2.59 (2H, t, J=7.8 Hz), 2.89 (2H, t, J=7.8 Hz), 3.66 (3H, s), 4.98 (2H, s), 5.38 (2H, s), 6.66 (1H, s), 6.88 (2H, d, J=8.7 Hz), 7.00-7.20 (7H, m), 7.29-7.47 (7H, m), 7.67 (1H, m).

Example 45

3-[4-({4-[(2-phenyl-1H-indol-1-yl)methyl]benzyl}oxy)phenyl]propanoic acid

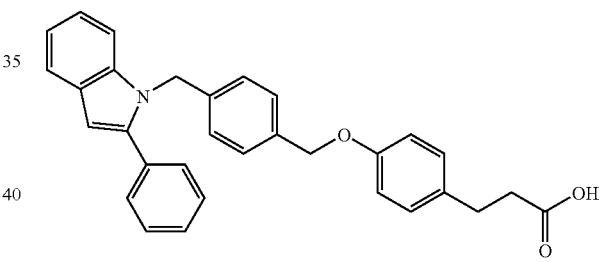

Methyl 3-[4-({4-[(2-phenyl-1H-indol-1-yl)methyl]benzyl}oxy)phenyl]propanoate (0.17 g, 0.36 mmol) was dissolved in a mixed solution of methanol (4 mL) and tetrahydrofuran (8 mL), and 1 N aqueous sodium hydroxide solution (0.71 mL) was added with stirring at room temperature. The mixture was stirred at the same temperature for 2 hr. After completion of the reaction, the reaction mixture was diluted with ethyl acetate, and the mixture washed successively with 5% aqueous potassium hydrogensulfate solution, water and saturated brine, dried over anhydrous magnesium sulfate, and concentrated under reduced pressure. The residue was crystallized from hexane/ethyl acetate=4/1 to give the title compound (0.15 g, yield 88%) as colorless crystals. MS (APCI−): 460 (M−H), $^1$H NMR (CDCl$_3$) δ: 2.63 (2H, t, J=7.8 Hz), 2.89 (2H, t, J=7.8 Hz), 4.97 (2H, s), 5.36 (2H, s), 6.65 (1H, s), 6.87 (2H, d, J=8.7 Hz), 7.03 (2H, d, J=8.1 Hz), 7.07-7.19 (5H, m), 7.28-7.47 (7H, m), 7.67 (1H, m).

Example 46

3-[2-fluoro-4-({4-[(2-phenyl-1H-indol-1-yl)methyl]benzyl}oxy)phenyl]propanoic acid

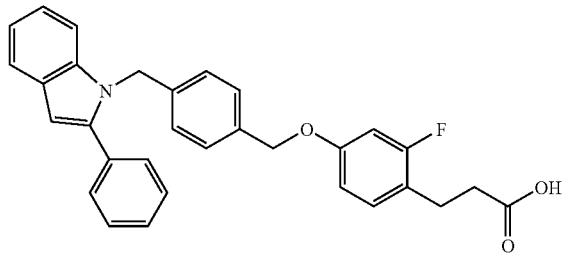

To a mixture of ethyl 3-(2-fluoro-4-hydroxyphenyl)propanoate (0.29 g, 1.34 mmol), {4-[(2-phenyl-1H-indol-1-yl)methyl]phenyl}methanol (0.38 g, 1.22 mmol), tributylphosphine (0.46 mL, 1.83 mmol) and tetrahydrofuran (7.6 mL) was added 1,1'-(azodicarbonyl)dipiperidine (0.46 g, 1.83 mmol) with stirring at 0° C., and the mixture was stirred at room temperature for 18 hr. Diethyl ether was added to the reaction mixture. The insoluble material was filtered off, and the filtrate was concentrated under reduced pressure. The residue was purified by silica gel column chromatography (hexane/ethyl acetate=10/1-hexane/ethyl acetate=2/1) to give a colorless oil. Then, a mixture of the obtained oil, 1 N aqueous sodium hydroxide solution (2.5 mL), methanol (5.0 mL) and tetrahydrofuran (10.0 mL) was stirred at room temperature for 14 hr. The reaction mixture was diluted with ethyl acetate, and the mixture washed with 1 N hydrochloric acid, water and saturated brine, dried over anhydrous magnesium sulfate, and concentrated under reduced pressure. The residue was purified by silica gel column chromatography (hexane/ethyl acetate=10/1-hexane/ethyl acetate=1/2) to give the title compound (0.46 g, yield 79%) as colorless crystals. MS (APCI−): 478 (M−H), $^1$H NMR (CDCl$_3$) δ: 2.64 (2H, t, J=7.8 Hz), 2.91 (2H, t, J=7.8 Hz), 4.96 (2H, s), 5.38 (2H, s), 6.61-6.70 (3H, m), 7.01-7.20 (6H, m), 7.32 (2H, d, J=8.1 Hz), 7.34-7.47 (5H, m), 7.67 (1H, m).

Example 47

3-[4-({4-[(2-methyl-1H-indol-1-yl)methyl]benzyl}oxy)phenyl]propanoic acid

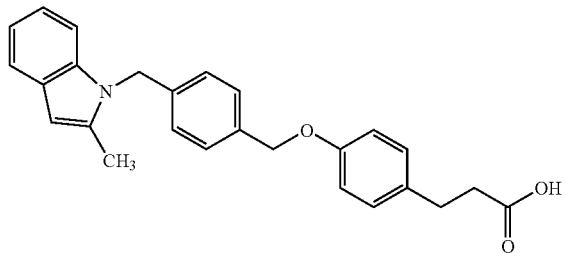

In the same manner as in Example 46, the title compound was obtained as pink crystals from methyl 3-(4-hydroxyphenyl)propanoate and {4-[(2-methyl-1H-indol-1-yl)methyl]phenyl}methanol. yield 87%, MS (APCI−): 398 (M−H).

Example 48

3-[2-fluoro-4-({4-[(2-methyl-1H-indol-1-yl)methyl]benzyl}oxy)phenyl]propanoic acid

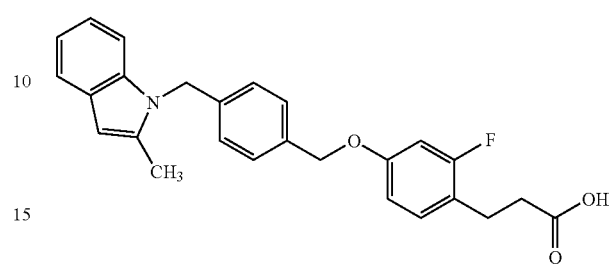

In the same manner as in Example 46, the title compound was obtained as colorless crystals from ethyl 3-(2-fluoro-4-hydroxyphenyl)propanoate and {4-[(2-methyl-1H-indol-1-yl)methyl]phenyl}methanol. yield 90%, MS (APCI−): 416 (M−H).

Example 49

3-[4-({4-[(5-methoxy-2-methyl-1H-indol-1-yl)methyl]benzyl}oxy)phenyl]propanoic acid

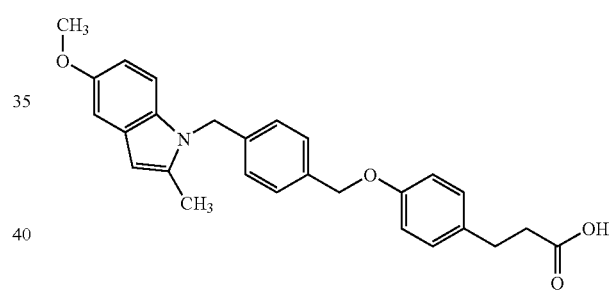

In the same manner as in Example 41, the title compound was obtained as beige crystals from methyl 3-(4-{[4-(chloromethyl)benzyl]oxy}phenyl)propanoate and 5-methoxy-2-methyl-1H-indole. yield 50%, MS (APCI−): 428 (M−H).

Example 50

3-[4-({4-[(7-methyl-1H-indol-1-yl)methyl]benzyl}oxy)phenyl]propanoic acid

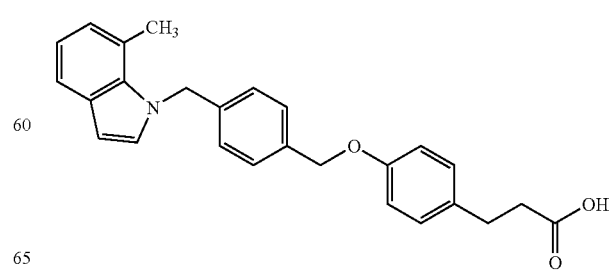

In the same manner as in Example 41, the title compound was obtained as colorless crystals from methyl 3-(4-{[4-(chloromethyl)benzyl]oxy}phenyl)propanoate and 7-methyl-1H-indole. yield 56%, MS (APCI−): 398 (M−H).

Example 51

3-[4-({4-[(5-chloro-1H-indol-1-yl)methyl]benzyl)oxy)phenyl]propanoic acid

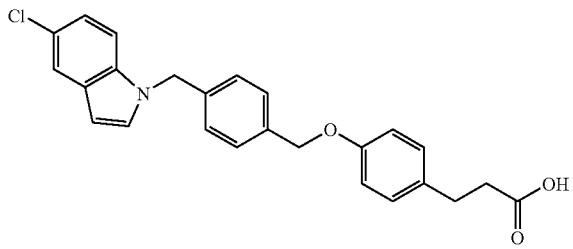

In the same manner as in Example 41, the title compound was obtained as colorless crystals from methyl 3-(4-{[4-(chloromethyl)benzyl]oxy}phenyl)propanoate and 5-chloro-1H-indole. yield 71%, MS (APCI−): 418 (M−H), 420.

Example 52

3-[4-({4-[(6-chloro-1H-indol-1-yl)methyl]benzyl}oxy)phenyl]propanoic acid

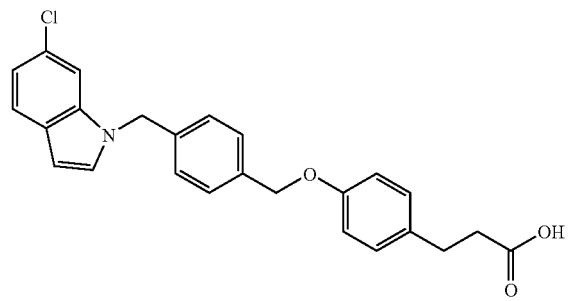

In the same manner as in Example 41, the title compound was obtained as colorless crystals from methyl 3-(4-{[4-(chloromethyl)benzyl]oxy}phenyl)propanoate and 6-chloro-1H-indole. yield 81%, MS (APCI−): 418 (M−H), 420.

Example 53

3-{4-[(4-({2-(cyanomethyl)-1H-indol-1-yl] methyl}benzyl)oxy]phenyl}propanoic acid

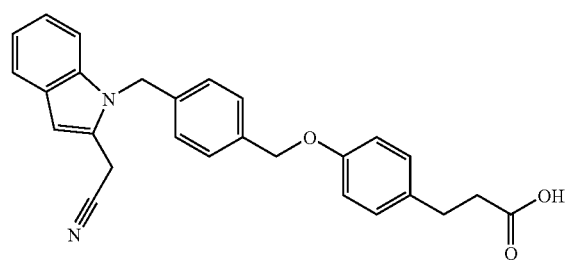

In the same manner as in Example 41, the title compound was obtained as yellow crystals from methyl 3-(4-{[4-(chloromethyl)benzyl]oxy}phenyl)propanoate and 1H-indol-2-ylacetonitrile. yield 8%, MS (APCI−): 423 (M−H).

Example 54

3-{4-[(4-{[3-(cyanomethyl)-1H-indol-1-yl] methyl}benzyl)oxy]phenyl}propanoic acid

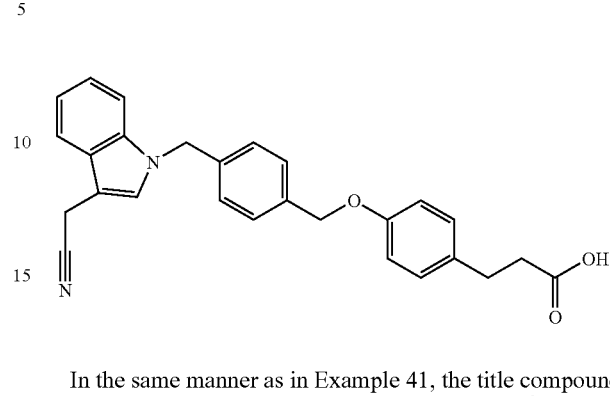

In the same manner as in Example 41, the title compound was obtained as beige crystals from methyl 3-(4-{[4-(chloromethyl)benzyl]oxy}phenyl)propanoate and 1H-indol-3-ylacetonitrile. yield 64%, MS (APCI−): 423 (M−H).

Example 55

3-{4-[(4-{[2-(4-fluorophenyl)-1H-indol-1-yl] methyl}benzyl)oxy]phenyl)propanoic acid

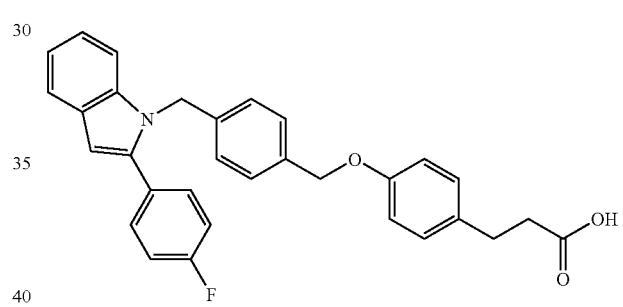

In the same manner as in Example 41, the title compound was obtained as colorless crystals from methyl 3-(4-{[4-(chloromethyl)benzyl]oxy}phenyl)propanoate and 2-(4-fluorophenyl)-1H-indole. yield 29%, MS (APCI−): 478 (M−H).

Example 56

3-[4-({4-[(2-phenyl-1H-imidazol-1-yl)methyl]benzyl]oxy)phenyl]propanoic acid

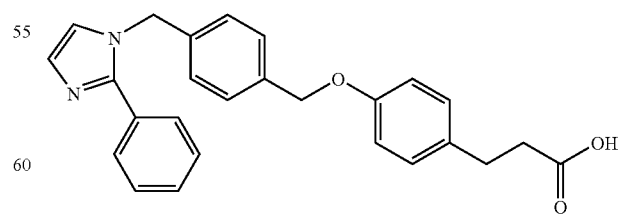

In the same manner as in Example 41, the title compound was obtained as colorless crystals from methyl 3-(4-{[4-(chloromethyl)benzyl]oxy}phenyl)propanoate and 2-phenyl-1H-imidazole. yield 71%, MS (APCI−): 411 (M−H).

Example 57

3-[4-({4-[(5-fluoro-2-propyl-1H-indol-1-yl)methyl]benzyl}oxy)phenyl]propanoic acid

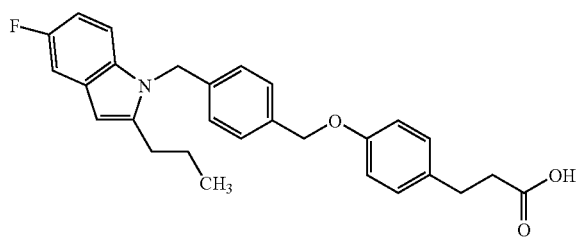

To a solution of 5-fluoro-2-propyl-1H-indole (0.17 g, 0.98 mmol) in N,N-dimethylformamide (6.2 mL) was added sodium hydride (60% in oil, 39 mg, 0.98 mmol) with stirring at 0° C., and the mixture was stirred at the same temperature for 10 min. Methyl 3-(4-([4-(chloromethyl)benzyl]oxy}phenyl)propanoate (0.31 g, 0.98 mmol) and sodium iodide (0.15 g, 0.98 mmol) were added to the obtained mixture and the mixture was stirred at room temperature for 17 hr. The reaction mixture was diluted with ethyl acetate, and the mixture washed with 5% aqueous potassium hydrogensulfate solution, water and saturated brine, dried over anhydrous magnesium sulfate, and concentrated under reduced pressure to give an oil. Then, a mixture of the obtained oil, 1 N aqueous sodium hydroxide solution (2.0 mL), methanol (5.0 mL) and tetrahydrofuran (10.0 mL) was stirred at room temperature for 2 hr. The reaction mixture was diluted with ethyl acetate, and the mixture washed with 1 N hydrochloric acid and saturated brine, dried over anhydrous magnesium sulfate, and concentrated under reduced pressure. The residue was purified by preparative HPLC (gradient cycle A), and the object fractions were collected and concentrated. Water was added to the residue, and the mixture was adjusted to pH 7 with saturated aqueous sodium hydrogencarbonate, and extracted with ethyl acetate. The organic layer was dried over anhydrous magnesium sulfate and concentrated under reduced pressure to give the title compound (0.13 g, yield 31%) as colorless crystals. MS (APCI-): 444 (M-H).

Example 58

3-[4-({4-[(2-isopropyl-1H-indol-1-yl)methyl]benzyl}oxy)phenyl]propanoic acid

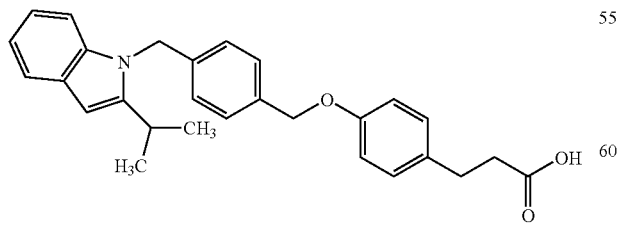

In the same manner as in Example 57, the title compound was obtained as colorless crystals from methyl 3-(4-{[4-(chloromethyl)benzyl]oxy}phenyl)propanoate and 2-isopropyl-1H-indole synthesized according to the method described in J. Med. Chem., 1996, vol. 39, pp. 892-903. yield 20%, MS (APCI-): 426 (M-H).

Example 59

3-[4-({4-[(2-phenyl-1H-benzimidazol-1-yl)methyl]benzyl}oxy)phenyl]propanoic acid

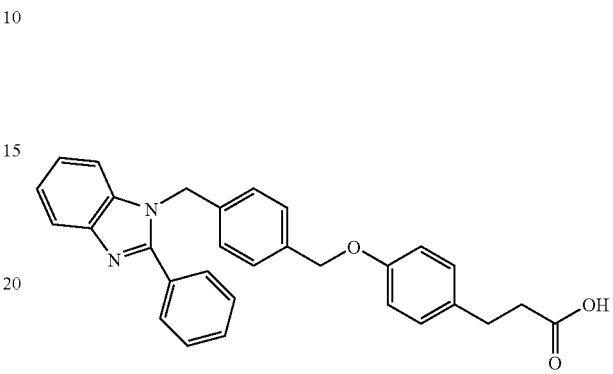

In the same manner as in Example 57, the title compound was obtained as colorless crystals from methyl 3-(4-{[4-(chloromethyl)benzyl]oxy}phenyl)propanoate and 2-phenyl-1H-benzimidazole. yield 67%, MS (APCI-): 461 (M-H).

Example 60

3-[4-({4-isobutoxy-3-[(2-phenyl-1H-indol-1-yl)methyl]benzyl)oxy)phenyl]propanoic acid

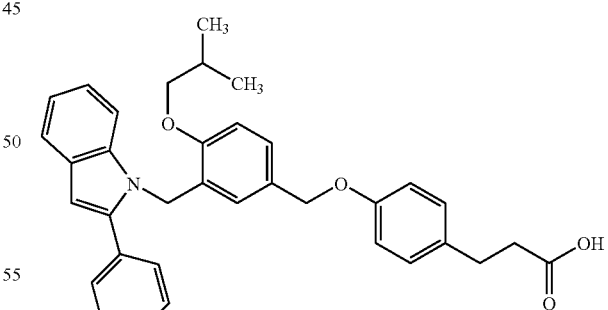

In the same manner as in Example 46, the title compound was obtained as colorless crystals from methyl 3-(4-hydroxyphenyl)propanoate and {4-isobutoxy-3-[(2-phenyl-1H-indol-1-yl)methyl]phenyl}methanol. yield 62%, MS (APCI-): 532 (M-H).

Example 61

3-[4-({3-[(2-phenyl-1H-indol-1-yl)methyl]benzyl}oxy)phenyl]propanoic acid

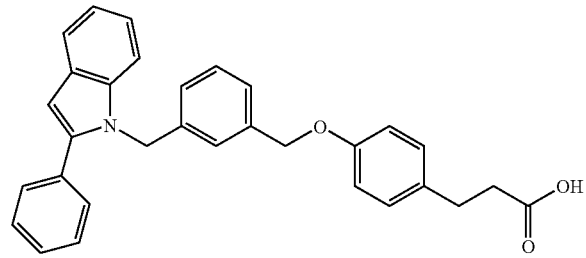

In the same manner as in Example 46, the title compound was obtained as a colorless powder from methyl 3-(4-hydroxyphenyl)propanoate and (3-[(2-phenyl-1H-indol-1-yl)methyl]phenyl}methanol. yield 69%, MS (APCI-):460 (M-H).

Example 62

3-[4-({4-[(2,5-diphenyl-1H-pyrrol-1-yl)methyl]benzyl}oxy)phenyl]propanoic acid

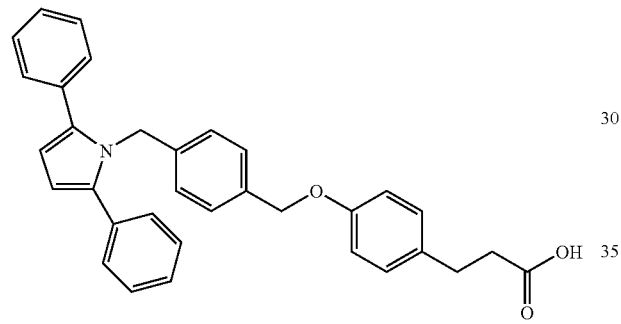

In the same manner as in Example 46, the title compound was obtained as colorless crystals from methyl 3-(4-hydroxyphenyl)propanoate and (4-[(2,5-diphenyl-1H-pyrrol-1-yl)methyl]phenyl}methanol. yield 56%, MS (APCI-): 486 (M-H), $^1$H NMR (CDCl$_3$) δ: 2.64 (2H, t, J=7.8 Hz), 2.89 (2H, t, J=7.8 Hz), 4.92 (2H, s), 5.23 (2H, s), 6.35 (2H, s), 6.66 (2H, d, J=8.1 Hz), 6.84 (2H, d, J=8.4 Hz), 7.10 (2H, d, J=8.4 Hz), 7.17 (2H, d, J=8.1 Hz), 7.21-7.39 (10H, m).

Example 63

3-[4-({4-[(2-methyl-3,4-dihydroquinolin-1 (2H)-yl)methyl]benzyl}oxy)phenyl]propanoic acid

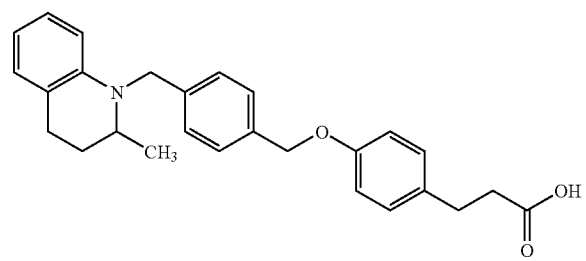

To a solution of 2-methyl-1,2,3,4-tetrahydroquinoline (0.19 mL, 1.32 mmol) in N,N-dimethylformamide (3.5 mL) was added sodium hydride (60% in oil, 53 mg, 1.32 mmol) with stirring at 0° C., and the mixture was stirred at the same temperature for 10 min. Methyl 3-(4-{[4-(chloromethyl)benzyl]oxy}phenyl)propanoate (0.35 g, 1.10 mmol) and sodium iodide (0.20 g, 1.32 mmol) were added to the obtained mixture and the mixture was stirred at room temperature for 18 hr. The reaction mixture was diluted with ethyl acetate, and the mixture washed with 5% aqueous potassium hydrogensulfate solution, water and saturated brine, dried over anhydrous magnesium sulfate, and concentrated under reduced pressure to give an oil. Then, a mixture of the obtained oil, 1 N aqueous sodium hydroxide solution (2.2 mL), methanol (4.0 mL) and tetrahydrofuran (8.0 mL) was stirred at room temperature for 2 hr. The reaction mixture was adjusted to pH 7 with 1 N hydrochloric acid, and diluted with ethyl acetate. The mixture washed with water and saturated brine, dried over anhydrous magnesium sulfate, and concentrated under reduced pressure. The residue was purified by silica gel column chromatography (hexane/ethyl acetate=4/1-hexane/ethyl acetate=1/2) to give the title compound (0.21 g, yield 47%) as beige crystals. MS (APCI-): 414 (M-H).

Example 64

3-[4-({4-[(2,2-dimethylquinolin-1 (2H)-yl)methyl]benzyl}oxy)phenyl]propanoic acid

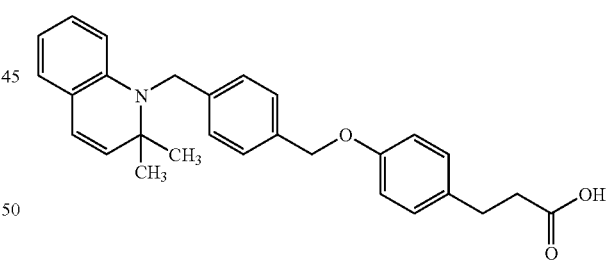

In the same manner as in Example 63, the title compound was obtained as colorless crystals from methyl 3-(4-{[4-(chloromethyl)benzyl]oxy}phenyl)propanoate and 2,2-dimethyl-1,2-dihydroquinoline synthesized according to the method described in *J. Med. Chem.*, 1998, vol. 41, pp. 623-639. yield 38%, MS (APCI-): 426 (M-H).

Example 65

3-(4-{[4-({5-(2-phenylethyl)-3-[4-(trifluoromethyl)phenyl]-1H-pyrazol-1-yl}methyl)benzyl]oxy}phenyl)propanoic acid

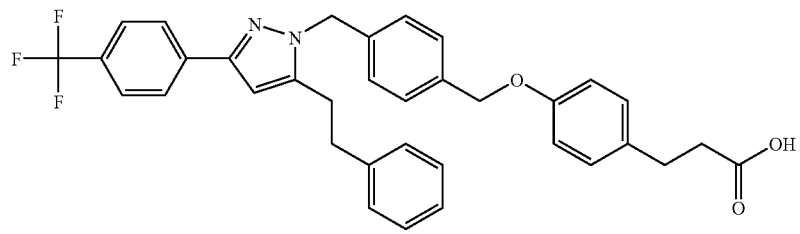

A mixture of 5-(2-phenylethyl)-3-[4-(trifluoromethyl)phenyl]-1H-pyrazole (350 mg, 1.11 mmol), sodium hydride (60% in oil, 40 mg, 1.00 mmol) and N,N-dimethylformamide (5 mL) was stirred at room temperature for 1 hr. Methyl 3-(4-([4-(chloromethyl)benzyl]oxy)phenyl)propanoate (318 mg, 1.00 mmol) was added to the reaction mixture at room temperature and the mixture was further stirred at room temperature for 1 hr. The reaction mixture was poured into 1N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give a yellow oil. The yellow oil was dissolved in a mixed solvent of methanol (5 mL) and tetrahydrofuran (5 mL), and 2 N aqueous sodium hydroxide solution (2 mL) was added. The mixture was stirred at room temperature for 1 hr. The reaction mixture was diluted with water, and neutralized with 1 N hydrochloric acid. The mixture was extracted with ethyl acetate. The ethyl acetate layer was dried using a Presep Dehydration tube (Manufactured by Wako Pure Chemical Industries, Ltd.), and concentrated under reduced pressure to give the title compound (550 mg, yield 75%) as colorless crystals. MS: m/z 585 (MH$^+$), $^1$H NMR (CDCl$_3$) δ: 2.58-2.67 (2H, m), 2.80-2.94 (6H, m), 5.00 (2H, s), 5.26 (2H, s), 6.46 (1H, s), 6.86 (2H, d, J=8.9 Hz), 7.06-7.14 (6H, m), 7.18-7.32 (3H, m), 7.36 (2H, d, J=8.3 Hz), 7.63 (2H, d, J=8.1 Hz), 7.90 (2H, d, J=8.1 Hz).

Example 66 methyl 3-(4-{[4-({5-[(E)-2-phenylvinyl]-3-[4-(trifluoromethyl)phenyl]-1H-pyrazol-1-yl}methyl)benzyl]oxy}phenyl)propanoate

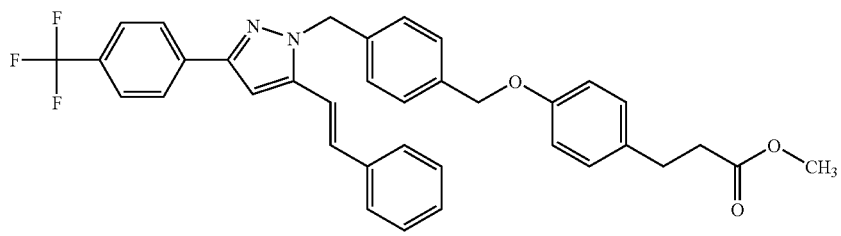

A mixture of 5-[(E)-2-phenylvinyl]-3-[4-(trifluoromethyl)phenyl]-1H-pyrazole (330 mg, 1.05 mmol), sodium hydride (60% in oil, 40 mg, 1.00 mmol) and N,N-dimethylformamide (5 mL) was stirred at room temperature for 1 hr. Methyl 3-(4-{[4-(chloromethyl)benzyl]oxy}phenyl)propanoate (318 mg, 1.00 mmol) was added to the reaction mixture at room temperature, and the mixture was further stirred at room temperature for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give the title compound (343 mg, yield 57%) as a yellow oil. MS: m/z 597 (MH$^+$).

Example 67

3-(4-{[4-({5-[(E)-2-phenylvinyl]-3-[4-(trifluoromethyl)phenyl]-1H-pyrazol-1-yl}methyl)benzyl]oxy}phenyl)propanoic acid

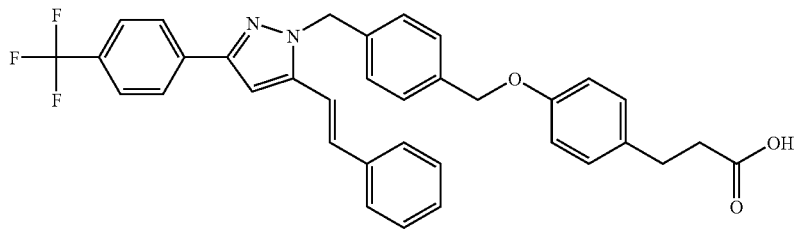

Methyl 3-(4-{[4-({5-[(E)-2-phenylvinyl]-3-[4-(trifluoromethyl)phenyl]-1H-pyrazol-1-yl}methyl)benzyl]oxy}phenyl)propanoate (250 mg, 0.419 mmol) was dissolved in a mixed solvent of methanol (5 mL) and tetrahydrofuran (5 mL), and 2 N aqueous sodium hydroxide solution (2 mL) was added. The mixture was stirred at room temperature for 1 hr. The reaction mixture was diluted with water, and neutralized with 1 N hydrochloric acid. The mixture was extracted with ethyl acetate. The ethyl acetate layer was dried using a Presep Dehydration tube (Manufactured by Wako Pure Chemical Industries, Ltd.), and concentrated under reduced pressure to give the title compound (220 mg, yield 90%) as colorless crystals. MS: m/z 583 (MH$^+$), $^1$H NMR (DMSO-d$_6$) δ: 2.45 (2H, t, J=7.5 Hz), 2.72 (2H, t, J=7.5 Hz), 5.00 (2H, s), 5.65 (2H, s), 6.86 (2H, d, J=8.5 Hz), 7.09 (2H, d, J=8.5 Hz), 7.22-7.46 (10H, m), 7.64 (2H, d, J=7.4 Hz), 7.77 (2H, d, J=8.2 Hz), 8.05 (2H, d, J=8.0 Hz), 12.05 (1H, s).

Example 68 methyl 3-[4-([4-[(3,5-diphenyl-1H-pyrazol-1-yl)methyl]benzyl]oxy)phenyl]propanoate

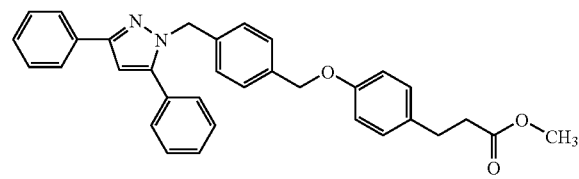

In the same manner as in Example 66, the title compound was obtained as a yellow oil from 3,5-diphenyl-1H-pyrazole and methyl 3-(4-{[4-(chloromethyl)benzyl]oxy}phenyl)propanoate. yield 93%, MS: m/z 503 (MH$^+$).

Example 69

3-[4-({4-[(3,5-diphenyl-1H-pyrazol-1-yl)methyl]benzyl}oxy)phenyl]propanoic acid

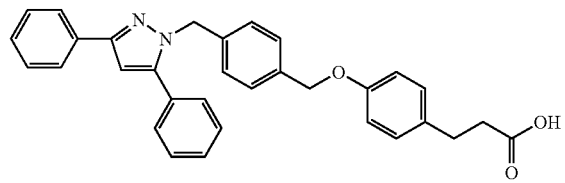

In the same manner as in Example 67, the title compound was obtained as colorless crystals from methyl 3-[4-({4-[(3,5-diphenyl-1H-pyrazol-1-yl)methyl]benzyl}oxy)phenyl]propanoate. yield 79%, MS: m/z 489 (MH$^+$), $^1$H NMR (CDCl$_3$) δ: 2.64 (2H, t, J=7.6 Hz), 2.89 (2H, t, J=7.6 Hz), 4.99 (2H, s), 5.40 (2H, s), 6.66 (1H, s), 6.87 (2H, d, J=8.7 Hz), 7.07-7.14 (4H, m), 7.30-7.45 (10H, m), 7.84-7.90 (2H, m).

Example 70

3-{4-[(4-{[3-(4-fluorophenyl)-4-(2-phenylethyl)-1H-pyrazol-1-yl]methyl}benzyl)oxy]phenyl}propanoic acid A mixture of 3-(4-fluorophenyl)-1H-pyrazole-4-carbaldehyde (190 mg, 1.00 mmol), sodium hydride (60% in oil, 40 mg, 1.00 mmol) and N,N-dimethylformamide (5 mL) was stirred at room temperature for 1 hr. Methyl 3-(4-{[4-(chloromethyl)benzyl]oxy}phenyl)propanoate (318 mg, 1.00 mmol) was added to the reaction mixture at room tempera ture, and the mixture was further stirred for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give a yellow oil. The oil was dissolved in N,N-dimethylformamide (5 mL), benzyltriphenylphosphonium bromide (660 mg, 1.52 mmol) and potassium carbonate (276 mg, 2.00 mmol) were added, and the mixture was stirred at room temperature for 12 hr. The reaction mixture was poured into 1 N hydrochloric acid, and the mixture was extracted with ethyl acetate. The ethyl acetate layer was concentrated under reduced pressure to give a yellow oil. The yellow oil was dissolved in a mixed solvent of tetrahydrofuran (20 mL) and methanol (20 mL), and platinum oxide (50 mg) was added. The mixture was stirred under an atmospheric hydrogen atmosphere at room temperature for 2 hr. The platinum catalyst was filtered off, and the filtrate was concentrated under reduced pressure. The residue was purified by HPLC (gradient cycle A) to give a colorless oil. The colorless oil was dissolved in a mixed solvent of methanol (5 mL) and tetrahydrofuran (5 mL), and 2 N sodium hydroxide aqueous solution (2 mL) was added. The mixture was stirred at room temperature for 1 hr. The reaction mixture was diluted with water, and neutralized with 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure to give the title compound (86 mg, yield 16%) as a colorless oil. MS: m/z 535 (MH$^+$), $^1$H NMR (CDCl$_3$) δ: 2.66 (2H, t, J=7.6 Hz), 2.76-2.95 (6H, m), 5.05 (2H, s), 5.39 (2H, s), 6.90 (2H, d, J=8.7 Hz), 7.03-7.26 (12H, m), 7.41-7.53 (4H, m).

Example 71

3-[2-fluoro-4-({4-[(3-(4-fluorophenyl)-4-([4-(trifluoromethyl)phenoxy]methyl}-1H-pyrazol-1-yl)methyl]benzyl)oxy)phenyl]propanoic acid

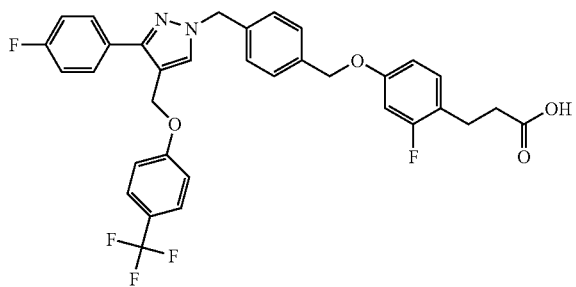

A mixture of 3-(4-fluorophenyl)-1H-pyrazole-4-carbaldehyde (190 mg, 1.00 mmol), sodium hydride (60% in oil, 40 mg, 1.00 mmol) and N,N-dimethylformamide (5 mL) was stirred at room temperature for 1 hr. Methyl 4-(bromomethyl)benzoate (230 mg, 1.00 mmol) was added to the reaction mixture at room temperature, and the mixture was further stirred at room temperature for 1 hr. The reaction mixture was poured into 1N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give a yellow oil. The yellow oil was dissolved in methanol (10 mL), sodium borohydride (40 mg, 1.06 mmol) was added at room temperature, and the mixture was stirred at room temperature for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure to give a yellow oil. 4-(Trifluoromethyl)phenol (108 mg, 0.666 mmol), triphenylphosphine (262 mg, 1.00 mmol) and toluene (10 mL) were added to the yellow oil, diethyl azodicarboxylate (40% toluene solution, 0.5 mL, 1.10 mmol) was added at room temperature and the mixture was stirred for 1 hr. The reaction mixture was concentrated under reduced pressure, and the residue was purified by silica gel column chromatography (hexane:ethyl acetate=19:1-1:1) to give a yellow oil. The yellow oil was dissolved in tetrahydrofuran (10 mL), lithium aluminum hydride (40 mg, 1.05 mmol) was added at 0° C., and the mixture was stirred at the same temperature for 1 hr. Sodium sulfate decahydrate (350 mg) was added to the reaction mixture, and the mixture was allowed to warm to room temperature and stirred for 1 hr. The insoluble material was filtered off. The organic layer was concentrated under reduced pressure, ethyl 3-(2-fluoro-4-hydroxyphenyl)propanoate (100 mg, 0.471 mmol), triphenylphosphine (130 mg, 0.496 mmol) and dichloromethane (3 mL) were added to the residue. Diethyl azodicarboxylate (40% toluene solution, 0.3 mL, 0.661 mmol) as added at room temperature and the mixture was stirred for 1 hr. The reaction mixture was concentrated under reduced pressure, and the residue was purified by silica gel column chromatography (hexane:ethyl acetate=19:1-1:1) to give a yellow oil. The yellow oil was dissolved in a mixed solvent of ethanol (5 mL) and tetrahydrofuran (5 mL), and 2 N aqueous sodium hydroxide solution (2 mL) was added. The mixture was stirred at room temperature for 1 hr. The reaction mixture was diluted with water, and neutralized with 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by HPLC (gradient cycle A) to give the title compound (86 mg, yield 14%) as a colorless oil. MS: m/z 623 (MH$^+$).

Example 72

3-(4-{[3-(1-benzothiophen-3-yl)benzyl]oxy}phenyl)-N-(cyanomethyl)propanamide

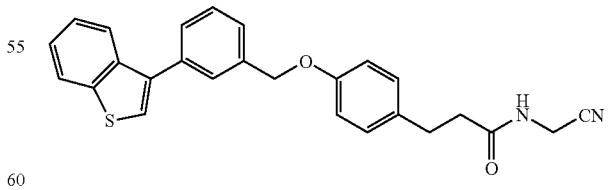

A solution of 3-(4-{[3-(1-benzothiophen-3-yl)benzyl]oxy}phenyl)propanoic acid (0.20 g, 0.51 mmol), aminoacetonitrile sulfate (65 mg, 0.62 mmol), triethylamine (0.17 mL, 1.22 mmol), 1-hydroxybenzotriazole (91 mg, 0.67 mmol) and 1-ethyl-3-(3-dimethylaminopropyl)carbodiimide hydrochloride (0.13 g, 0.68 mmol) in N,N-dimethylformamide (15 mL) was stirred at room temperature for 18 hr. The reaction solution was diluted with ethyl acetate, and the mixture was washed successively with aqueous citric acid solution, aqueous sodium bicarbonate and aqueous sodium chloride solution, dried over anhydrous magnesium sulfate, and concentrated under reduced pressure. The obtained pale-yellow oil was crystallized from diethyl ether to give the title compound (142 mg, yield 33%) as colorless needle crystals. MS: m/z 427 (MH+).

Example 73

3-(4-{[4-({4-[2-(phenylsulfonyl)ethyl]piperazin-1-yl)methyl)benzyl]oxy}phenyl)propanoic acid

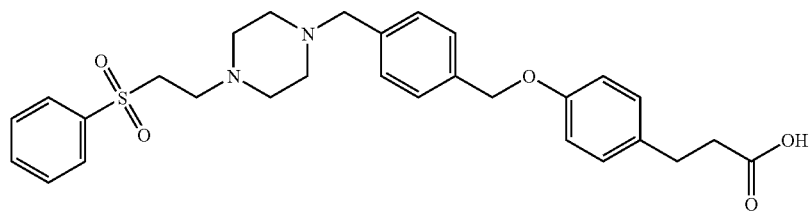

To a solution of methyl 3-(4-([4-(chloromethyl)benzyl]oxy}phenyl)propanoate (50 mg, 0.16 mmol) in N,N-dimethylformamide (1 mL) were added a suspension of 1-(2-benzenesulfonylethyl)piperazine dihydrochloride (62 mg, 0.19 mmol) in N,N-dimethylformamide (0.5 mL) and potassium carbonate (80 mg, 0.58 mmol) and the mixture was stirred at 70° C. for 66 hr. Water (2 mL) was added to the reaction mixture, and the mixture was extracted with dichloromethane (2 mL). The organic layer was concentrated by a GeneVac centrifugation concentration apparatus under reduced pressure. The obtained product was dissolved in methanol (2 mL), 1 N aqueous sodium hydroxide solution (0.32 mL, 0.32 mmol) was added, and the mixture was stirred at room temperature for 18 hr. The reaction mixture was acidified with 1 N Hydrochloric acid, and the precipitated crystals were collected by filtration, and washed with diethyl ether to give the title compound (51.5 mg, yield 63%). MS (ESI+, m/e) 523 (M+1).

Examples 74 to 87 were synthesized in the same manner as in Example 73.

Example 74

3-{4-[(4-{[4-(phenylsulfonyl)piperazin-1-yl]methyl}benzyl)oxy]phenyl}propanoic acid

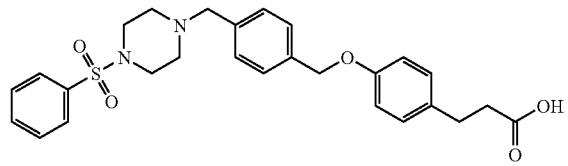

yield 75%, MS (ESI+, m/e) 495 (M+1).

Example 75

3-[4-({4-[(2-phenylmorpholin-4-yl)methyl]benzyl}oxy)phenyl]propanoic acid

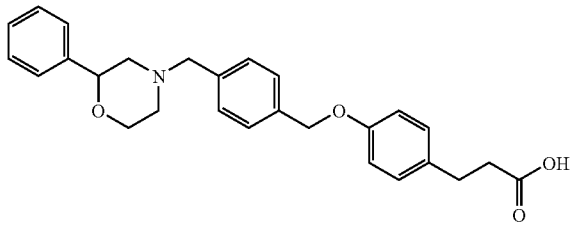

yield 82%, MS (ESI+, m/e) 432 (M+1).

Example 76

3-{4-[(4-{[4-(pyridin-3-ylmethyl)piperazin-1-yl]methyl}benzyl)oxy]phenyl}propanoic acid

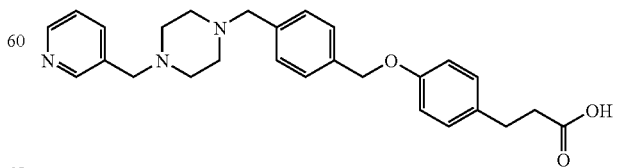

yield 67%, MS (ESI+, m/e) 446 (M+1).

Example 77

3-{4-[(4-{[4-(pyridin-4-ylmethyl)piperazin-1-yl]methyl}benzyl)oxy]phenyl}propanoic acid

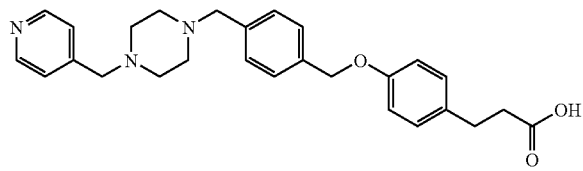

yield 63%, MS (ESI+, m/e) 446 (M+1).

Example 78

3-{4-[(4-{[4-(4-fluorobenzyl)piperidin-1-yl]methyl}benzyl)oxy]phenyl}propanoic acid

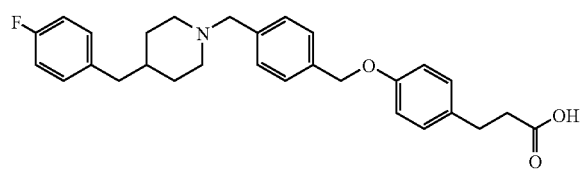

yield 75%, MS (ESI+, m/e) 462 (M+1).

Example 79

3-[4-({4-[(4-phenoxypiperidin-1-yl)methyl]benzyl}oxy)phenyl]propanoic acid

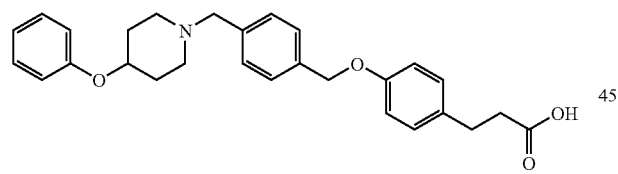

yield 68%, MS (ESI+, m/e) 446 (M+1).

Example 80

3-{4-[(4-{[4-(2-chlorophenoxy)piperidin-1-yl]methyl}benzyl)oxy]phenyl}propanoic acid

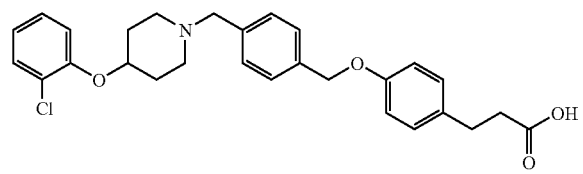

yield 84%, MS (ESI+, m/e) 480 (M+1).

Example 81

3-{4-[(4-{[(3S,4R)-3-(methoxycarbonyl)-4-phenylpyrrolidin-1-yl]methyl}benzyl)oxy]phenyl}propanoic acid

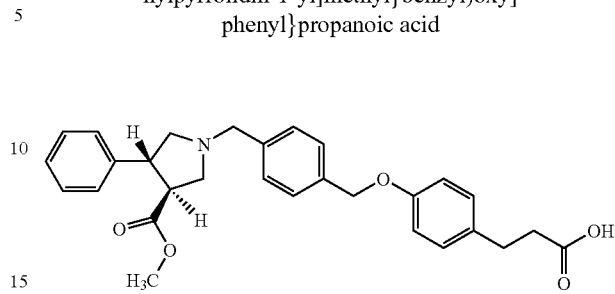

yield 82%, MS (ESI+, m/e) 460 (M+1).

Example 82

3-[4-({4-[(3-benzylpyrrolidin-1-yl)methyl]benzyl}oxy)phenyl]propanoic acid

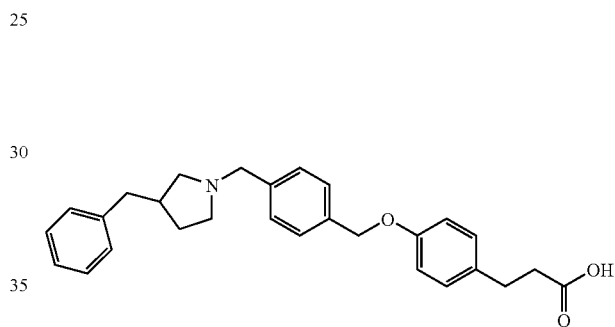

yield 85%, MS (ESI+, m/e) 430 (M+1).

Example 83

3-{4-[(4-{[4-(2-methylphenoxy)piperidin-1-yl]methyl}benzyl)oxy]phenyl}propanoic acid

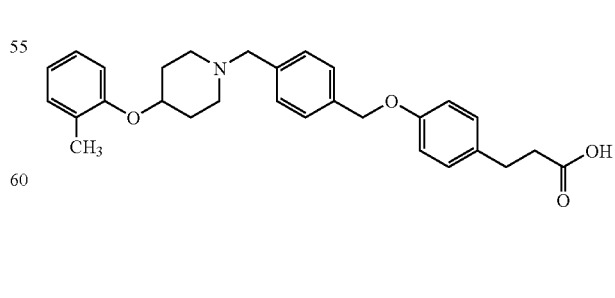

yield 83%, MS (ESI+, m/e) 460 (M+1).

Example 84

3-[4-({4-[(4,4-diphenylpiperidin-1-yl)methyl]benzyl}oxy)phenyl]propanoic acid

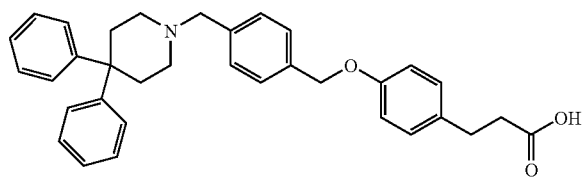

yield 76%, MS (ESI+, m/e) 506 (M+1).

Example 85

3-[4-({4-[(2-methyl-2,3-dihydro-1H-indol-1-yl)methyl]benzyl}oxy)phenyl]propanoic acid

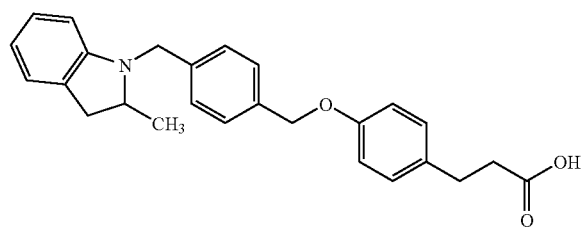

yield 14%, MS (ESI+, m/e) 402 (M+1).

Example 86

3-[4-({4-[(4-phenylpiperidin-1-yl)methyl]benzyl}oxy)phenyl]propanoic acid

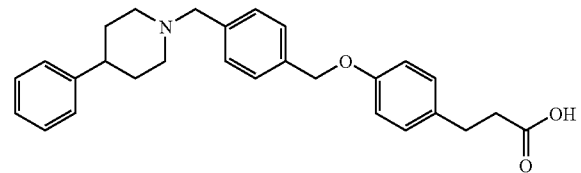

yield 76%, MS (ESI+, m/e) 430 (M+1).

Example 87

3-{4-[(4-{[4-(2-methylphenyl)piperidin-1-yl]methyl}benzyl)oxy]phenyl}propanoic acid

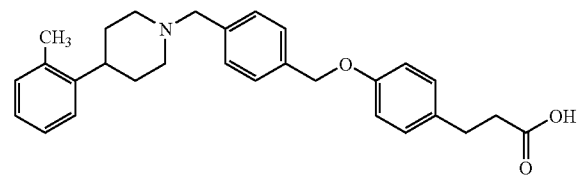

yield 62%, MS (ESI+, m/e) 444 (M+1).

Example 88

3-[4-({4-[(1-methyl-3,4-dihydroisoquinolin-2 (1H)-yl)methyl]benzyl}oxy)phenyl]propanoic acid trifluoroacetate

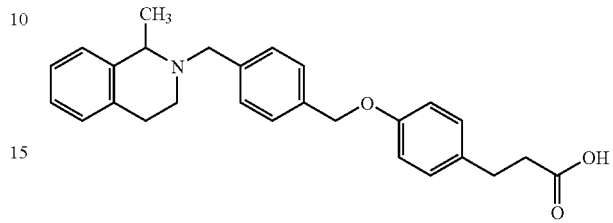

To a solution of methyl 3-(4-([4-(chloromethyl)benzyl]oxy)phenyl)propanoate (50 mg, 0.16 mmol) in N,N-dimethylformamide (1 mL) were added a solution of 1-methyl-1,2,3,4-tetrahydroisoquinoline (35 mg, 0.19 mmol) in N,N-dimethylformamide (0.5 mL) and potassium carbonate (33 mg, 0.24 mmol) and the mixture was stirred at 70° C. for 66 hr. Water (2 mL) was added to the reaction mixture, and the mixture was extracted with dichloromethane (2 mL). The organic layer was concentrated by a GeneVac centrifugation concentration apparatus under reduced pressure. The obtained product was dissolved in methanol (2 mL), and 1 N aqueous sodium hydroxide solution (0.32 mL, 0.32 mmol) was added. The mixture was stirred at room temperature for 18 hr. The reaction mixture was acidified with 1 N hydrochloric acid, and the mixture was extracted with dichloromethane (2 mL). The organic layer was concentrated by a GeneVac centrifugation concentration apparatus under reduced pressure. The residue was purified by preparative HPLC (gradient cycle B) to give the title compound (47.5 mg, yield 57%). MS (ESI+, m/e) 416 (M+1).

Examples 89 to 110 were synthesized in the same manner as in Example 88.

Example 89

3-{4-[(4-{[3-(phenylsulfonyl)pyrrolidin-1-yl]methyl}benzyl)oxy]phenyl}propanoic acid trifluoroacetate

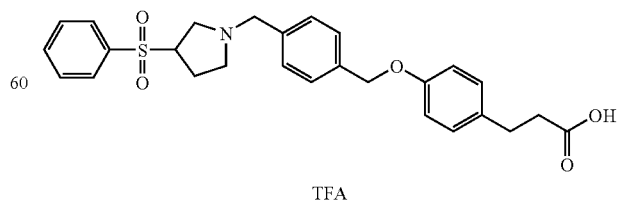

yield 30%, MS (ESI+, m/e) 480 (M+1).

Example 90

3-{4-[(4-{[4-(diphenylmethyl)piperazin-1-yl]methyl}benzyl)oxy]phenyl}propanoic acid ditrifluoroacetate

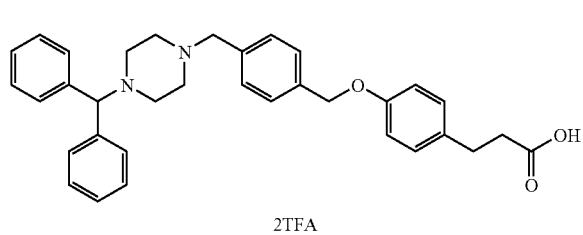

yield 51%, MS (ESI+, m/e) 521 (M+1).

Example 91

3-{4-[(4-{[4-(pyridin-2-ylmethyl)piperazin-1-yl]methyl}benzyl)oxy]phenyl}propanoic acid tritrifluoroacetate

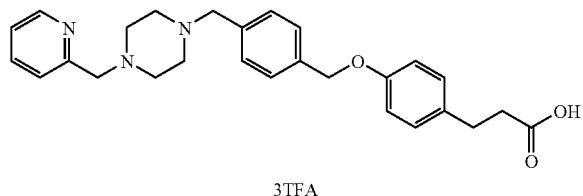

yield 42%, MS (ESI+, m/e) 446 (M+1).

Example 92

3-{4-[(4-{[3-benzyl-3-(ethoxycarbonyl)piperidin-1-yl]methyl}benzyl)oxy]phenyl)propanoic acid trifluoroacetate

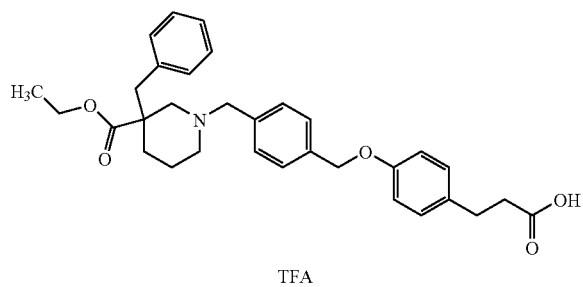

yield 72%, MS (ESI+, m/e) 516 (M+1).

Example 93

3-[4-({4-[(2-phenylpyrrolidin-1-yl)methyl]benzyl)oxy)phenyl]propanoic acid trifluoroacetate

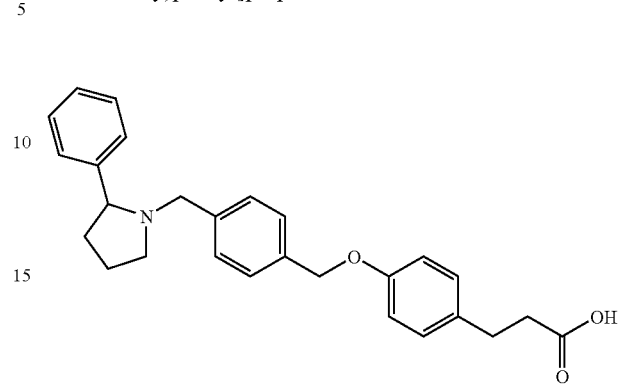

yield 76%, MS (ESI+, m/e) 416 (M+1).

Example 94

3-[4-({4-[(3-phenylpyrrolidin-1-yl)methyl]benzyl}oxy)phenyl]propanoic acid trifluoroacetate

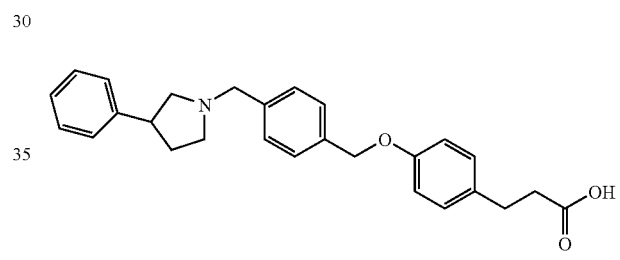

yield 43%, MS (ESI+, m/e) 416 (M+1).

Example 95

3-[4-({4-[(3-pyrazin-2-ylpyrrolidin-1-yl)methyl]benzyl}oxy)phenyl]propanoic acid trifluoroacetate

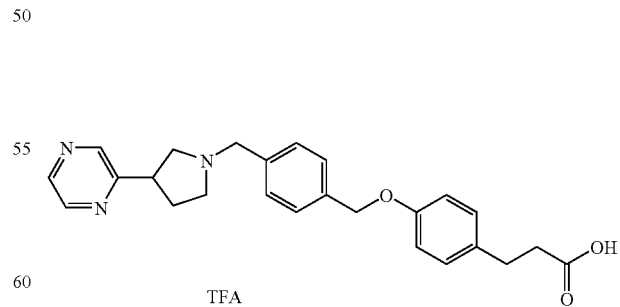

yield 20%, MS (ESI+, m/e) 418 (M+1).

Example 96

3-{4-[(4-{[2-(2-methylphenyl)pyrrolidin-1-yl]methyl}benzyl)oxy]phenyl}propanoic acid trifluoroacetate

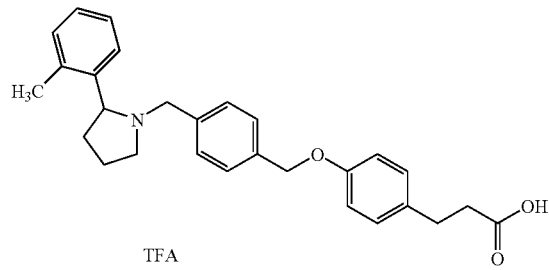

yield 74%, MS (ESI+, m/e) 430 (M+1).

Example 97

3-[4-({4-[(2-benzylpyrrolidin-1-yl)methyl]benzyl}oxy)phenyl]propanoic acid trifluoroacetate

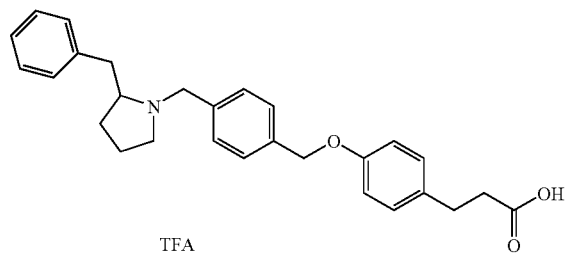

yield 59%, MS (ESI+, m/e) 430 (M+1).

Example 98

3-{4-[(4-{[2-(2-phenylethyl)pyrrolidin-1-yl]methyl}benzyl)oxy]phenyl}propanoic acid trifluoroacetate

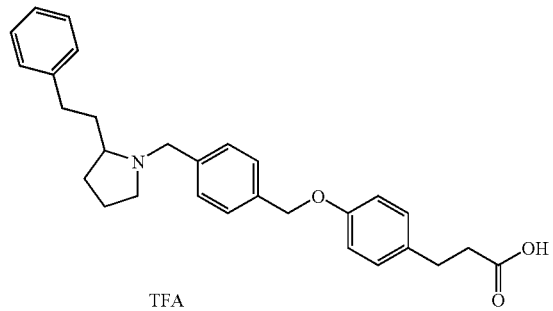

yield 75%, MS (ESI+, m/e) 444 (M+1).

Example 99

3-[4-({4-[(2-cyclohexylpyrrolidin-1-yl)methyl]benzyl}oxy)phenyl]propanoic acid trifluoroacetate

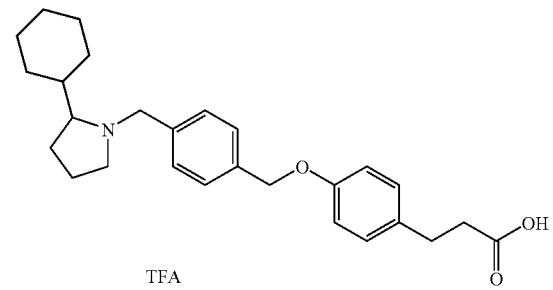

yield 47%, MS (ESI+, m/e) 422 (M+1).

Example 100

3-[4-({4-[(2-isopropylpyrrolidin-1-yl)methyl]benzyl}oxy)phenyl]propanoic acid trifluoroacetate

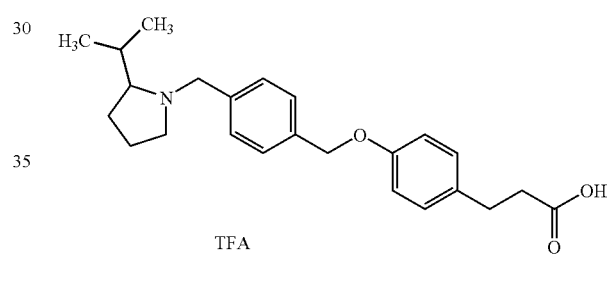

yield 32%, MS (ESI+, m/e) 382 (M+1).

Example 101

3-(4-[(4-{[3-(2-chlorobenzyl)pyrrolidin-1-yl]methyl}benzyl)oxy]phenyl}propanoic acid trifluoroacetate

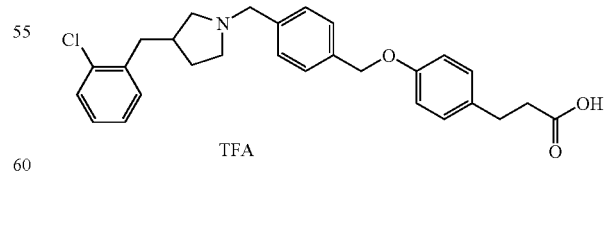

yield 44%, MS (ESI+, m/e) 464 (M+1).

Example 102

3-{4-[(4-{[3-(2-phenylethyl)pyrrolidin-1-yl]methyl}benzyl)oxy]phenyl}propanoic acid trifluoroacetate

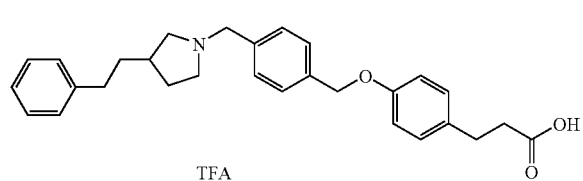

yield 41%, MS (ESI+, m/e) 444 (M+1).

Example 103

3-(4-{[4-(3,4-dihydroquinoline-1 (2H)-ylmethyl)benzyl]oxy}phenyl)propanoic acid trifluoroacetate

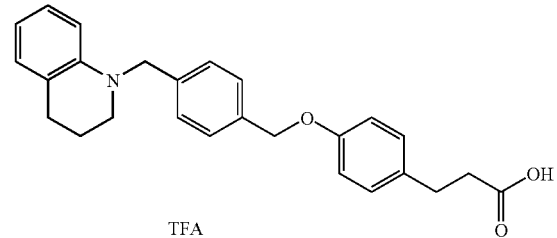

yield 31%, MS (ESI+, m/e) 402 (M+1).

Example 104

3-(4-{[4-(3,4-dihydroisoquinoline-2 (1H)-ylmethyl)benzyl]oxy}phenyl)propanoic acid trifluoroacetate

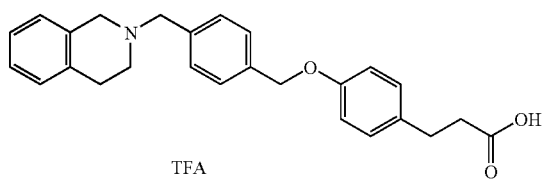

yield 69%, MS (ESI+, m/e) 402 (M+1).

Example 105

3-{4-[(4-{[2-(2,4-difluorophenyl)-5,6,7,8-tetrahydro-4H-[1,3]thiazolo[5,4-b]azepin-4-yl]methyl}benzyl)oxy]phenyl}propanoic acid trifluoroacetate

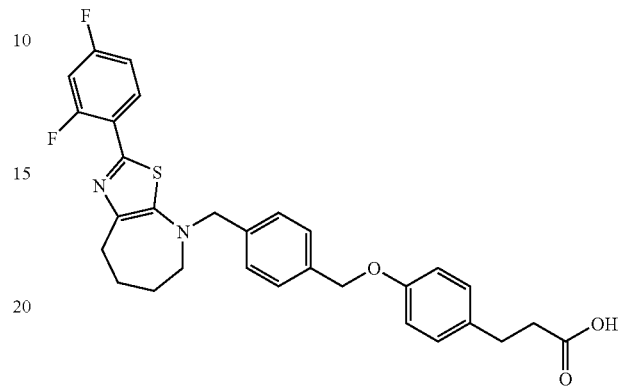

yield 3%, MS (ESI+, m/e) 535 (M+1).

Example 106

3-[4-({4-[(2-biphenyl-4-yl-5,6,7,8-tetrahydro-4H-[1,3]thiazolo[5,4-b]azepin-4-yl)methyl]benzyl}oxy)phenyl]propanoic acid trifluoroacetate

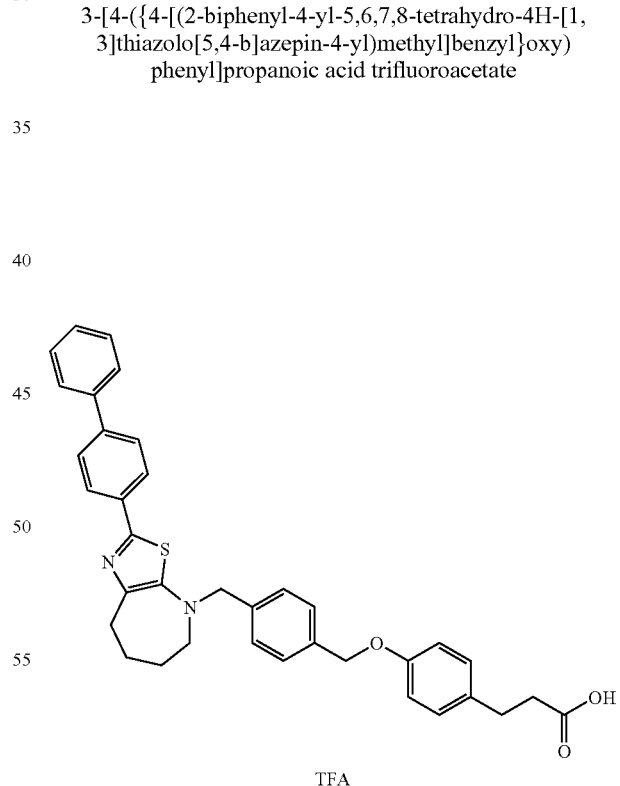

yield 1%, MS (ESI+, m/e) 575 (M+1).

Example 107

3-(4-[(4-{[2-(4-cyano-3-methylphenyl)-5,6,7,8-tetrahydro-4H-[1,3]thiazolo[5,4-b]azepin-4-yl]methyl}benzyl)oxy]phenyl}propanoic acid trifluoroacetate

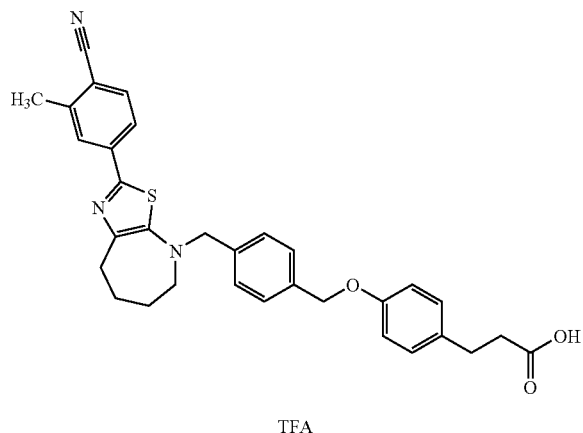

yield 2%, MS (ESI+, m/e) 538 (M+1).

Example 108

3-[4-({4-[(2-imidazo[1,2-a]pyridin-2-yl-5,6,7,8-tetrahydro-4H-[1,3]thiazolo[5,4-b]azepin-4-yl)methyl]benzyl}oxy)phenyl]propanoic acid ditrifluoroacetate

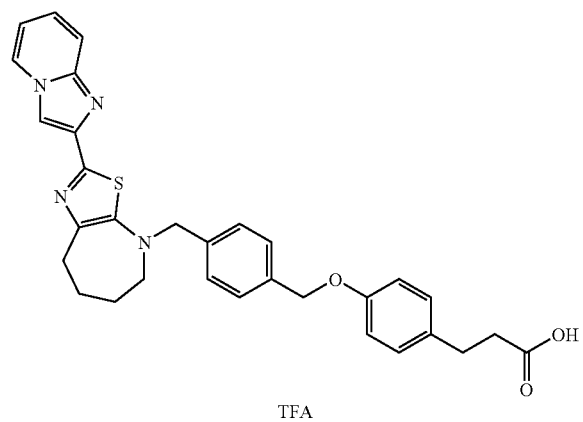

yield 3%, MS (ESI+, m/e) 539 (M+1).

Example 109

3-(4-{[4-(3,4-dihydro-1,5-benzothiazepin-5 (2H)-ylmethyl)benzyl]oxy)phenyl)propanoic acid trifluoroacetate

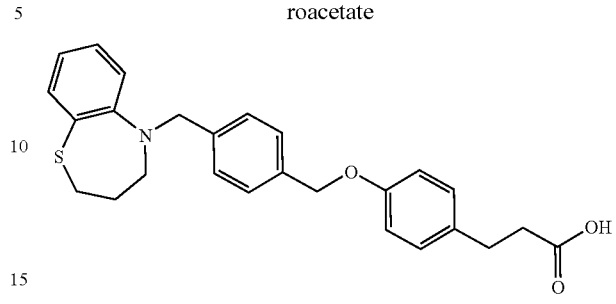

yield 28%, MS (ESI+, m/e) 434 (M+1).

Example 110

3-[4-({4-[(8-methoxy-2,3,4,5-tetrahydro-1H-1-benzazepin-1-yl)methyl]benzyl}oxy)phenyl]propanoic acid trifluoroacetate

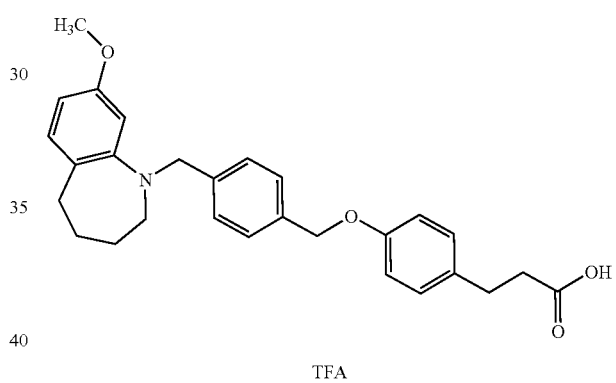

yield 30%, MS (ESI+, m/e) 446 (M+1).

Example 111

3-[4-({4-isobutoxy-3-[(2-methyl-3,4-dihydroquinolin-1 (2H)-yl)methyl]benzyl}oxy)phenyl]propanoic acid

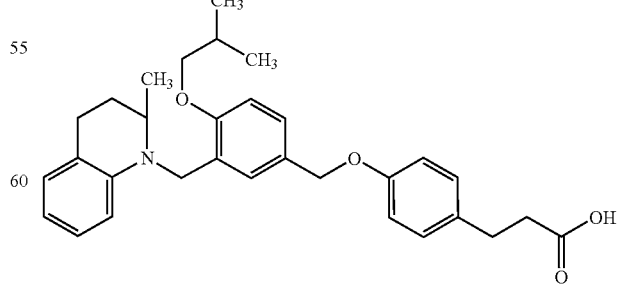

In the same manner as in Example 46, the title compound was obtained as colorless crystals from methyl 3-(4-hydroxyphenyl)propanoate and {4-isobutoxy-3-[(2-methyl-3,4-dihydroquinolin-1 (2H)-yl)methyl]phenyl}methanol. yield 59%, MS (APCI–): 486 (M–H).

Example 112

3-[4-([4-[(3-methyl-5-phenyl-1H-pyrazol-1-yl)methyl]benzyl}oxy)phenyl]propanoic acid

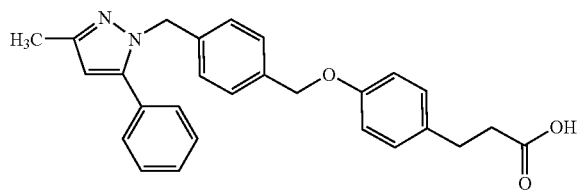

To a mixture of {4-[(3-methyl-5-phenyl-1H-pyrazol-1-yl)methyl]phenyl}methanol (139 mg, 0.5 mmol), methyl 3-(4-hydroxyphenyl)propanoate (90 mg, 0.5 mmol), triphenylphosphine (262 mg, 1.0 mmol) and dichloromethane (3 mL) was added dropwise diethyl azodicarboxylate (40% toluene solution, 435 mg, 1.0 mmol) with stirring at room temperature, and the mixture was stirred at room temperature for 1 hr. After completion of the reaction, the reaction mixture was purified by silica gel column chromatography (hexane:ethyl acetate=19:1-1:2) to give a yellow oil. The yellow oil was dissolved in methanol (3 mL) and tetrahydrofuran (3 mL), and 1 N aqueous sodium hydroxide solution (2 mL) was added. The mixture was stirred at room temperature for 1 hr. The reaction mixture was diluted with water, and neutralized with 1 N hydrochloric acid. The mixture was extracted with ethyl acetate. The ethyl acetate layer was dried using a Presep Dehydration tube (Manufactured by Wako. Pure Chemical Industries, Ltd.), and concentrated under reduced pressure. The residue was purified by silica gel column chromatography (hexane:ethyl acetate=9:1-1:4) to give the title compound (90 mg, yield 42%, 2 steps) as colorless crystals.

$^1$H NMR (CDCl$_3$) δ: 2.33 (3H, s), 2.62 (2H, t, J=7.6 Hz), 2.89 (2H, t, J=7.6 Hz), 4.98 (2H, s), 5.31 (2H, s), 6.15 (1H, s), 6.86 (2H, d, J=8.5 Hz), 7.03 (2H, d, J=8.1 Hz), 7.10 (2H, d, J=8.5 Hz), 7.28-7.35 (4H, m), 7.35-7.41 (3H, m).

Example 113 methyl 3-[4-({4-[(5-methyl-3-phenyl-1H-pyrazol-1-yl)methyl]benzyl}oxy)phenyl]propanoate

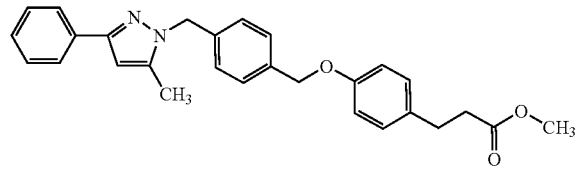

To a mixture of {4-[(5-methyl-3-phenyl-1H-pyrazol-1-yl)methyl]phenyl}methanol (278 mg, 1.0 mmol), methyl 3-(4-hydroxyphenyl)propanoate (180 mg, 1.0 mmol), triphenylphosphine (393 mg, 1.5 mmol) and dichloromethane (5 mL) was added dropwise diethyl azodicarboxylate (40% toluene solution, 650 mg, 1.5 mmol) with stirring at room temperature, and the mixture was stirred at room temperature for 1 hr. After completion of the reaction, the reaction mixture was purified by silica gel column chromatography (hexane:ethyl acetate=19:1-1:2) to give the title compound (263 mg, yield 90%) as a yellow oil.

$^1$H NMR (CDCl$_3$) δ: 2.22 (3H, s), 2.59 (2H, t, J=7.8 Hz), 2.88 (2H, t, J=7.8 Hz), 3.66 (3H, s), 5.00 (2H, s), 5.34 (2H, s), 6.39 (1H, d, J=0.8 Hz), 6.87 (2H, d, J=8.7 Hz), 7.07-7.20 (4H, m), 7.27-7.32 (1H, m), 7.34-7.44 (4H, m), 7.78-7.82 (2H, m).

Example 114

3-[4-({4-[(5-methyl-3-phenyl-1H-pyrazol-1-yl)methyl]benzyl}oxy)phenyl]propanoic acid

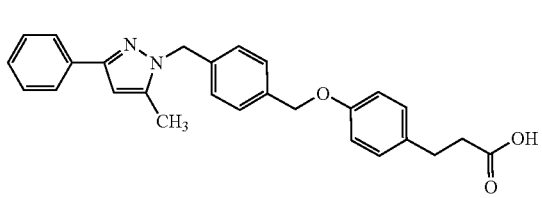

Methyl 3-[4-({4-[(5-methyl-3-phenyl-1H-pyrazol-1-yl)methyl]benzyl}oxy)phenyl]propanoate (220 mg, 0.5 mmol) was dissolved in a mixed solvent of methanol (3 mL) and tetrahydrofuran (3 mL), and 1 N aqueous sodium hydroxide solution (2 mL) was added. The mixture was stirred at room temperature for 1 hr. The reaction mixture was diluted with water, and neutralized with 1 N hydrochloric acid. The mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=9:1-1:4) to give the title compound (155 mg, yield 73%) as colorless crystals. $^1$H NMR (CDCl$_3$) δ: 2.22 (3H, s), 2.64 (2H, t, J=7.5 Hz), 2.89 (2H, t, J=7.5 Hz), 5.00 (2H, s), 5.35 (2H, s), 6.38 (1H, s), 6.87 (2H, d, J=8.5 Hz), 7.07-7.18 (4H, m), 7.23-7.32 (1H, m), 7.33-7.44 (4H, m), 7.76-7.83 (2H, m).

Example 115

3-[4-({4-[(5-isopropyl-3-phenyl-1H-pyrazol-1-yl)methyl]benzyl}oxy)phenyl]propanoic acid

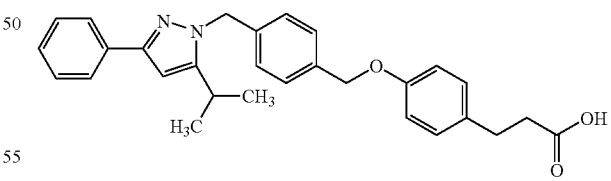

A mixture of 3-isopropyl-5-phenyl-1H-pyrazole (186 mg, 1.0 mmol), sodium hydride (60% in oil, 40 mg, 1.0 mmol) and N,N-dimethylformamide (5 mL) was stirred at room temperature for 1 hr. Methyl 3-(4-{[4-(chloromethyl)benzyl]oxy}phenyl)propanoate (318 mg, 1.00 mmol) was added to the reaction mixture at room temperature, and the mixture was further stirred for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give a yellow oil. The yellow oil was dissolved in a mixed solvent of methanol (3 mL) and tetrahydrofuran (3 mL), and 1 N aqueous sodium hydroxide solution (2 mL) was added. The mixture was stirred at room temperature for 1 hr. The reaction mixture was diluted with water, neutralized with 1 N hydrochloric acid, and extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=9:1-1:4) to give the title compound (254 mg, yield 56%, 2 steps) as a colorless oil.

$^1$H NMR (CDCl$_3$) δ: 1.20 (6H, d, J=7.0 Hz), 2.64 (2H, t, J=7.5 Hz), 2.89 (2H, t, J=7.5 Hz), 5.00 (2H, s), 5.39 (2H, s), 6.41 (1H, s), 6.87 (2H, d, J=8.7 Hz), 7.08-7.14 (4H, m), 7.25-7.42 (5H, m), 7.79-7.84 (2H, m).

Example 116

3-[4-({4-[(3-isopropyl-5-phenyl-1H-pyrazol-1-yl)methyl]benzyl)oxy)phenyl]propanoic acid

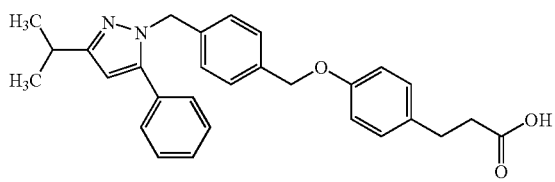

In the same manner as in Example 112, the title compound was obtained from methyl 3-(4-hydroxyphenyl)propanoate and {4-[(3-isopropyl-5-phenyl-1H-pyrazol-1-yl)methyl]phenyl}methanol. yield 73% (2 steps), $^1$H NMR (CDCl$_3$) δ: 1.31 (6H, d, J=7.0 Hz), 2.63 (2H, t, J=7.7 Hz), 2.89 (2H, t, J=7.6 Hz), 2.99-3.10 (1H, m), 4.99 (2H, s), 5.32 (2H, s), 6.18 (1H, s), 6.87 (2H, d, J=8.7 Hz), 7.02 (2H, d, J=8.3 Hz), 7.11 (2H, d, J=8.7 Hz), 7.28-7.40 (7H, m).

Example 117 ethyl 3-[4-({3-[1-(2-ethoxyethyl)-2-phenyl-1H-indol-3-yl]benzyl}oxy)-2-fluorophenyl]propanoate

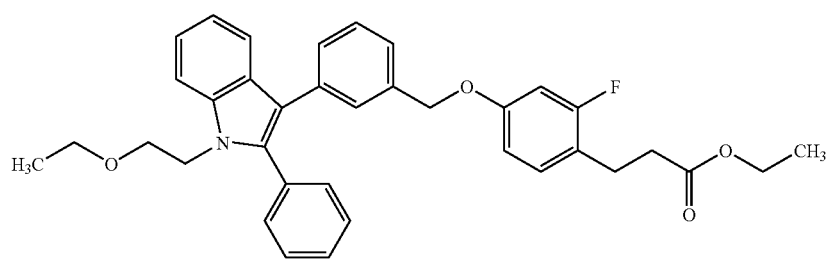

In the same manner as in Example 1, the title compound was obtained as a colorless oil from ethyl 3-(2-fluoro-4-hydroxyphenyl)propanoate and (3-[1-(2-ethoxyethyl)-2-phenyl-1H-indol-3-yl]phenyl}methanol. yield 85%, MS: m/z 566 (MH$^+$).

Example 118

3-[4-({3-[1-(2-ethoxyethyl)-2-phenyl-1H-indol-3-yl]benzyl}oxy)-2-fluorophenyl]propanoic acid

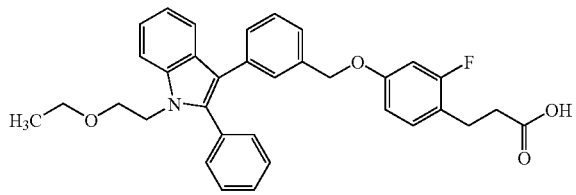

In the same manner as in Example 2, the title compound was obtained as colorless needle crystals from ethyl 3-[4-({3-[1-(2-ethoxyethyl)-2-phenyl-1H-indol-3-yl]benzyl]oxy)-2-fluorophenyl]propanoate. yield 85% (recrystallized from heptane-ethyl acetate), MS: m/z 538 (MH$^+$).

Example 119 methyl 3-[4-({4-[(4-hydroxypiperidin-1-yl)methyl]benzyl}oxy)phenyl]propanoate

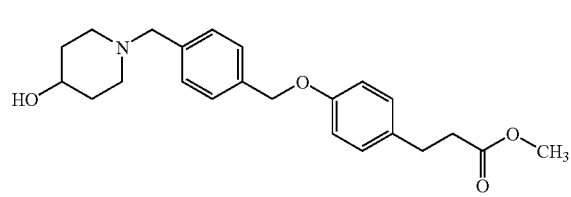

A mixture of methyl 3-(4-{[4-(chloromethyl)benzyl]oxy}phenyl)propanoate (0.6 g, 1.88 mmol), 4-hydroxypiperidine (0.29 g, 2.82 mmol), potassium carbonate (0.39 g, 2.82 mmol) and N,N-dimethylformamide (12 mL) was stirred at 60° C. for 21 hr. The reaction mixture was diluted with ethyl acetate, and the mixture washed with water and

Example 120 ethyl 3-[4-({3-[(3,5-dimethyl-1H-pyrazol-1-yl)methyl]-4-isobutoxybenzyl}oxy)-2-fluorophenyl]propanoate

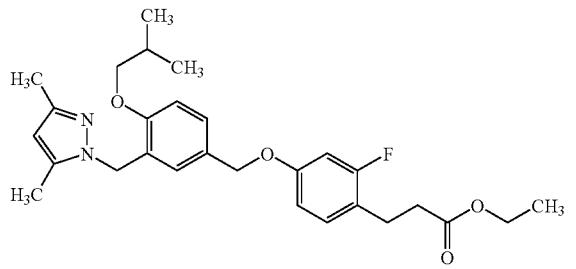

In the same manner as in Example 5, the title compound was obtained as a colorless oil from ethyl 3-(2-fluoro-4-hydroxyphenyl)propanoate and {3-[(3,5-dimethyl-1H-pyrazol-1-yl)methyl]-4-isobutoxyphenyl}methanol. yield 77%, MS (ESI+): 483 (M+H).

Example 121

3-[4-({3-[(3,5-dimethyl-1H-pyrazol-1-yl)methyl]-4-isobutoxybenzyl}oxy)-2-fluorophenyl]propanoic acid

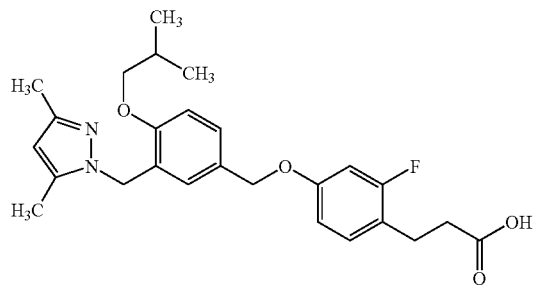

To a mixed solution of ethyl 3-[4-({3-[(3,5-dimethyl-1H-pyrazol-1-yl)methyl]-4-isobutoxybenzyl}oxy)-2-fluorophenyl]propanoate (0.37 g, 0.77 mmol) in methanol (2 mL) and tetrahydrofuran (4 mL) was added 1 N aqueous sodium hydroxide solution (1.5 mL), and the mixture was stirred at room temperature for 2 hr. The reaction mixture was neutralized with 1 N hydrochloric acid, and diluted with ethyl acetate. The mixture washed with water and saturated brine, dried over anhydrous magnesium sulfate, and concentrated under reduced pressure. The residue was purified by silica gel column chromatography (hexane/ethyl acetate=10/1-hexane/ethyl acetate=1/2) to give the title compound (0.25 g, yield 56%) as colorless crystals.

MS (ESI+): 455 (M+H).

Example 122 ethyl 3-[4-({4-[(3,5-diphenyl-1H-pyrazol-1-yl)methyl]-3-isopropoxybenzyl}oxy)-2-fluorophenyl]propanoate

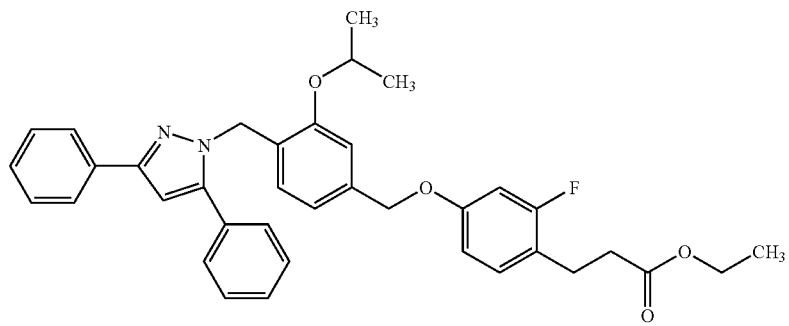

In the same manner as in Example 5, the title compound was obtained as a colorless oil from ethyl 3-(2-fluoro-4-hydroxyphenyl)propanoate and {4-[(3,5-diphenyl-1H-pyrazol-1-yl)methyl]-3-isopropoxyphenyl}methanol. yield 92%, MS (ESI+): 593 (M+H).

Example 123

3-[4-({4-[(3,5-diphenyl-1H-pyrazol-1-yl)methyl]-3-isopropoxybenzyl}oxy)-2-fluorophenyl]propanoic acid

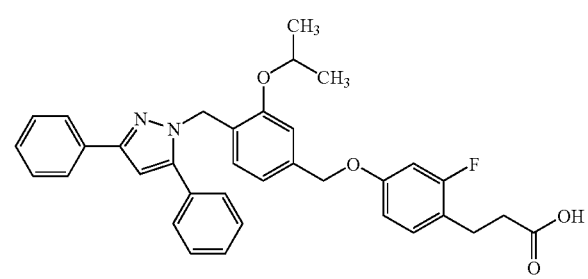

In the same manner as in Example 121, the title compound was obtained as a colorless oil from ethyl 3-[4-({4-[(3,5- diphenyl-1H-pyrazol-1-yl)methyl]-3-isopropoxybenzyl}oxy)-2-fluorophenyl]propanoate. yield 87%, MS (ESI+): 565 (M+H).

Example 124

3-[4-({4-[(3,5-diphenyl-1H-pyrazol-1-yl)methyl]-3-isopropoxybenzyl}oxy)-2-fluorophenyl]propanoic acid calcium salt

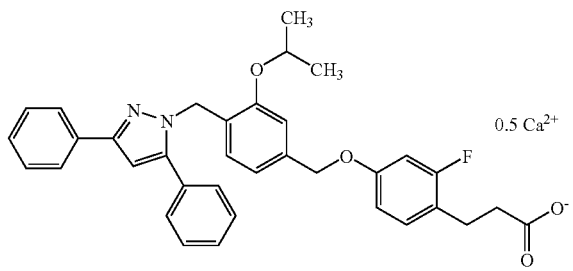

3-[4-({4-[(3,5-Diphenyl-1H-pyrazol-1-yl)methyl]-3-isopropoxybenzyl)oxy)-2-fluorophenyl]propanoic acid (0.32 g, 0.56 mmol) was dissolved in methanol (3 mL), and 1 N aqueous sodium hydroxide solution (0.56 mL, 0.56 mmol) was added. Then, a solution of calcium chloride (31 mg, 0.28 mmol) in water (1 mL) was added, and the precipitated solid was collected by filtration, washed with water and methanol, and dried to give the title compound (0.27 g, yield 83%) as a colorless powder. MS (ESI+): 565 (M+H, as free form).

Example 125 methyl 3-[4-({4-[(3,5-diphenyl-1H-pyrazol-1-yl)methyl]-3-isopropoxybenzyl}oxy)-2-methylphenyl]propanoate

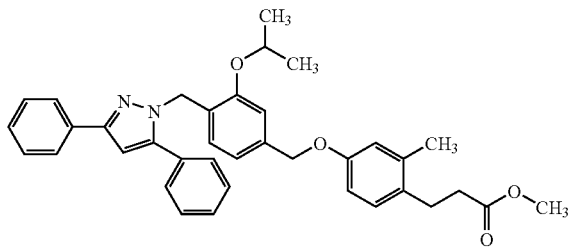

In the same manner as in Example 5, the title compound was obtained as a colorless oil from methyl 3-(4-hydroxy-2-methylphenyl)propanoate and (4-[(3,5-diphenyl-1H-pyrazol-1-yl)methyl]-3-isopropoxyphenyl}methanol. yield 46%, $^1$H NMR (CDCl$_3$) δ: 1.26 (6H, d, J=6.0 Hz), 2.29 (3H, s), 2.48-2.62 (2H, m), 2.82-2.93 (2H, m), 3.68 (3H, s), 4.57 (1H, m), 4.97 (2H, s), 5.39 (2H, s), 6.68-6.83 (4H, m), 6.86 (1H, m), 6.92 (1H, s), 7.03 (1H, d, J=8.1 Hz), 7.31 (1H, m), 7.34-7.46 (7H, m), 7.84-7.92 (2H, m).

Example 126

3-[4-({4-[(3,5-diphenyl-1H-pyrazol-1-yl)methyl]-3-isopropoxybenzyl}oxy)-2-methylphenyl]propanoic acid

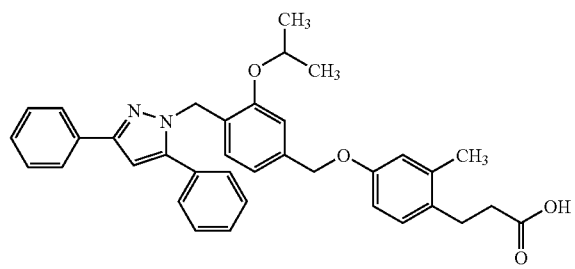

To a mixed solution of methyl 3-[4-({4-[(3,5-diphenyl-1H-pyrazol-1-yl)methyl]-3-isopropoxybenzyl}oxy)-2-methylphenyl]propanoate (0.20 g, 0.35 mmol) in methanol (2 mL) and tetrahydrofuran (4 mL) was added 1 N aqueous sodium hydroxide solution (0.70 mL, 0.70 mmol), and the mixture was stirred at 50° C. for 2 hr. The reaction mixture was neutralized with 1 N hydrochloric acid, and diluted with ethyl acetate. The mixture washed with water and saturated brine, dried over anhydrous magnesium sulfate, and concentrated under reduced pressure. The residue was purified by preparative HPLC (gradient cycle A). The obtained oil was diluted with ethyl acetate, and neutralized with saturated aqueous sodium hydrogencarbonate, and the mixture washed with saturated brine, dried over anhydrous magnesium sulfate, and concentrated under reduced pressure to give the title compound (0.15 g, yield 77%) as a colorless oil. MS (ESI+): 561 (M+H).

Example 127

3-[4-({4-[(3,5-diphenyl-1H-pyrazol-1-yl)methyl]-3-isopropoxybenzyl}oxy)-2-methylphenyl]propanoic acid calcium salt

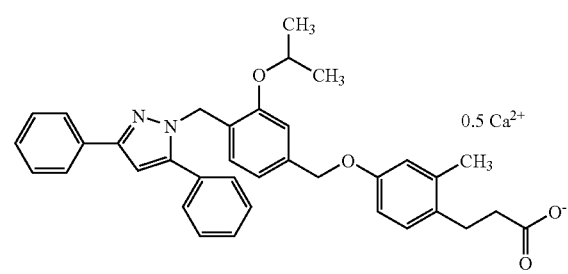

In the same manner as in Example 124, the title compound was obtained as a colorless powder from 3-[4-({4-[(3,5-diphenyl-1H-pyrazol-1-yl)methyl]-3-isopropoxybenzyl}oxy)-2-methylphenyl]propanoic acid. yield 74%.

Elemental analysis value for $C_{72}H_{70}N_4O_8Ca \cdot 0.5H_2O$
Calculated: C, 74.01; H, 6.12; N, 4.80.
Found: C, 74.19; H, 6.04; N, 4.61.

Example 128 ethyl 3-[4-({3-[1-(2-ethoxyethyl)-2-methyl-1H-indol-3-yl]benzyl}oxy)-2-fluorophenyl]propanoate

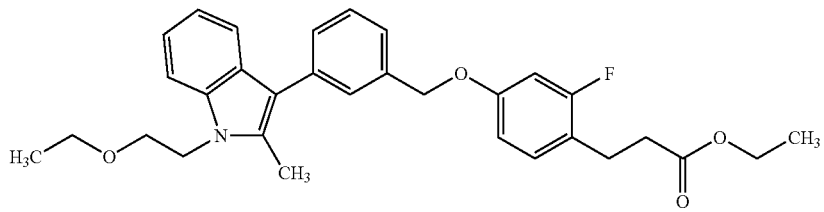

In the same manner as in Example 1, the title compound was obtained as a pale-yellow oil from ethyl 3-(2-fluoro-4-hydroxyphenyl)propanoate and {3-[1-(2-ethoxyethyl)-2-methyl-1H-indol-3-yl]phenyl}methanol. yield 90%, MS m/z 504 (MH$^+$).

Example 129

3-[4-({3-[1-(2-ethoxyethyl)-2-methyl-1H-indol-3-yl]benzyl}oxy)-2-fluorophenyl]propanoic acid

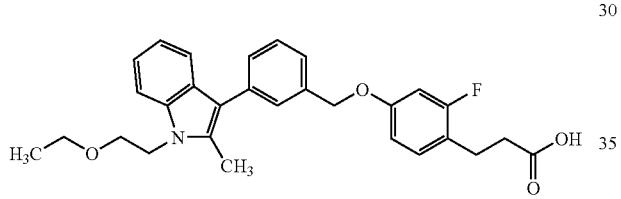

In the same manner as in Example 2, the title compound was obtained as a pale-yellow oil from ethyl 3-[4-({3-[1-(2-ethoxyethyl)-2-methyl-1H-indol-3-yl]benzyl}oxy)-2-fluorophenyl]propanoate. yield 98%, MS m/z 476 (MH$^+$).

Example 130 ethyl 3-{(4-[(4-{[3-tert-butyl-5-(phenoxymethyl)-1H-pyrazol-1-yl]methyl}benzyl)oxy]-2-fluorophenyl}propanoate

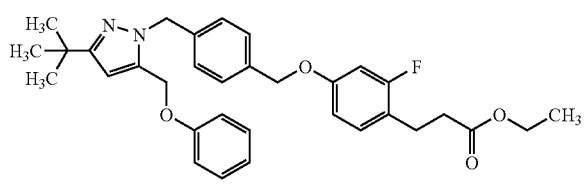

To a mixture of (4-{[3-tert-butyl-5-(phenoxymethyl)-1H-pyrazol-1-yl]methyl}phenyl)methanol (0.60 g, 1.7 mmol), ethyl 3-(2-fluoro-4-hydroxyphenyl)propanoate (0.40 g, 1.9 mmol), tributylphosphine (0.85 mL, 3.4 mmol) and tetrahydrofuran (50 mL) was added 1,1'-(azodicarbonyl)dipiperidine (0.86 g, 3.4 mmol), and the mixture was stirred at room temperature for 2 hr. The reaction solution was concentrated under reduced pressure, and diisopropyl ether was added to the residue. The insoluble material was filtered off, and the filtrate was concentrated under reduced pressure. The residue was subjected to silica gel column chromatography (ethyl acetate:hexane=1:4) to give the title compound (0.86 µg, yield 93%) as a colorless oil. MS: m/z 545 (MH$^+$).

Example 131

3-{4-[(4-{[3-tert-butyl-5-(phenoxymethyl)-1H-pyrazol-1-yl]methyl}benzyl)oxy]-2-fluorophenyl}propanoic acid calcium salt

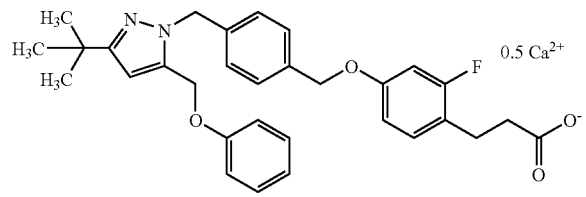

A mixture of ethyl 3-(4-[(4-{[3-tert-butyl-5-(phenoxymethyl)-1H-pyrazol-1-yl]methyl}benzyl)oxy]-2-fluorophenyl}propanoate (0.86 g, 1.6 mmol), 1 N aqueous sodium hydroxide solution (3.5 mL), tetrahydrofuran (6 mL) and methanol (6 mL) was stirred at 60° C. for 1 hr. 1 N Hydrochloric acid (3.5 mL) was added to the reaction mixture, and the mixture was extracted with ethyl acetate. The extract was washed with aqueous sodium chloride solution, dried over anhydrous magnesium sulfate, and concentrated under reduced pressure. The residue was subjected to silica gel column chromatography (ethyl acetate:hexane=1:2) to give a colorless oil (0.80 g). To a mixture of the obtained oil (0.80 g), 1 N aqueous sodium hydroxide solution (1.9 mL), methanol (2 mL) and water (20 mL) was slowly added a solution of calcium chloride (0.10 g, 0.90 mmol) in water (2 mL), and the precipitated solid was collected by filtration, washed with water, and dried to give the title compound (0.76 g, yield 88%) as a colorless amorphous powder.

MS: m/z 517 (MH$^+$), $^1$H NMR (DMSO-d$_6$) δ: 1.23 (9H, s), 2.14-2.30 (2H, m), 2.64-2.80 (2H, m), 4.99 (2H, s), 5.02 (2H, s), 5.30 (2H, s), 6.29 (1H, s), 6.63-6.98 (5H, m), 7.05-7.38 (7H, m).

Example 132 ethyl 3-{4-[(4-{[5-(benzyloxy)-3-tert-butyl-1H-pyrazol-1-yl]methyl}benzyl)oxy]-2-fluorophenyl}propanoate

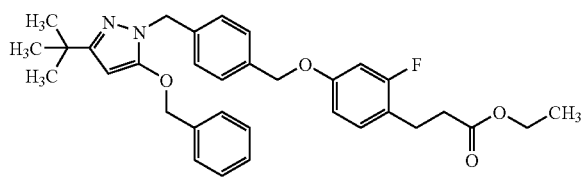

To a mixture of (4-([5-(benzyloxy)-3-tert-butyl-1H-pyrazol-1-yl]methyl)phenyl)methanol (0.60 g, 1.7 mmol), ethyl 3-(2-fluoro-4-hydroxyphenyl)propanoate (0.40 g, 1.9 mmol), tributylphosphine (0.85 mL, 3.4 mmol) and tetrahydrofuran (50 mL) was added 1,1'-(azodicarbonyl)dipiperidine (0.86 g, 3.4 mmol), and the mixture was stirred at room temperature for 2 hr. The reaction solution was concentrated under reduced pressure, diisopropyl ether was added to the residue, the insoluble material was filtered off, and the filtrate was concentrated under reduced pressure. The residue was subjected to silica gel column chromatography (ethyl acetate:hexane=1:4) to give the title compound (0.82 g, yield 88%) as a colorless oil. MS: m/z 545 (MH$^+$).

Example 133

3-{4-[(4-([5-(benzyloxy)-3-tert-butyl-1H-pyrazol-1-yl]methyl)benzyl)oxy]-2-fluorophenyl}propanoic acid calcium salt

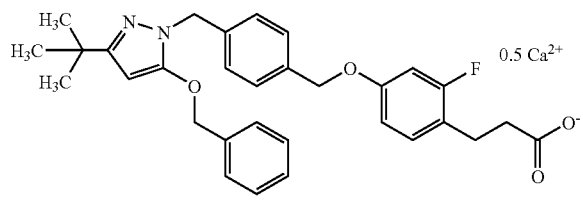

A mixture of ethyl 3-{4-[(4-{[5-(benzyloxy)-3-tert-butyl-1H-pyrazol-1-yl]methyl}benzyl)oxy]-2-fluorophenyl}propanoate (0.82 g, 1.5 mmol), 1 N aqueous sodium hydroxide solution (3.5 mL), tetrahydrofuran (6 mL) and methanol (6 mL) was stirred at 60° C. for 1 hr. 1 N Hydrochloric acid (3.5 mL) was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:2) to give a colorless oil (0.79 g). To a mixture of the obtained oil (0.79 g), 1 N aqueous sodium hydroxide solution (1.9 mL), methanol (2 mL) and water (20 mL) was slowly added a solution of calcium chloride (0.10 g, 0.90 mmol) in water (2 mL), and the precipitated solid was collected by filtration, washed with water, and dried to give the title compound (0.74 g, yield 93%) as a colorless amorphous powder.

MS: m/z 517 (MH$^+$), $^1$H NMR (DMSO-d$_6$) δ: 1.18 (9H, s), 2.15-2.30 (2H, m), 2.63-2.79 (2H, m), 4.98 (2H, s), 5.04 (2H, s), 5.09 (2H, s), 5.69 (1H, s), 6.63-6.83 (2H, m), 7.00-7.40 (10H, m).

Example 134 ethyl 3-[4-({4-[(3,5-di-tert-butyl-1H-pyrazol-1-yl)methyl]benzyl}oxy)-2-fluorophenyl]propanoate

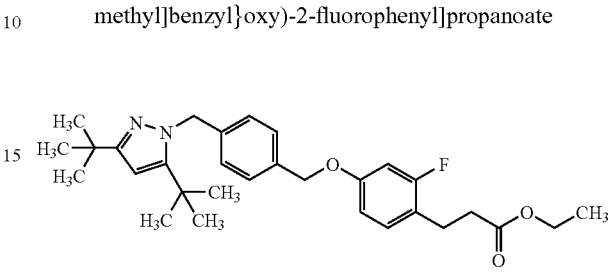

To a solution of 3,5-di-tert-butyl-1H-pyrazole (0.50 g, 2.8 mmol) in N,N-dimethylformamide (10 mL) was added sodium hydride (60% in oil, 0.13 g, 3.3 mmol) under ice-cooling and the mixture was stirred for 20 min. Then ethyl 3-(4-{[4-(chloromethyl)benzyl]oxy}-2-fluorophenyl)propanoate (0.98 g, 2.8 mmol) was added, and the mixture was stirred at room temperature for 3 hr. Water was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:4) to give the title compound (0.73 g, yield 57%) as colorless crystals. melting point 73-74° C.

Example 135

3-[4-({4-[(3,5-di-tert-butyl-1H-pyrazol-1-yl)methyl]benzyl}oxy)-2-fluorophenyl]propanoic acid

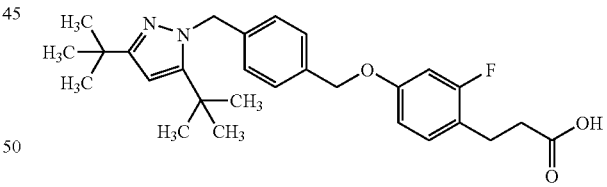

A mixture of ethyl 3-[4-({4-[(3,5-di-tert-butyl-1H-pyrazol-1-yl)methyl]benzyl}oxy)-2-fluorophenyl]propanoate (0.73 g, 1.6 mmol), 1 N aqueous sodium hydroxide solution (3.0 mL), tetrahydrofuran (6 mL) and methanol (6 mL) was stirred at 60° C. for 1 hr. 1 N Hydrochloric acid (3.0 mL) was added to the reaction mixture, and the mixture was extracted with ethyl acetate. The extract washed with aqueous sodium chloride solution, dried over anhydrous magnesium sulfate, and concentrated under reduced pressure. The obtained solid was recrystallized from ethyl acetate-hexane to give the title compound (0.61 g, yield 81%) as colorless crystals. melting point 152-153° C., $^1$H NMR (CDCl$_3$) δ: 1.26 (9H, s), 1.31 (9H, s), 2.55-2.66 (2H, m), 2.83-2.95 (2H, m), 4.96 (2H, s), 5.48 (2H, s), 5.92 (1H, s), 6.56-6.67 (2H, m), 6.84-6.94 (2H, m), 7.00-7.14 (1H, m), 7.26-7.34 (2H, m).

Example 136 ethyl 3-(4-([4-({3-tert-butyl-5-[(6-methylpyridin-2-yl)methoxy]-1H-pyrazol-1-yl}methyl)benzyl]oxy)-2-fluorophenyl)propanoate

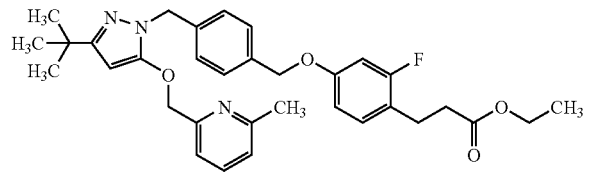

To a mixture of [4-({3-tert-butyl-5-[(6-methylpyridin-2-yl)methoxy]-1H-pyrazol-1-yl}methyl)phenyl]methanol (0.80 g, 2.2 mmol), ethyl 3-(2-fluoro-4-hydroxyphenyl)propanoate (0.49 g, 2.3 mmol), tributylphosphine (1.10 mL, 4.41 mmol) and tetrahydrofuran (40 mL) was added 1,1'-(azodicarbonyl)dipiperidine (1.11 g, 4.40 mmol), and the mixture was stirred at room temperature for 2 hr. The reaction solution was concentrated under reduced pressure, and diisopropyl ether was added to the residue. The insoluble material was filtered off, and the filtrate was concentrated under reduced pressure. The residue was subjected to silica gel column chromatography (ethyl acetate:hexane=2:3) to give the title compound (1.11 g, yield 90%) as a yellow oil. MS: m/z 560 (MH+).

Example 137

3-(4-{[4-({3-tert-butyl-5-[(6-methylpyridin-2-yl)methoxy]-1H-pyrazol-1-yl}methyl)benzyl]oxy}-2-fluorophenyl)propanoic acid calcium salt

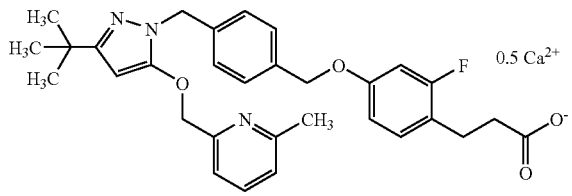

A mixture of ethyl 3-(4-{[4-({3-tert-butyl-5-[(6-methylpyridin-2-yl)methoxy]-1H-pyrazol-1-yl}methyl)benzyl]oxy}-2-fluorophenyl)propanoate (1.11 g, 1.98 mmol), 1 N aqueous sodium hydroxide solution (4.5 mL), tetrahydrofuran (6 mL) and methanol (6 mL) was stirred at 60° C. for 1 hr. 1 N Hydrochloric acid (4.5 mL) was added to the reaction mixture, and the mixture was extracted with ethyl acetate. The extract washed with aqueous sodium chloride solution, dried over anhydrous magnesium sulfate, and concentrated under reduced pressure. The residue was subjected to silica gel column chromatography (ethyl acetate:hexane=1:4) to give a colorless oil (1.05 g). To a mixture of the obtained oil (1.05 g), 1 N aqueous sodium hydroxide solution (2.2 mL), methanol (2 mL) and water (20 mL) was slowly added a solution of calcium chloride (0.15 g, 1.2 mmol) in water (2 mL), and the precipitated solid was collected by filtration, washed with water, and dried to give the title compound (1.09 g, yield 99%) as a colorless amorphous powder. MS: m/z 532 (MH+), 1H NMR (DMSO-d6) δ: 1.17 (9H, s), 2.14-2.30 (2H, m), 2.44 (3H, s), 2.63-2.78 (2H, m), 4.98 (2H, s), 5.09 (2H, s), 5.11 (2H, s), 5.68 (1H, s), 6.62-6.82 (2H, m), 7.00-7.25 (5H, m), 7.28-7.38 (2H, m), 7.63 (1H, t, J=7.6 Hz).

Example 138 ethyl 3-{4-[(4-{[3-tert-butyl-5-(2-phenylethyl)-1H-pyrazol-1-yl]methyl}benzyl)oxy]-2-fluorophenyl}propanoate

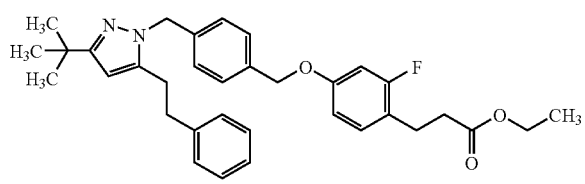

To a solution of 3-tert-butyl-5-(2-phenylethyl)-1H-pyrazole (250 mg, 1.1 mmol) in N,N-dimethylformamide (5 mL) was added sodium hydride (60% in oil, 40 mg, 1.0 mmol) at 0° C., and the mixture was allowed to warm to room temperature and stirred for 30 min. Ethyl 3-(4-{[4-(chloromethyl)benzyl]oxy}-2-fluorophenyl)propanoate (350 mg, 1.0 mmol) was added to the reaction mixture, and the mixture was stirred at room temperature for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give the title compound as a yellow oil. 1H NMR (CDCl3) δ: 1.22 (3H, t, J=7.2 Hz), 1.33 (9H, s), 2.57 (2H, t, J=7.6 Hz), 2.68-2.76 (2H, m), 2.78-2.83 (2H, m), 2.89 (2H, t, J=7.7 Hz), 4.11 (2H, q, J=7.2 Hz), 4.97 (2H, s), 5.21 (2H, s), 5.98 (1H, s), 6.60-6.69 (2H, m), 6.99-7.12 (5H, m), 7.16-7.30 (3H, m), 7.32 (2H, d, J=8.1 Hz).

Example 139

3-{4-[(4-{[3-tert-butyl-5-(2-phenylethyl)-1H-pyrazol-1-yl]methyl}benzyl)oxy]-2-fluorophenyl}propanoic acid

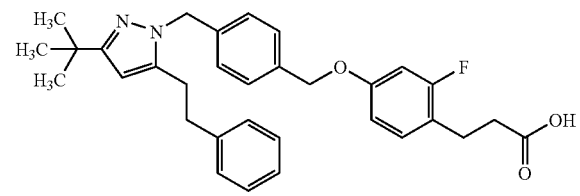

The oil obtained in Example 138 was dissolved in ethanol (3 mL) and tetrahydrofuran (3 mL), and 1 N aqueous sodium hydroxide solution (2 mL) was added. The mixture was stirred at room temperature for 1 hr. The reaction mixture was diluted with water, and neutralized with 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=9:1-1:4) to give the title compound (91 mg, yield 18%, 2 steps) as colorless crystals. $^1$H NMR (CDCl$_3$) δ: 1.32 (9H, s), 2.62 (2H, t, J=7.6 Hz), 2.68-2.76 (2H, m), 2.77-2.85 (2H, m), 2.89 (2H, t, J=7.6 Hz), 4.96 (2H, s), 5.22 (2H, s), 5.97 (1H, s), 6.59-6.66 (2H, m), 6.98-7.12 (5H, m), 7.16-7.34 (5H, m).

Example 140 ethyl 3-[4-({4-[(3-tert-butyl-5-phenyl-1H-pyrazol-1-yl)methyl]benzyl}oxy)-2-fluorophenyl]propanoate

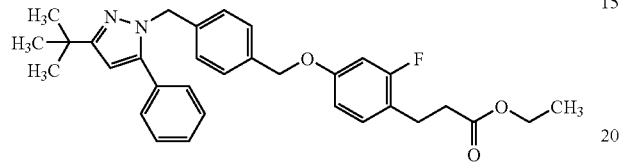

To a mixture of {4-[(3-tert-butyl-5-phenyl-1H-pyrazol-1-yl)methyl]phenyl}methanol (320 mg, 1.0 mmol), ethyl 3-(2-fluoro-4-hydroxyphenyl)propanoate (212 mg, 1.0 mmol), triphenylphosphine (262 mg, 1.0 mmol) and dichloromethane (5 mL) added dropwise diethyl azodicarboxylate (40% toluene solution, 435 mg, 1.0 mmol) with stirring at room temperature, and the mixture was stirred at room temperature for 1 hr. After completion of the reaction, the reaction mixture was purified by silica gel column chromatography (hexane:ethyl acetate=19:1-1:2) to give the title compound as a yellow oil. $^1$H NMR (CDCl$_3$) δ: 1.26 (3H, t, J=7.2 Hz), 1.37 (9H, s), 2.58 (2H, t, J=7.6 Hz), 2.90 (2H, t, J=7.6 Hz), 4.12 (2H, q, J=7.2 Hz), 4.97 (2H, s), 5.32 (2H, s), 6.20 (1H, s), 6.60-6.70 (2H, m), 7.02 (2H, d, J=8.1 Hz), 7.09 (1H, t, J=8.8 Hz), 7.25-7.40 (7H, m).

Example 141

3-[4-({4-[(3-tert-butyl-5-phenyl-1H-pyrazol-1-yl)methyl]benzyl)oxy)-2-fluorophenyl]propanoic acid

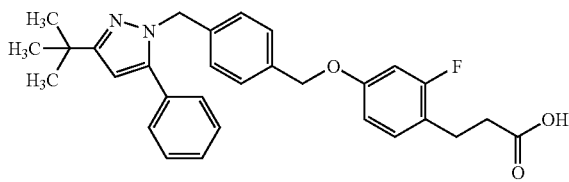

The oil obtained in Example 140 was dissolved in methanol (5 mL) and tetrahydrofuran (5 mL), and 2 N aqueous sodium hydroxide solution (3 mL) was added. The mixture was stirred at room temperature for 1 hr. The reaction mixture was diluted with water, and neutralized with 1 N aqueous hydrochloric acid solution, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=9:1-1:4) to give the title compound (90 mg, yield 18%, 2 steps) as colorless crystals. $^1$H NMR (CDCl$_3$) δ: 1.37 (9H, s), 2.64 (2H, t, J=7.6 Hz), 2.91 (2H, t, J=7.6 Hz), 4.97 (2H, s), 5.32 (2H, s), 6.20 (1H, s), 6.67 (2H, s), 7.01 (2H, d, J=8.3 Hz), 7.09 (1H, t, J=8.8 Hz), 7.25-7.40 (7H, m).

Example 142 ethyl 3-{2-fluoro-4-[(4-{[3-(4-fluorophenyl)-5-(2-phenylethyl)-1H-pyrazol-1-yl]methyl}benzyl)oxy]phenyl}propanoate

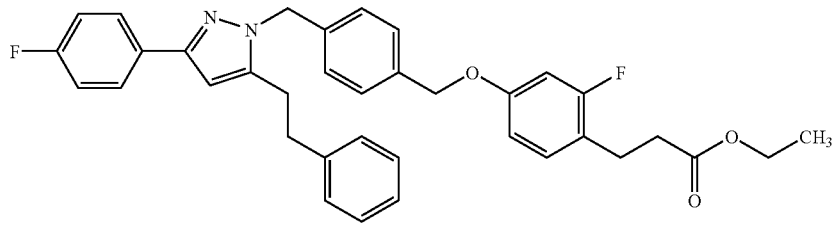

To a solution of 3-(4-fluorophenyl)-5-(2-phenylethyl)-1H-pyrazole (300 mg, 1.1 mmol) in N,N-dimethylformamide (5 mL) was added sodium hydride (60% in oil, 40 mg, 1.0 mmol) at 0° C., and the mixture was allowed to warm to room temperature and stirred for 30 min. Ethyl 3-(4-{[4-(chloromethyl)benzyl]oxy}-2-fluorophenyl)propanoate (350 mg, 1.0 mmol) was added to the reaction mixture, and the mixture was stirred at room temperature for 1 hr. The reaction mixture was poured into 1 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=19:1-1:1) to give the title compound as a yellow oil. $^1$H NMR (CDCl$_3$) δ: 1.26 (3H, t, J=7.2 Hz), 2.56 (2H, t, J=7.6 Hz), 2.78-2.93 (6H, m), 4.12 (2H, q, J=7.2 Hz), 4.98 (2H, s), 5.24 (2H, s), 6.37 (1H, s), 6.59-6.68 (2H, m), 7.03-7.13 (7H, m), 7.19-7.37 (5H, m), 7.77 (2H, dd, J=9.0, 5.5 Hz).

Example 143

3-(2-fluoro-4-[(4-{[3-(4-fluorophenyl)-5-(2-phenyl-ethyl)-1H-pyrazol-1-yl]methyl}benzyl)oxy]phenyl}propanoic acid

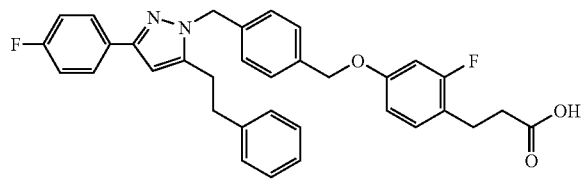

The oil obtained in Example 142 was dissolved in methanol (5 mL) and tetrahydrofuran (5 mL), and 2 N aqueous sodium hydroxide solution (2 mL) was added. The mixture was stirred at room temperature for 1 hr. The reaction mixture was neutralized with 6 N hydrochloric acid, and the mixture was extracted with ethyl acetate. The ethyl acetate layer was dried using a Presep Dehydration tube (Manufactured by Wako Pure Chemical Industries, Ltd.), and concentrated under reduced pressure. The residue was purified by silica gel column chromatography (hexane:ethyl acetate=9:1-1:4) to give the title compound (61 mg, yield 11%, 2 steps) as colorless crystals. $^1$H NMR (CDCl$_3$) δ: 2.62 (2H, t, J=7.5 Hz), 2.79-2.93 (6H, m), 4.98 (2H, s), 5.24 (2H, s), 6.37 (1H, s), 6.59-6.68 (2H, m), 7.03-7.14 (7H, m), 7.18-7.38 (5H, m), 7.76 (2H, dd, J=8.9, 5.5 Hz).

Formulation Example 1

(Production of Capsule)

| | |
|---|---|
| 1) compound of Example 1 | 30 mg |
| 2) microcrystalline cellulose | 10 mg |
| 3) lactose | 19 mg |
| 4) magnesium stearate | 1 mg |
| total | 60 mg |

The above-mentioned 1), 2), 3) and 4) are mixed and filled in a gelatin capsule.

Formulation Example 2

(Production of Tablet)

| | |
|---|---|
| 1) compound of Example 1 | 30 g |
| 2) lactose | 50 g |
| 3) corn starch | 15 g |
| 4) carboxymethylcellulose calcium | 44 g |
| 5) magnesium stearate | 1 g |
| 1000 tablets total | 140 g |

The total amount of the above-mentioned 1), 2) and 3) and 30 g of 4) are kneaded with water, vacuum dried and granulated. The granulated powder is mixed with 14 g of 4) and 1 g of 5) and tableted with a tableting machine. In this way, 1000 tablets containing 30 mg of the compound of Example 1 per tablet are obtained.

Experimental Example 1

Determination of EC$_{50}$ of the compound of the present invention against human GPR40

For determination of EC$_{50}$, CHO cell line that stably expressed human GPR40 was used. Unless otherwise indicated, the CHO cell line was cultured using α-MEM medium (Invitrogen) containing 10% fetal bovine serum (Invitrogen).

The cells cultured to nearly confluent were rinsed with PBS (Invitrogen) on the previous day of the assay, peeled off with 0.05% Trypsin.EDTA solution (Invitrogen) and recovered by centrifugation. The number of the obtained cells was counted, and the cells were diluted such that 3×10$^5$ cells were contained per 1 mL of the medium, dispensed to a black welled 96-well plate (coster) by 100 μL per well and cultured overnight in a CO$_2$ incubator. Various test compounds were added to the CHO cells thus prepared, and the changes in the intracellular calcium concentration were measured using FLIPR (Molecular Device). The below-mentioned pre-treatment was applied to measure changes in the intracellular calcium concentration by FLIPR.

First, an assay buffer for adding a fluorescence dye Fluo3-AM (DOJIN) to the cells, or for washing the cells immediately before FLIPR assay was prepared. To a solution of HBSS (Invitrogen, 1000 mL) added 1 M HEPES (pH 7.4, DOJIN, 20 mL) (hereinafter HBSS/HEPES solution) was added a solution (10 mL) obtained by dissolving probenecid (Sigma, 710 mg) in 1 N NaOH (5 mL), and adding and mixing an HBSS/HEPES solution (5 mL), and the resulting solution was used as an assay buffer. Next, Fluo3-AM (50 μg) was dissolved in dimethyl sulfoxide (Wako, 21 μL), and an equivalent amount of 20% pluronic acid (Molecular Probes) was added and mixed. The solution was added to the assay buffer (10.6 mL) supplemented with fetal bovine serum (105 μL) to give a fluorescence dye solution. The medium of the CHO cells inoculated to the black welled 96-well plate on the previous day of assay was removed, the fluorescence dye solution was immediately dispensed by 100 μL per well and the cells were cultured in a CO$_2$ incubator for 1 hr to allow intake of the fluorescence dye by the cells. The cells after the culture were washed with the above-mentioned assay buffer and set on FLIPR. The test compound was diluted with dimethylsulfoxide in advance, dispensed to a polypropylene 96-well plate (sample plate) by 2 μL, and cryopreserved at −20° C. To the thawed sample plate was added an assay buffer containing 0.015% CHAPS (DOJIN) by 198 μL, and simultaneously set on FLIPR together with the cell plate. After the aforementioned pre-treatment, changes in the intracellular calcium concentration upon addition of various test compounds was measured by FLIPR. Based on the results, a dose-response curve of each test compound was formed and EC$_{50}$ was calculated. The results are shown in Table 1.

TABLE 1

| receptor function modulating action on GPR40 | |
|---|---|
| Compound No. | EC$_{50}$ (nM) |
| Example 4 | <10 |
| Example 10 | <1000 |
| Example 20 | <100 |
| Example 24 | <10 |
| Example 29 | <100 |
| Example 40 | <10 |
| Example 45 | <100 |
| Example 56 | <1000 |
| Example 60 | <100 |

TABLE 1-continued

| receptor function modulating action on GPR40 | |
|---|---|
| Compound No. | $EC_{50}$ (nM) |
| Example 65 | <1000 |
| Example 111 | <1000 |
| Example 112 | <100 |
| Example 118 | <100 |
| Example 131 | <100 |
| Example 133 | <100 |
| Example 137 | <100 |
| Example 141 | <100 |

INDUSTRIAL APPLICABILITY

Compound (I), a salt thereof and a prodrug thereof have a superior GPR40 receptor function modulating action, and can be used as agents for the prophylaxis or treatment of diabetes and the like.

This application is based on application No. 2004-101 filed in Japan, the contents of which are incorporated hereinto by reference.

The invention claimed is:

1. A compound represented by the formula:

(I)

wherein
Het is an optionally substituted heterocyclic group,
n is 0 or 1,
$R^1$ and $R^2$ are the same or different and each is a hydrogen atom, a $C_{1-6}$ alkyl group or a halogen atom,
$R^3$ is an optionally substituted hydroxy group or an optionally substituted amino group,
$R^4$ is a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{6-14}$ aryl group, an optionally substituted $C_{7-16}$ aralkyl group, an optionally substituted hydroxy group or an optionally substituted amino group,
$R^5$ and $R^6$ are the same or different and each is a hydrogen atom, a $C_{1-6}$ alkyl group or a halogen atom, and
$R^7$ and $R^8$ are the same or different and each is a hydrogen atom, a $C_{1-6}$ alkyl group, a halogen atom or an optionally substituted hydroxy group,
or a salt thereof (except
4-[[3-(2-pyrazinyl)phenyl]methoxy]benzenepropanoic acid,
methyl 4-[[3-(2-pyrazinyl)phenyl]methoxy]benzenepropanoate,
methyl 4-[[3-[5-(trifluoromethyl)-2-pyridinyl]phenyl]methoxy]benzenepropanoate,
4-[[3-[5-(trifluoromethyl)-2-pyridinyl]phenyl]methoxy]benzenepropanoic acid,
4-[[3-(2-thiazolyl)phenyl]methoxy]benzenepropanoic acid,
methyl 4-[[3-(2-thiazolyl)phenyl]methoxy]benzenepropanoate,
4-[[3-(1H-pyrrol-1-yl)phenyl]methoxy]benzenepropanoic acid,
methyl 4-[[3-(1H-pyrrol-1-yl)phenyl]methoxy]benzenepropanoate,
4-[[3-(3-furyl)phenyl]methoxy]benzenepropanoic acid,
methyl 4-[[3-(3-furyl)phenyl]methoxy]benzenepropanoate,
4-[[3-(5-pyrimidinyl)phenyl]methoxy]benzenepropanoic acid,
4-[[3-(2-pyridinyl)phenyl]methoxy]benzenepropanoic acid,
methyl 4-[[3-(2-pyridinyl)phenyl]methoxy]benzenepropanoate,
4-[[3-(2-pyrimidinyl)phenyl]methoxy]benzenepropanoic acid,
methyl 4-[[3-(2-pyrimidinyl)phenyl]methoxy]benzenepropanoate,
4-[[3-(2-thienyl)phenyl]methoxy]benzenepropanoic acid,
methyl 4-[[3-(2-thienyl)phenyl]methoxy]benzenepropanoate,
4-[[3-(2-thienyl)phenyl]methoxy]benzenepropanoic acid and
methyl 4-[[3-(2-thienyl)phenyl]methoxy]benzenepropanoate).

2. A compound of claim 1, wherein Het is a group represented by the following formula:

wherein Het is as defined in claim 1, which is optionally substituted.

3. A compound of claim 1, wherein $R^3$ is a hydroxy group.
4. A compound of claim 1, wherein n is 1.
5. A compound of claim 1, wherein $R^1$ and $R^2$ are the same or different and each is a hydrogen atom or a halogen atom.
6. A compound of claim 1, wherein $R^4$ is a hydrogen atom or a $C_{1-6}$ alkoxy group.
7. A compound of claim 1, wherein $R^5$ and $R^6$ are hydrogen atoms.
8. A compound of claim 1, wherein $R^7$ and $R^8$ are hydrogen atoms.
9. A compound of claim 1, which is 3-(4-{[3-(1-benzothiophen-3-yl)benzyl]oxy}phenyl)propanoic acid;
3-(4-{[3-(2-methyl-3,4-dihydroquinolin-1 (2H)-yl)benzyl]oxy}phenyl)propanoic acid;
3-[4-({4-[(2-phenyl-1H-indol-1-yl)methyl]benzyl}oxy)phenyl]propanoic acid;
3-[2-fluoro-4-({4-[(2-phenyl-1H-indol-1-yl)methyl]benzyl}oxy)phenyl]propanoic acid;
3-[4-({4-[(2,5-diphenyl-1H-pyrrol-1-yl)methyl]benzyl}oxy)phenyl]propanoic acid;
3-(4-{[4-({5-(2-phenylethyl)-3-[4-(trifluoromethyl)phenyl]-1H-pyrazol-1-yl}methyl)benzyl]oxy}phenyl)propanoic acid;
3-[4-({4-[(3,5-diphenyl-1H-pyrazol-1-yl)methyl]benzyl}oxy)phenyl]propanoic acid;
3-{4-[(4-{[3-tert-butyl-5-(phenoxymethyl)-1H-pyrazol-1-yl]methyl}benzyl)oxy]-2-fluorophenyl}propanoic acid;

3-{4-[(4-{[5-(benzyloxy)-3-tert-butyl-1H-pyrazol-1-yl]methyl}benzyl)oxy]-2-fluorophenyl}propanoic acid;

3-(4-{[4-({3-tert-butyl-5-[(6-methylpyridin-2-yl)methoxy]-1H-pyrazol-1-yl}methyl)benzyl]oxy}-2-fluorophenyl)propanoic acid or a salt thereof.

10. A pharmaceutical agent comprising a compound of claim 1 together with a pharmaceutically acceptable carrier.

11. A method of promoting insulin secretion in a mammal, which comprises administering an effective amount of a compound of claim 1 to the mammal.

12. A method for the prophylaxis or treatment of diabetes in a mammal, which comprises administering an effective amount of a compound of claim 1 to the mammal.

* * * * *